(12) United States Patent
Jo et al.

(10) Patent No.: US 12,281,121 B2
(45) Date of Patent: Apr. 22, 2025

(54) N-CONTAINING HETEROARYL DERIVATIVE AND PHARMACEUTICAL COMPOSITION COMPRISING SAME AS ACTIVE INGREDIENT FOR PREVENTION OR TREATMENT OF CANCER

(71) Applicants: VORONOI Inc., Incheon (KR); VORONOIBIO Inc., Incheon (KR)

(72) Inventors: Seo Hyun Jo, Seoul (KR); Hua Li, Incheon (KR); Hee Sun Ryu, Incheon (KR); Hwan Kim, Seoul (KR); Ji Yoon Seok, Incheon (KR); Sun Hwa Lee, Incheon (KR); Jung Beom Son, Incheon (KR); Nam Doo Kim, Incheon (KR)

(73) Assignees: VORONOI Inc., Incheon (KR); VORONOIBIO Inc., Incheon (KR)

( * ) Notice: Subject to any disclaimer, the term of this patent is extended or adjusted under 35 U.S.C. 154(b) by 822 days.

(21) Appl. No.: 17/612,757

(22) PCT Filed: May 21, 2020

(86) PCT No.: PCT/KR2020/006648
§ 371 (c)(1),
(2) Date: Nov. 19, 2021

(87) PCT Pub. No.: WO2020/235945
PCT Pub. Date: Nov. 26, 2020

(65) Prior Publication Data
US 2022/0324874 A1  Oct. 13, 2022

(30) Foreign Application Priority Data
May 21, 2019 (KR) .................. 10-2019-0059476

(51) Int. Cl.
C07D 487/08 (2006.01)
A61P 35/00 (2006.01)
C07D 401/14 (2006.01)
C07D 519/00 (2006.01)

(52) U.S. Cl.
CPC ............ *C07D 487/08* (2013.01); *A61P 35/00* (2018.01); *C07D 401/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 9,802,937 B2 | 10/2017 | Thormann et al. | |
| 2009/0281073 A1 | 11/2009 | Bhattacharya et al. | |
| 2012/0329780 A1 | 12/2012 | Thormann et al. | |

FOREIGN PATENT DOCUMENTS

| CN | 103242341 A | 8/2013 |
|---|---|---|
| CN | 111285882 A | 6/2020 |
| JP | 2008525422 A | 7/2008 |
| JP | 2014511885 A | 5/2014 |
| KR | 20140004771 A | 1/2014 |
| WO | 2016127074 A1 | 8/2016 |
| WO | 2018136663 A1 | 7/2018 |
| WO | 2018232094 A1 | 12/2018 |
| WO | 2019045824 A1 | 3/2019 |
| WO | 2019075108 A1 | 4/2019 |

OTHER PUBLICATIONS

Extended European Search Report corresponding to European Patent Application No. 20808953.2 (6 pages) (dated May 30, 2023).
English translation of International Search Report corresponding to International Patent Application No. PCT/KR2020/006648 (3 pages) (mailed Aug. 24, 2020).

*Primary Examiner* — Bong-Sook Baek
(74) *Attorney, Agent, or Firm* — Myers Bigel, P.A.

(57) ABSTRACT

The present invention relates to an N-containing heteroaryl derivative and a pharmaceutical composition comprising same as an active ingredient for the prevention or treatment of cancer. The derivative exhibits high inhibitory activity against various protein kinases, particularly excellent ret proto-oncogene (RET) enzyme inhibitory ability, and has an excellent effect of inhibiting the proliferation of medullary thyroid cancer cells and lung cancer cells, which express RET fusion genes, and thus the derivative can be effectively used in the treatment of cancer, for example, medullary thyroid cancer or lung cancer, and particularly, can be effectively used in the treatment of cancer in which RET fusion genes are expressed.

8 Claims, No Drawings

N-CONTAINING HETEROARYL DERIVATIVE AND PHARMACEUTICAL COMPOSITION COMPRISING SAME AS ACTIVE INGREDIENT FOR PREVENTION OR TREATMENT OF CANCER

TECHNICAL FIELD

The present invention relates to an N-containing heteroaryl derivative and a pharmaceutical composition comprising same as an active ingredient for the prevention or treatment of cancer.

BACKGROUND ART

The development of cancer is associated with various environmental factors including chemicals, radiation, and viruses, and changes in tumor genes, tumor suppressor genes, and apoptosis and genes associated with DNA recovery, and the like, and recently, understanding of the molecular mechanism of such cancers has enabled targeted anticancer treatment, which is a new treatment method.

Targeted therapeutic agents are generally designed to exert effects by targeting molecules that cancer cells characteristically have, and the molecular targets are genes associated with a signal transduction pathway, angiogenesis, a matrix, a cell cycle regulator, apoptosis, and the like. Examples of those used as an important targeted therapeutic agent currently used in the treatment include 'signal transduction pathway suppressors' including tyrosine kinase suppressors and angiogenesis suppressors.

Phosphorylation on tyrosine residues in proteins is an important element of intracellular signal transduction. An enzyme capable of catalyzing such a reaction is called a tyrosine kinase. A large number of transmembrane receptors include a domain with tyrosine kinase activity, and are classified as receptor tyrosine kinases (RTKs).

RTKs transmit extracellular signals in various processes, such as cell growth, differentiation, survival, and programmed cell death. In response to binding to extracellular ligands, RTKs generally recognize dimerized and phosphorylated forms of RTKs and induce intracellular signaling and autophosphorylation by interacting effectors. There are many members of this RTK family, one of which is a RET proto oncogene, which encodes a 120 kDa protein rearranged during transfection (RET). The RET is a receptor for growth factors of a glial cell line-derived neurotrophic factor (GDNF) family. Two ligands for the RET have been identified; GDNF and neutrin (NTN). The RET is activated when a ligand thereof binds to a co-receptor, and then a complex interacts with the RET (Eng, 1999 Journal Clinical Oncology: 17(1) 380-393).

Such activation phosphorylates the RET in tyrosine residues and induces signaling for cell growth and differentiation through the RAS-RAF and PI3 kinase pathways and other possible pathways.

It is known that point mutants that activate the RET induce three associated dominantly inherited cancer syndromes; multiple endocrine neoplasia types 2A and 2B (MEN2A and MEN2B), and familial medullary thyroid cancer (FMTC) (Santoro et al. 2004 Endocrinology: 145, 5448-5451).

In almost all MEN2A cases and some FTMC cases, cysteine substitution occurs in a juxtamembrane cysteine-rich domain, whereas in 95% of MEN2B, a single point mutation occurs at codon 918 on the kinase domain (M918T). Codon 918 is considered to be located on a substrate recognition pocket in a catalytic core. Mutations at this site are thought to structurally activate RET by altering the active loop structure of a RET catalytic domain. The M918T mutation is also found in sporadic medullary cancer, which is associated with the phenotype of a progressive disease. In vitro studies show that mutations affect substrate specificity, and thus the RET recognizes and phosphorylates substrates preferred by non-receptor tyrosine kinases such as c-src and c-abl (Eng et al. 1996 JAMA 276, 1575-1579; Ponder et al. 1999 Cancer Research 59, 1736-1741; Schilling et al. 2001 International Journal of Cancer 95, 62-66; Santoro et al. 1995 Science 267, 381-383; Zhou et al. 1995 Nature 273, 536-539).

As mutations on the RET gene are identified in most of the MEN2 family, they enable molecular diagnostic tests and may also be useful in order to confirm clinical diagnoses. A RET mutation test may be performed using a protocol based on a polymerase chain reaction, where a target axon sequence is amplified for direct sequencing or restriction endonuclease digestion (Zhong et al. 2006 Clinica Chimica Acta 364, 205-208).

Another member of the RTK family is vascular endothelial growth factor receptor 2 (VEGFR2) (kinase insert domain-containing receptor, KDR (also referred to Flk1)). VEGFR2 is a receptor for vascular endothelial growth factor (VEGF). VEGF is considered to be an important stimulant of both normal angiogenesis and disease-related angiogenesis (Jakeman, et al. 1993 Endocrinology 133, 848-859; Kolch, et al. 1995 Breast Cancer Research and Treatment 36, 139-155) and vascular permeability (Connolly, et al. 1989 J. Biol. Chem 264, 20017-20024). VEGF antagonism by sequestration of antibodies and VEGF can suppress tumor growth (Kim, et al. 1993 Nature 362, 841-844). The heterologous cleavage of a VEGF gene induces a fatal defect in vascularization (Carmeliet, et al. 1996 Nature 380435-439; Ferrara, et al. 1996 Nature 380439-442).

VEGF binding to VEGFR2 induces receptor dimerization, resulting in VEGFR2 autophosphorylation of specific intracellular tyrosine residues. Autophosphorylation increases the catalytic activity of tyrosine kinases and provides a potential docking site for cytoplasmic signaling such as phospholipase C-γ. This protein interaction mediates VEGFR2, for example, intracellular signaling essential for inducing cellular responses to endothelial cell proliferation, survival and migration (Ryan et al. 2005 British Journal Cancer: 92(Suppl.1) S6-S13).

Recognition of the important role of VEGF-mediated VEGFR2 signaling in pathological angiogenesis has led to the development of various selective approaches to suppress VEGFR2 activation. They include small molecule ATP-competitive tyrosine kinase suppressors, which prevent autophosphorylation and continuous intracellular signaling in ATP binding suppression (Ryan, 2005).

Quinazoline derivatives, which are suppressors of VEGF receptor tyrosine kinase, are described in International Publication Nos. WO98/13354 and WO01/32651. WO98/13354 and WO01/32651 disclose compounds that have partial activity against epidermal growth factor receptor (EGFR) tyrosine kinase and activity against VEGF receptor tyrosine kinase.

A compound 4-(4-bromo-2-fluoroanilino)-6-methoxy-7-(1-methylpiperidin-4-ylmethoxy)quinazoline, which is a VEGFR2 tyrosine kinase suppressor is disclosed (Wedge et al., 2002 Cancer Research 62, 4645-4655). This compound is also known as Zactima® (registered trademark), which is Code No. ZD6474 and the generic trade name vandetanib. Hereinafter, the compound will be referred to as vandetanib.

Vandetanib was developed as a suppressor with strong and reversible ATP-binding to VEGFR2 tyrosine kinase. Further, vandetanib suppresses EGFR tyrosine kinase activity. The EGFR signaling pathway is an important factor not only in tumor cell proliferation, survival, and invasion, but also in cancer progression where VEGF increases overexpression. Suppression of EGFR signaling has been revealed to induce selective apoptosis in tumor endothelial cells.

In 2002, vandetanib was reported to be capable of suppressing signaling and deformability of RET as a potent suppressor of ligand-dependent RET tyrosine kinase activity. In addition, it was reported that vandetanib has a potent growth suppressive effect on RET-dependent thyroid tumor cell growth in vitro (Carlomagno et al. 2002 Cancer Research: 62, 7284-7290).

Vandetanib also suppressed most of the mutated active forms of RET and wild-type receptors. Therefore, suppression of RET tyrosine kinase by vandetanib as well as suppression of VEGFR2 and EGFR tyrosine kinase can also impart an additional antitumor effect in tumor treatment accompanied by mutations of the RET gene which induces RET-dependent tumor cell growth (Ryan, 2005).

DISCLOSURE

Technical Problem

An object of the present invention is to provide an N-containing heteroaryl derivative or an isomer thereof, a solvate thereof, a hydrate thereof, or a pharmaceutically acceptable salt thereof.

Another object of the present invention is to provide a method for preparing the compound.

Still another object of the present invention is to provide a pharmaceutical composition containing an N-containing heteroaryl derivative, or an isomer thereof, a solvate thereof, a hydrate thereof, or a pharmaceutically acceptable salt thereof as an active ingredient for the prevention or treatment of cancer.

Yet another object of the present invention is to provide a method for the prevention or treatment of cancer, the method containing an N-containing heteroaryl derivative, or an isomer thereof, a solvate thereof, a hydrate thereof, or a pharmaceutically acceptable salt thereof as an active ingredient.

Yet another object of the present invention is to provide a use of the N-containing heteroaryl derivative or the isomer thereof, the solvate thereof, hydrate thereof, or the pharmaceutically acceptable salt thereof for use in the preparation of a medicine used for the prevention or treatment of cancer.

Technical Solution

To achieve the above objects,

An aspect of the present invention provides a compound of the following Chemical Formula 1, an isomer thereof, a solvate thereof, a hydrate thereof, or a pharmaceutically acceptable salt thereof:

[Chemical Formula 1]

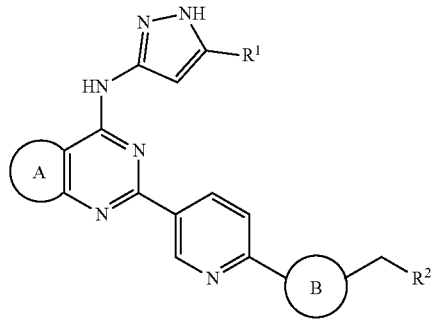

wherein

is furan, thiophene, benzene, or cyclopentene, $R^1$ is a straight or branched $C_1$-$C_3$ alkyl, wherein $R^1$ is unsubstituted or substituted with at least one halogen, Ring B is diazabicycloheptane, piperazine, diazepane, or diazaspirooctane, wherein Ring B is unsubstituted or substituted with at least one straight or branched $C_1$-$C_6$ alkyl, $R^2$ is pyridinyl, thiazolyl, phenyl, imidazolyl, pyrazinyl, quinolinyl, pyrimidinyl, or pyridonyl, wherein $R^2$ is unsubstituted or substituted with at least one $R^3$—, and $R^3$ is at least one substituent selected from the group consisting of a straight or branched $C_1$-$C_6$ alkyl, a straight or branched $C_1$-$C_6$ haloalkyl, a straight or branched $C_1$-$C_6$ alkoxy, a halogen, a $C_1$-$C_3$ alkanesulfonamido, an amino substituted with at least one straight or branched $C_1$-$C_3$ alkyl, and nitrile.

Another aspect of the present invention provides a method for preparing a compound of Chemical Formula 1, the method comprising:

preparing a compound of Chemical Formula 3 from a compound of Chemical Formula 2;

preparing a compound of Chemical Formula 4 from the compound of Chemical Formula 3;

preparing a compound of Chemical Formula 5 from the compound of Chemical Formula 4;

preparing a compound of Chemical Formula 6 from the compound of Chemical Formula 5;

preparing a compound of Chemical Formula 7 from the compound of Chemical Formula 6; and preparing the compound of Chemical Formula 1 from the compound of Chemical Formula 7:

[Chemical Formula 2]

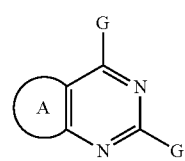

-continued

[Chemical Formula 3]

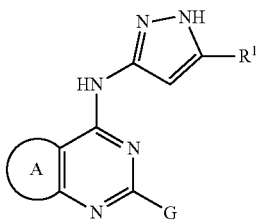

[Chemical Formula 4]

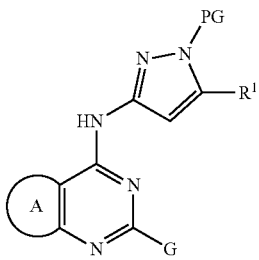

[Chemical Formula 5]

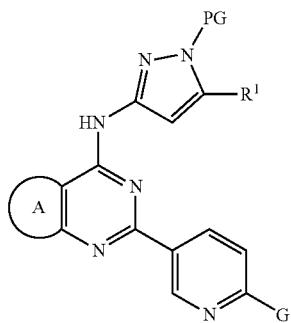

[Chemical Formula 6]

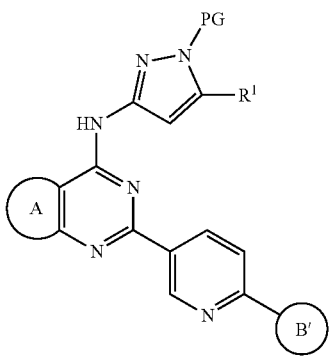

[Chemical Formula 7]

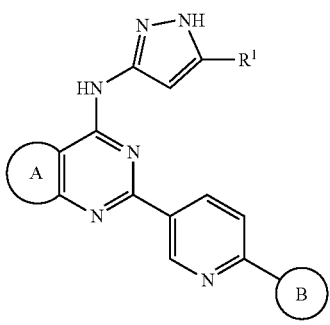

-continued

[Chemical Formula 1]

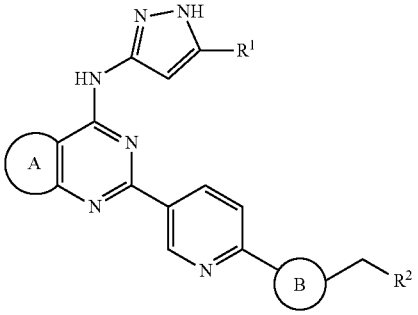

wherein $R^1$, $R^2$,

and Ring B are the same as those defined above, respectively,

G is a leaving group,

PG is a protecting group, and

Ring B' has the same structure as Ring B, but is a form in which one nitrogen atom is protected by a protecting group.

Still another aspect of the present invention provides a pharmaceutical composition containing the compound of the present invention, or an isomer thereof, a solvate thereof, a hydrate thereof, or a pharmaceutically acceptable salt thereof as an active ingredient for the prevention or treatment of cancer.

Advantageous Effects

A compound of Chemical Formula 1 according to the present invention exhibits high inhibitory activity against various protein kinases, particularly excellent ret proto-oncogene (RET) enzyme inhibitory ability, and has an excellent effect of inhibiting the proliferation of medullary thyroid cancer cells and lung cancer cells, which express RET fusion genes, and thus the derivative can be effectively used in the treatment of cancer, for example, medullary thyroid cancer or lung cancer, and particularly, can be effectively used in the treatment of cancer in which RET fusion genes are expressed.

[Modes of the Invention]

Hereinafter, the present invention will be described in detail.

The exemplary embodiments of the present invention may be modified into various other forms, and the scope of the present invention is not limited to the exemplary aspects to be described below. Further, the exemplary embodiments of the present invention are provided to more fully describe the present invention to a person with ordinary skill in the art.

"Including" a certain element throughout the specification means that it does not exclude other elements, but may further include other elements unless otherwise particularly described.

In the structural formulas of the present specification, the symbol — binding an atom and/or a group may mean a single bond and the symbol = may mean a double bond.

The symbols may be omitted and may also be displayed if necessary, such as when specifying a bonding atom or bonding position.

In the present specification, the linkage of atoms may include not only the case of direct linkage of atoms but also the case of indirect linkage of atoms mediated by other atoms and/or groups. In this case, other atoms and/or groups may be oxygen, sulfur, a $C_{1-8}$ alkylamino, a $C_{1-8}$ alkylene group, or the like, and are not limited thereto, and the atom and/or the group may be substituted or unsubstituted.

In the present specification, being substituted or unsubstituted may mean that one hydrogen atom or a plurality of hydrogen atoms is/are unsubstituted or substituted with other atoms or substituents unless otherwise stated. The substituent may be at least one selected from the group consisting of a halogen (chloro (Cl), iodo (I), bromo (Br), fluoro (F)), a $C_{1\sim10}$ alkyl, a $C_{2\sim10}$ alkenyl, a $C_{2\sim10}$ alkynyl, hydroxyl, a $C_{1\sim10}$ alkoxy, amino, nitro, thiol, thioether, imine, cyano, phosphonato, phosphine, carboxy, carbamoyl, carbamic acid, acetal, urea, thiocarbonyl, sulfonyl, sulfonamide, ketone, aldehyde, ester, acetyl, acetoxy, amide, oxygen (=O), a haloalkyl (for example, trifluoromethyl), substituted aminoacyl and aminoalkyl, a carbocyclic cycloalkyl, which may be monocyclic or a fused or non-fused polycyclic (for example, cyclopropyl, cyclobutyl, cyclopentyl, or cyclohexyl), or a heterocycloalkyl, which may be monocyclic or a fused or non-fused polycyclic (for example, pyrrolidinyl, piperidinyl, piperazinyl, morpholinyl, or thiazinyl), carbocyclic or heterocyclic, monocyclic or a fused or non-fused polycyclic aryl (for example, phenyl, naphthyl, pyrrolyl, indolyl, furanyl, thienyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothienyl, or benzofuranyl), amino (primary, secondary, or tertiary), aryl, aryloxy, and aryl-alkyl, and is not limited thereto. In addition, each of the exemplified substituents may be unsubstituted or substituted again with a substituent selected from the group of these substituents.

In the present specification, the halogen may be F, $C_1$, Br, or I.

In the present specification, the alkyl may mean a straight or branched non-cyclic; cyclic; or saturated hydrocarbon to which they are bonded, unless otherwise described. Furthermore, the $C_{1-8}$ alkyl may mean an alkyl including 1 to 8 carbon atoms. The non-cyclic alkyl may include, as an example, methyl, ethyl, N-propyl, N-butyl, N-pentyl, N-hexyl, N-heptyl, N-octyl, isopropyl, sec-butyl, isobutyl, tert-butyl, isopentyl, 2-methylpentyl, 3-methylpentyl, 4-methylpentyl, 2,3-dimethylbutyl, and the like, but is not limited thereto. The cyclic alkyl may include, as an example, cyclopropyl, cyclobutyl, cyclopentyl, cyclohexyl, cycloheptyl, cyclooctyl, or the like, but is not limited thereto. The alkyl to which the non-cyclic alkyl and the cyclic alkyl are bonded includes, for example, methylcyclopropyl, Cyclopropylmethyl, ethylcyclopropyl, cyclo propylethyl, methylcyclobutyl, cyclobutylmethyl, ethylcyclopentyl, cycloheptylmethyl, or the like, but is not limited thereto.

As used herein, the cycloalkyl may refer to, particularly, a cyclic alkyl among alkyls, wherein alkyl is the same as defined above.

As used herein, the alkoxy may refer to —(O-alkyl) as an alkyl ether group, wherein alkyl is the same as defined above. Further, a $C_{1-8}$ alkoxy may refer to an alkoxy containing a $C_{1-8}$ alkyl, that is, —(O—$C_{1-8}$ alkyl), and as an example, the $C_{1-8}$ alkoxy may include methoxy, ethoxy, n-propoxy, isopropoxy, n-butoxy, iso-butoxy, sec-butoxy, tert-butoxy, n-pentoxy, and the like, but is not limited thereto.

As used herein, the heterocycloalkyl may refer to a ring containing 1 to 5 heteroatoms selected from N, O, and S as an atom forming a ring, and may be saturated or partially unsaturated. Unless otherwise stated, the heterocycloalkyl may be a monocyclic ring or a polycyclic ring such as a spiro ring, a bridged ring or a fused ring. In addition, a heterocycloalkyl of 3 to 12 atoms may refer to a heterocycloalkyl including 3 to 12 atoms forming a ring, and as an example, the heterocycloalkyl may include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1 S,4S)-2-azabicyclo[2.2.2]octane, (1R,4R)-2-oxa-5-azabicyclo[2.2.2]octane, or the like, but is not limited thereto.

As used herein, the alkylamino may refer to —(NR'R"), wherein R' and R" may be each independently selected from the group consisting of hydrogen and a $C_{1-8}$ alkyl, and the selected R' and R" may be each independently substituted or unsubstituted. In addition, the $C_{1-8}$ alkylamino may refer to an amino containing a $C_{1-8}$ alkyl, that is, —N—H($C_{1-8}$alkyl) or —N—($C_{1-8}$ alkyl)$_2$, and may include dimethylamino, diethylamino, methylethylamino, methylpropylamino, or ethylpropylamino, but is not limited thereto.

As used herein, the aryl may refer to an aromatic ring in which one hydrogen is removed from an aromatic hydrocarbon ring, and may be a monocyclic ring or a polycyclic ring. An aryl of 3 to 12 atoms may refer to an aryl including 3 to 12 atoms forming a ring, and may include, as an example, phenyl, naphthyl, anthracenyl, phenanthryl, biphenyl, terphenyl, or the like, but is not limited thereto.

As used herein, the heteroaryl may refer to an aromatic ring containing one or more heteroatoms of N, O, and S as an atom forming a ring, and may be a monocyclic ring or a polycyclic ring. Furthermore, the heteroaryl of 3 to 12 atoms may refer to a heteroaryl including 3 to 12 atoms forming a ring, and may include, as an example, thienyl, thiophene, furyl, pyrrolyl, pyrazolyl, imidazolyl, thiazolyl, oxazolyl, isothiazolyl, oxadiazolyl, triazolyl, pyridinyl, bipyridyl, pyrimidyl, triazinyl, triazolyl, acridyl, pyridazinyl, pyrazinyl, qunolinyl, quinazoline, quinoxalinyl, phenoxazyl, phthalazinyl, pyrimidinyl, pyrido pyrimidinyl, pyrido pyrazinyl, pyrazino pyrazinyl, isoquinoline, indole, carbazole, imidazopyridazinyl, imidazopyridinyl, imidazopyrimidinyl, pyrazolopyrimidinyl, imidazopyrazinyl or pyrazolopyridinyl, N-arylcarbazole, N-heteroarylcarbazole, N-alkylcarbazole, benzoxazole, benzoimidazole, benzothiazole, benzocarbazole, benzothiophene, dibenzothiophenyl, thienothiophene, benzofuranyl, phenanthroline, isoxazolyl, oxadiazolyl, thiadiazolyl, benzothiazolyl, tetrazolyl, phenothiazinyl, dibenzosilole, dibenzofuranyl, or the like, but is not limited thereto.

As used herein, the "hydrate" may refer to the compound of the present invention including a stoichiometric or non-stoichiometric amount of water bonded by a non-covalent intermolecular force, or a salt thereof. A hydrate of the compound of Chemical Formula 1 of the present invention may include a stoichiometric or non-stoichiometric amount of water bonded by a non-covalent intermolecular force. The hydrate may contain at least 1 equivalent, preferably 1 to 5 equivalents of water. Such a hydrate may be prepared by crystallizing the compound of Chemical Formula 1 of the present invention, an isomer thereof, or pharmaceutically acceptable salt thereof from water or a solvent containing water.

As used herein, the "solvate" may refer to the compound of the present invention including a stoichiometric or non-stoichiometric amount of solvent bonded by a non-covalent intermolecular force, or a salt thereof. Preferred solvents with respect to the solvate include volatile, non-toxic, and/or solvents suitable for administration to humans.

As used herein, the "isomer" may refer to a compound of the invention, which has the same chemical or molecular formula but is structurally or sterically different, or a salt thereof. Such isomers include all of a structural isomer such as a tautomer, a R or S isomer having an asymmetric carbon center, a steric isomer such as a geometric isomer (trans, cis), and an optical isomer (enantiomer). All of these isomers and mixtures thereof are also included within the scope of the present invention.

The Present Invention Provides a compound of the following Chemical Formula 1, an isomer thereof, a solvate thereof, a hydrate thereof, or a pharmaceutically acceptable salt thereof.

[Chemical Formula 1]

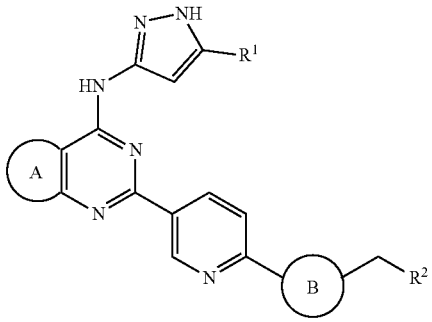

wherein

is furan, thiophene, benzene, or cyclopentene, $R^1$ is a straight or branched $C_1$-$C_3$ alkyl, wherein $R^1$ is unsubstituted or substituted with at least one halogen, Ring B is diazabicycloheptane, piperazine, diazepane, or diazaspirooctane, wherein Ring B is unsubstituted or substituted with at least one straight or branched $C_1$-$C_6$ alkyl, $R^2$ is pyridinyl, thiazolyl, phenyl, imidazolyl, pyrazinyl, quinolinyl, pyrimidinyl, or pyridonyl, wherein $R^2$ is unsubstituted or substituted with at least one $R^3$, and $R^3$ is at least one substituent selected from the group consisting of a straight or branched $C_1$-$C_6$ alkyl, a straight or branched $C_1$-$C_6$ haloalkyl, a straight or branched $C_1$-$C_6$ alkoxy, a halogen, a $C_1$-$C_3$ alkanesulfonamido, an amino substituted with at least one straight or branched $C_1$-$C_3$ alkyl, and nitrile.

In one embodiment of the present invention, Ring B may be 3,6-diazabicyclo[3.1.1]heptane, 2,5-diazabicyclo[2.2.1]heptane, piperazine, diazepane or 4,7-diazaspiro[2,5]octane.

In one embodiment of Ring B, Ring B may be linked to another adjacent group through two nitrogen atoms.

In another embodiment of the present invention, when $R^2$ is pyridinyl, thiazolyl, phenyl, pyrazinyl, pyrimidinyl, or pyridonyl, $R^2$ is substituted with at least one $R^3$, or when $R^2$ is imidazolyl or quinoline, $R^2$ is not substituted, and $R^3$ may be at least one substituent selected from the group consisting of a straight or branched $C_1$-$C_3$ alkyl, a straight or branched $C_1$-$C_3$ haloalkyl, a straight or branched $C_1$-$C_3$ alkoxy, a halogen, a $C_1$-$C_3$ alkanesulfonamido, an amino substituted with at least one straight or branched $C_1$-$C_3$ alkyl, and nitrile.

Examples of the compound of Chemical Formula 1 according to the present invention include Compounds 1 to 37 listed in [Table 1] of the following Examples, or pharmaceutically acceptable salts thereof, or free bases (when shown as the pharmaceutically acceptable salt in Table 1), isomers thereof, solvates thereof, or pharmaceutically acceptable salts thereof.

The compound of Chemical Formula 1 of the present invention may be used in the form of a pharmaceutically acceptable salt, and as the salt, an acid addition salt formed of a pharmaceutically acceptable free acid is useful. The acid addition salt is obtained from an inorganic acid such as hydrochloric acid, nitric acid, phosphoric acid, sulfuric acid, hydrobromic acid, hydriodic acid, nitrous acid, and phosphorous acid, a non-toxic organic acid such as aliphatic mono and dicarboxylates, phenyl-substituted alkanoates, hydroxy alkanoates and alkanedionates, aromatic acids, and aliphatic and aromatic sulfonic acid, and an organic acid such as trifluoroacetic acid, acetate, benzoic acid, citric acid, lactic acid, maleic acid, gluconic acid, methanesulfonic acid, 4-toluenesulfonic acid, tartaric acid, and fumaric acid. Types of such pharmaceutically non-toxic salts include sulfate, pyrosulfate, bisulfate, sulfite, bisulfate, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butine-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate, and the like.

The acid addition salt according to the present invention may be prepared by a typical method, for example, by dissolving the derivative of Chemical Formula 1 in an organic solvent such as methanol, ethanol, acetone, methylene chloride, and acetonitrile and adding an organic acid or an inorganic acid thereto to filter and dry the resulting precipitate, or may be prepared by distilling a solvent and an excess amount of acid under reduced pressure, and then drying the solvent and the acid to crystallize the resulting product under an organic solvent.

Further, a pharmaceutically acceptable metal salt may be prepared using a base. An alkali metal or alkaline earth metal salt is obtained by, for example, dissolving the compound in an excess alkali metal hydroxide or alkaline-earth metal hydroxide solution, filtering the non-soluble compound salt, evaporating the filtrate, and drying the result product. In this case, preparing a sodium, potassium or calcium salt as the metal salt is pharmaceutically suitable. Further, a salt corresponding to this is obtained by reacting the alkali metal or alkaline earth metal salt with a suitable silver salt (for example, silver nitrate).

Furthermore, the present invention includes not only the compound of Chemical Formula 1 and a pharmaceutically acceptable salt thereof, but also a solvate, an optical isomer, a hydrate and the like that can be prepared therefrom.

Another aspect of the present invention may provide a method for preparing a compound of Chemical Formula 1.

The method for preparing a compound of Chemical Formula 1 may include:

preparing a compound of Chemical Formula 3 from the compound of Chemical Formula 2;

preparing a compound of Chemical Formula 4 from the compound of Chemical Formula 3;

preparing a compound of Chemical Formula 5 from the compound of Chemical Formula 4;

preparing a compound of Chemical Formula 6 from the compound of Chemical Formula 5;

preparing a compound of Chemical Formula 7 from the compound of Chemical Formula 6; and preparing the compound of Chemical Formula 1 from the compound of Chemical Formula 7.

[Chemical Formula 2]

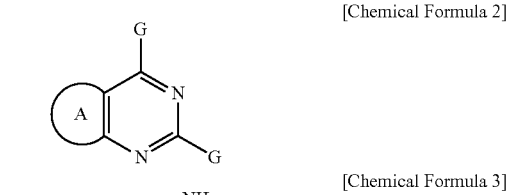

[Chemical Formula 3]

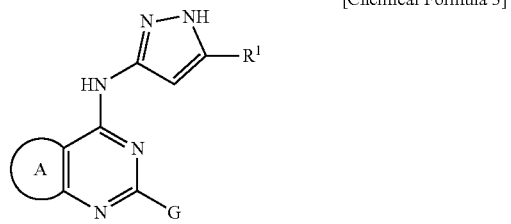

[Chemical Formula 4]

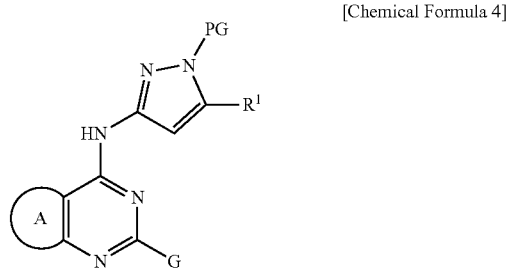

[Chemical Formula 5]

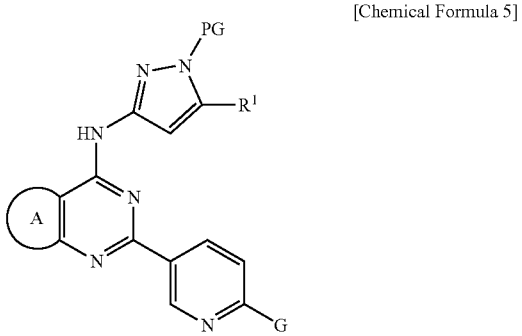

[Chemical Formula 6]

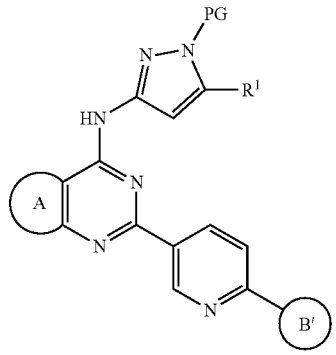

[Chemical Formula 7]

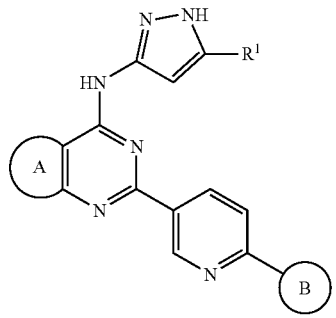

[Chemical Formula 1]

$R^1$, $R^2$,

and Ring B are each the same as those defined in the present specification, G is a leaving group, PG is a protecting group, and Ring B' has the same structure as Ring B, but is a form in which one nitrogen atom is protected by a protecting group.

The leaving group may be a functional group such as a halogen, sulfonic acid ester, or alkoxy, and is not limited as long as it is a functional group capable of preparing a target compound by releasing the leaving group from the compound of Chemical Formulae 2 to 5. The protecting group may be a functional group such as t-butoxycarbonyl, benzyloxycarbonyl, 3,4-dihydro-2H-pyran, and tetrahydro-2H-pyran, and is not limited as long as it is a functional group capable of protecting a secondary amine of Chemical Formulae 4 to 6.

The preparing of the compound of Chemical Formula 3 from the compound of Chemical Formula 2 may be a step of reacting the compound of Chemical Formula 2 with

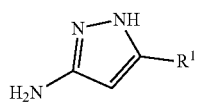

N,N-diisopropylethylamine (DIPEA) may be further added to the reaction, the reaction temperature may be approximately 40 to 100° C., and the reaction time may be approximately 10 to 14 hours, and as long as the reaction smoothly proceeds, the reaction may not be limited to the above conditions.

The preparing of the compound of Chemical Formula 4 from the compound of Chemical Formula 3 may be a step of protecting a secondary amine of a pyrazole group from the compound of Chemical Formula 3. The protecting group may be used without limitation as long as it is a functional group capable of protecting a secondary amine, and may be tetrahydro-2H-pyran (THP) as an example.

The preparing of the compound of Chemical Formula 5 from the compound of Chemical Formula 4 may be a step of reacting the compound of Chemical Formula 4 with

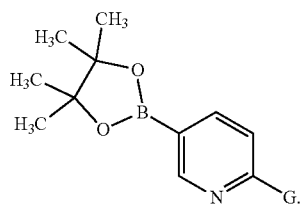

The reaction may be performed in a solvent such as dioxane, Pd(dppf)Cl$_2$·CH$_2$Cl$_2$ may be further added thereto, the reaction temperature may be approximately 80 to 100° C., and the reaction time may be approximately 2 to 4 hours. As long as the reaction smoothly proceeds, the reaction may not be limited to the above conditions.

The preparing of the compound of Chemical Formula 6 from the compound of Chemical Formula 5 may be a step of linking Ring B' to the compound of Chemical Formula 5. Ring B' is a form in which one nitrogen atom of Ring B as defined in the present specification is protected with a protecting group, the protecting group may be used without limitation as long as it is a protecting group capable of protecting a secondary amine, and may be t-butoxycarbonyl (BOC) as an example.

A more specific exemplary embodiment of the present step may be a step of reacting an unprotected secondary amine of Ring B' with the compound of Chemical Formula 5 to link Ring B' to the compound of Chemical Formula 5. The step may be performed in a solvent such as DMSO, K$_2$CO$_3$ may be further added thereto, the reaction temperature may be approximately 100 to 140° C., and the reaction time may be approximately 10 to 14 hours. As long as the reaction smoothly proceeds, the reaction may not be limited to the above conditions.

The preparing of the compound of Chemical Formula 7 from the compound of Chemical Formula 6 may be a step of de-protecting a protecting group attached to the compound of Chemical Formula 6. The step may de-protect the protecting group by dissolving the compound of Chemical Formula 6 in an HCl solution.

The preparing of the compound of Chemical Formula 1 from the compound of Chemical Formula 7 may be a step of reacting the compound of Chemical Formula 7 with CHO—R$^2$. The reaction may be performed in a solvent such as N,N-dimethylacetamide (DMA), and a compound of Chemical Formula 1 may be formed through a reductive alkylation reaction of an aldehyde with a secondary amine. Any reducing agent that reductively alkylates an aldehyde and a secondary amine can be used without limitation, and NaBH(OAc)$_3$ may be used as an example. The reaction temperature may be approximately 40 to 80° C., and the reaction time may be approximately 3 to 8 hours. As long as the reaction smoothly proceeds, the reaction may not be limited to the above conditions.

Still another aspect of the present invention provides a pharmaceutical composition containing the compound of Chemical Formula 1, an optical isomer thereof, or a pharmaceutically acceptable salt thereof as an active ingredient for the prevention or treatment of cancer.

The compound may exhibit inhibitory activity against one or more protein kinases selected from the group consisting of ABL1(H396P)-nonphosphorylated, ABL1(H396P)-phosphorylated, ABL1(M351T)-phosphorylated, ABL1 (Q252H)-phosphorylated, ABL1(T315I)-nonphosphorylated, ABL1(T315I)-phosphorylated, ABL1(Y253F)-phosphorylated, ABL1-phosphorylated, AMPK-alpha1, AURKA, AURKC, AXL, BLK, BTK, CSNK2A1, CSNK2A2, DAPK3, DDR1, DDR2, DLK, EGFR(L747-E749del, A750P), EGFR(L858R,T790M), EGFR(T790M), EPHB6, FGFR1, FGR, FLT3, FLT3(D835H), FLT3 (D835V), FLT3(D835Y), FLT3(ITD), FLT3(ITD,D835V), FLT3(ITD,F691L), FLT3(K663Q), FLT3(N841I), FLT3 (R834Q), FLT3-autoinhibited, FRK, GCN2(Kin.Dom.2, S808G), HCK, ICK, ITK, JAK1(JH1domain-catalytic), JAK1(JH2domain-pseudokinase), JAK2(JH1domain-catalytic), JAK3(JH1domain-catalytic), KIT(A829P), KIT (D816V), KIT(V559D), LCK, MAP3K2, MEK2, MEK3, MEK5, MERTK, MST1, PDGFRB, PLK4, RET, RET (M918T), RET(V804L), RET(V804M), RIOK3, SNARK, SRC, SYK, TRKA, TRKB, TRKC, TYK2(JH1domain-catalytic), YES, and YSK4.

Further, the compound may exhibit RET enzyme inhibitory activity.

The cancer may be one or more selected from the group consisting of pseudomyxoma, intrahepatic cholangiocarcinoma, hepatoblastoma, liver cancer, thyroid cancer, medullary thyroid carcinoma, colon cancer, testicular cancer, myelodysplastic syndrome, glioblastoma, oral cancer, lip cancer, mycosis fungoides, acute myelogenous leukemia, acute lymphoblastic leukemia, basal cell carcinoma, ovarian epithelial cancer, ovarian germ cell cancer, male breast cancer, brain cancer, pituitary adenoma, multiple myeloma, gallbladder cancer, bile duct cancer, colorectal cancer, chronic myelogenous leukemia, chronic lymphocytic leukemia, retinoblastoma, choroidal melanoma, ampulla of Vater cancer, bladder cancer, peritoneal cancer, parathyroid cancer, adrenal gland cancer, paranasal sinus cancer, non-small-cell lung cancer, tongue cancer, astrocytoma, small cell lung cancer, pediatric brain cancer, pediatric lymphoma, pediatric leukemia, small intestine cancer, meningioma, esophageal cancer, neuroglioma, renal pelvic cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urothelial cancer, cancer of unknown primary site, gastric lymphoma, gastric cancer, gastric carcinoid tumors, gastrointestinal stromal cancer, Wilm's cancer, breast cancer, sarcoma, penile cancer, pharynx cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoid tumors, vaginal cancer, spinal cord cancer, acoustic neurinoma, pancreatic cancer, salivary gland cancer, Kaposi's sarcoma, Paget's disease, tonsil cancer, squamous cell cancer, lung adenocarcinoma, lung cancer, lung squamous cell cancer, skin cancer, anal cancer, rhabdomyosarcoma, laryngeal cancer, pleural cancer, blood cancer, and thymus cancer.

In addition, the cancer may be a cancer, which expresses a RET fusion gene.

The RET fusion gene refers to a form in which a RET gene encoding a RET receptor tyrosine kinase is linked to one or more other genes, and genes other than the RET gene including the RET fusion gene may be kinesin family member 5B (KIF5B), coiled-coil domain-containing protein 6 (CCDC6), nuclear receptor coactivator 4 (NCOA4), or tripartite motif containing 33 (TRIM33), and are not limited thereto.

A compound of Chemical Formula 1 according to the present invention exhibits excellent ret proto-oncogene (RET) enzyme inhibitory ability (see Experimental Example 1), and has an excellent effect of inhibiting the proliferation of medullary thyroid cancer cells and lung cancer cells, which express RET fusion genes (see Experimental Example 2), and thus the derivative can be effectively used in the treatment of cancer, for example, medullary thyroid cancer or lung cancer, and particularly, can be effectively used in the treatment of cancer in which RET fusion genes are expressed.

The compound of Chemical Formula 1 or a pharmaceutically acceptable salt thereof may be administered in various oral and parenteral dosage forms at the time of clinical administration, more preferably, a parenteral dosage form. When the compound of Chemical Formula 1 is prepared, the compound is prepared using a diluent or excipient, such as a filler, an extender, a binder, a wetting agent, a disintegrant, and a surfactant, which are commonly used. A solid formulation for oral administration includes a tablet, a pill, a powder, a granule, a capsule, and the like, and the solid formulation is prepared by mixing at least one excipient, for example, starch, calcium carbonate, sucrose or lactose, gelatin, and the like with one or more compounds. Further, in addition to simple excipients, lubricants such as magnesium stearate and talc are also used. A liquid formulation for oral administration corresponds to a suspension, a liquid for internal use, an emulsion, a syrup, and the like, and the liquid formulation may include, in addition to water and liquid paraffin which are simple commonly used diluents, various excipients, for example, a wetting agent, a sweetener, an aromatic, a preservative, and the like. Examples of a formulation for parenteral administration include an aqueous sterile solution, a non-aqueous solvent, a suspension, and an emulsion. As the non-aqueous solvent and the suspension solvent, it is possible to use propylene glycol, polyethylene glycol, a vegetable oil such as olive oil, an injectable ester such as ethyl oleate, and the like.

A pharmaceutical composition comprising the compound of Chemical Formula 1 or the pharmaceutically acceptable salt thereof as an active ingredient may be parenterally administered, and the parenteral administration is performed using an injection method such as subcutaneous injection, intravenous injection, intramuscular injection, or intrathoracic injection.

In this case, in order to formulate the pharmaceutical composition into a formulation for parenteral administration, the pharmaceutical composition may be prepared into a solution or suspension by mixing the compound of Chemical Formula 1 or the pharmaceutically acceptable salt thereof with a stabilizer or buffer in water and the solution or suspension may be prepared in an ampoule or vial unit form for administration. The composition may be sterilized and/or contain an adjuvant such as a preservative, stabilizer, hydrating agent, or an emulsion-promoting agent, a salt and/or buffer for adjusting osmotic pressure, and other therapeutically useful materials, and the composition may be formulated using a typical method such as a mixing, granulating, or coating method.

Examples of a formulation for oral administration include a tablet, a pill, a hard/soft capsule, a solution, a suspension, an emulsion, a syrup, a granule, an elixir, a troche, and the like, and these formulations contain a diluent (for example: lactose, dextrose, sucrose, mannitol, sorbitol, cellulose and/or glycine) and a lubricant (for example: silica, talc, stearic acid, and a magnesium or calcium salt thereof, and/or polyethylene glycol) in addition to an active ingredient.

The tablet may contain a binder such as magnesium aluminum silicate, starch paste, gelatin, methylcellulose, sodium carboxymethylcellulose, and/or polyvinylpyrrolidine, and may contain a disintegrating agent such as starch, agar, alginic acid, or a sodium salt thereof or a boiling mixture, and/or an absorbent, a coloring agent, a flavoring agent, and a sweeting agent in some cases.

A pharmaceutical composition containing the compound of Chemical Formula 1, an optical isomer thereof or a pharmaceutically acceptable salt thereof as an active ingredient for the prevention or treatment of cancer may be administered as a separate therapeutic agent or may be administered in combination with other anti-cancer agents in use.

Still another aspect of the present invention provides a method for preventing or treating cancer, the method comprising administering a pharmaceutical composition containing the compound of Chemical Formula 1, an isomer thereof, a solvate thereof, a hydrate thereof, or a pharmaceutically acceptable salt thereof as an active ingredient to a subject in need thereof.

Yet another object of the present invention is to provide a use of the compound of Chemical Formula 1 or an isomer thereof, a solvate thereof, a hydrate thereof, or a pharmaceutically acceptable salt thereof for use in the preparation of a medicine used for the prevention or treatment of cancer.

Hereinafter, the present invention will be described in detail with reference to Examples and Experimental Examples.

However, the following Examples and Experimental Examples are only for exemplifying the present invention, and the contents of the present invention are not limited by the following Examples and Experimental Examples.

<Analysis and Purification Conditions>

The compounds synthesized in the Examples of the present invention were purified or subjected to structural analysis using the following methods.

1. Medium Pressure Liquid Chromatography (MPLC) for Purification

As a medium pressure liquid chromatography, CombiFlash Rf+UV from TELEDYNE ISCO was used.

2. LC-MS for Analysis (ACQUITY UPLC H-Class Core System)

A device equipped with a QDA detector manufactured by Waters was used for a UPLC system (ACQUITY UPLC PDA Detector) manufactured by Waters. The column used was ACQUITY UPLC BEHC18 (1.7 μm, 2.1×50 mm) from Waters, and the column temperature was 30° C.

Water including 0.1% formic acid was used as a mobile phase A, and acetonitrile including 0.1% formic acid was used as a mobile phase B.

Gradient condition (3 minutes at 10 to 100% B, and movement speed=0.6 ml/min)

3. Prep-150 LC System for Purification (Preparative-Liquid Chromatography UV Spectrometry)

A device manufactured by Waters was used for a Prep 150 LC system manufactured by Waters (2545 Quaternary gradient module, 2998 Photodiode Array Detector, Fraction collector III). The column used was XTERRA Prep RP18 OBD™ (10 μm, 30×300 mm), and the column temperature was room temperature.

Gradient condition (120 minutes at 3 to 100% B, and movement speed=40 ml/min)

4. SFC Conditions for Separation of Chiral Compounds

An 80Q Preparative SFC system manufactured by Waters was used. The column used was CHIRALPAK AS (10 μm, 250×30 mm I.D.) from DAICEL, and the column temperature was room temperature. $CO_2$ as a mobile phase and methanol to which 0.1% aqueous ammonia was added as an auxiliary solvent were used and allowed to flow for 130 minutes.

5. NMR Analysis

NMR analysis was performed using AVANCE III 400 or AVANCE III 400 HD manufactured by Bruker, and data was expressed in parts per million (δ) (ppm).

Commercially available reagents used were used without further purification. In the present invention, room temperature refers to a temperature of about 20 to 25° C. A rotary evaporator was used for concentration under reduced pressure or removal of solvent distillation.

<Example 1> Preparation of 2-(6-(6-((6-methoxy-pyridin-3-yl)methyl)-3,6-diazabicyclo[3.1.1]heptan-3-yl)pyridin-3-yl)-N-(5-methyl-1H-pyrazol-3-yl)furo[3,2-d]pyrimidin-4-amine The title compound was prepared by the method represented by the following Reaction Scheme 1.

[Reaction Scheme 1]

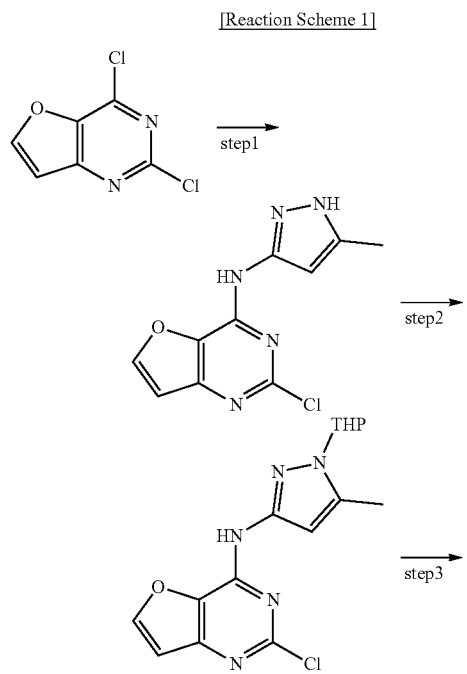

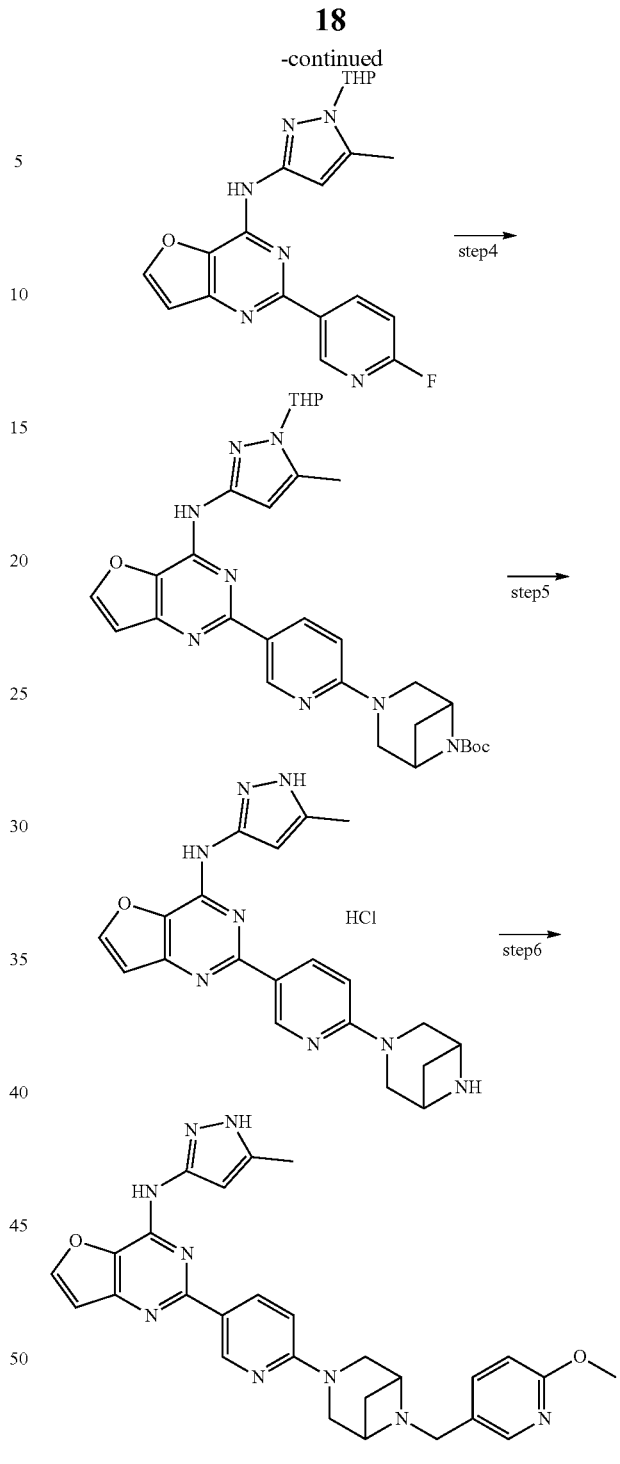

Step 1: Preparation of 2-chloro-N-(5-methyl-1H-pyrazol-3-yl)furo[3,2-d]pyrimidin-4-amine After 2,4-dichlorofuro[3,2-d]pyrimidine (50 g, 264.55 mmol, 1 eq), 5-methyl-1H-pyrazol-3-amine (26.98 g, 277.78 mmol, 1.05 eq), and DIPEA (102.57 g, 793.65 mmol, 138.24 mL, 3 eq) were dissolved in DMSO (250 mL), the resulting solution was stirred at 60° C. for 12 hours. Water was slowly added to the reaction mixture and the resulting solid was filtered. The solid was washed with water, and then recovered to obtain the target compound 2-chloro-N-(5-methyl-1H-pyrazol-3-yl)furo[3,2-d]pyrimidin-4-amine (62 g).

MS (m/z): 250.1 [M+1]⁺

Step 2: Preparation of 2-chloro-N-(5-methyl-1-(tetrahydro-2H-pyran-2-yl)-1H-pyrazol-3-yl)furo[3,2-d]pyrimidin-4-amine After 2-chloro-N-(5-methyl-1H-pyrazol-3-yl)furo[3,2-d]pyrimidin-4-amine (60 g, 240.33 mmol, 1 eq), and TsOH (8.28 g, 48.07 mmol, 0.2 eq) were dissolved in THF (600 mL), 3,4-dihydro-2H-pyran (60.72 g, 721.86 mmol, 66 mL, 3 eq) was added thereto, and the resulting mixture was stirred at 60° C. for 15 hours. An aqueous NaHCO$_3$ solution (500 mL), EtOAc (500 mL), and water (1 L) were added to the reaction mixture, an organic layer was washed with brine (400 mL) after recovering the organic layer, and dried using Na$_2$SO$_4$. The organic layer was filtered, concentrated in a vacuum concentrator, and then purified using medium pressure chromatography (Hexane/EtOAc=4/1 to 2/1). After the purification, the resulting product was concentrated under reduced pressure to obtain the target compound 2-chloro-N-(5-methyl-1-(tetrahydro-2H-pyran-2-yl)-1H-pyrazol-3-yl)furo[3,2-d]pyrimidin-4-amine (60.66 g, 181.74 mmol, 75.62% yield).

MS (m/z): 334.1 [M+1]$^+$ $^1$H NMR (400 MHz, CDCl$_3$) δ=7.77 (d, J=2.0 Hz, 1H), 7.69 (s, 1H), 6.81 (d, J=2.2 Hz, 1H), 6.76 (s, 1H), 5.20 (dd, J=2.8, 10.4 Hz, 1H), 4.12-4.02 (m, 1H), 3.681-3.618 (m, 1H), 2.40-2.32 (m, 4H), 2.14-2.04 (m, 1H), 1.89 (br dd, J=2.8, 13.6 Hz, 1H), 1.77-1.63 (m, 2H), 1.62-1.55 (m, 1H)

Step 3: Preparation of 2-(6-fluoropyridin-3-yl)-N-(5-methyl-1-(tetrahydro-2H-pyran-2-yl)-1H-pyrazol-3-yl)furo[3,2-d]pyrimidin-4-amine After 2-chloro-N-(5-methyl-1-(tetrahydro-2H-pyran-2-yl)-1H-pyrazol-3-yl)furo[3,2-d]pyrimidin-4-amine (20 g, 59.92 mmol, 1 eq), 2-fluoro-5-(4,4,5,5-tetramethyl-1,3,2-dioxaborolan-2-yl)pyridine (16 g, 71.73 mmol, 1.20 eq), and K$_2$CO$_3$ (20.70 g, 149.80 mmol, 2.5 eq) were dissolved in dioxane (400 mL) and water (20 mL), Pd(dppf)Cl$_2$·CH$_2$Cl$_2$ (4.89 g, 5.99 mmol, 0.1 eq) was added thereto. The reaction mixture was stirred under nitrogen gas at 90° C. for 3 hours. After the reaction mixture was filtered, the filtrate was concentrated, and water and EtOAc were added thereto. The organic layer was collected and washed with brine (1.0 L), and then dried using Na$_2$SO$_4$. The organic layer was filtered, concentrated in a vacuum concentrator, and then purified using medium pressure chromatography (Hexane/EtOAc=5/1 to 1/1). After the purification, the resulting product was concentrated under reduced pressure to obtain the target compound 2-(6-fluoropyridin-3-yl)-N-(5-methyl-1-(tetrahydro-2H-pyran-2-yl)-1H-pyrazol-3-yl)furo[3,2-d]pyrimidin-4-amine (22 g, 55.78 mmol, 93.09% yield).

MS (m/z): 395.4 [M+1]$^+$ $^1$H NMR (400 MHz, DMSO-d$_6$) δ=10.49 (s, 1H), 9.10 (d, J=2.4 Hz, 1H), 8.78 (dt, J=2.4, 8.4 Hz, 1H), 8.34 (d, J=2.0 Hz, 1H), 7.30 (dd, J=2.8, 8.4 Hz, 1H), 7.11 (d, J=2.4 Hz, 1H), 6.64 (s, 1H), 5.35 (dd, J=2.4, 9.6 Hz, 1H), 3.91 (br d, J=10.8 Hz, 1H), 3.70-3.58 (m, 1H), 2.37 (s, 3H), 2.34-2.23 (m, 1H), 2.05-1.95 (m, 1H), 1.92-1.82 (m, 1H), 1.75-1.62 (m, 1H), 1.58-1.45 (m, 2H)

Step 4: Preparation of tert-butyl 3-(5-(44(5-methyl-1-(tetrahydro-2H-pyran-2-yl)-1H-pyrazol-3-yl)amino)furo[3,2-d]pyrimidin-2-yl)pyridin-2-yl)-3,6-diazabicyclo[3.1.1]heptane-6-carboxylate After 2-(6-fluoropyridin-3-yl)-N-(5-methyl-1-(tetrahydro-2H-pyran-2-yl)-1H-pyrazol-3-yl)furo[3,2-d]pyrimidin-4-amine (1 g, 2.54 mmol, 1 eq), tert-butyl 3,6-diazabicyclo[3.1.1]heptane-6-carboxylate (700 mg, 3.53 mmol, 1.39 eq), and K$_2$CO$_3$ (2 g, 14.47 mmol, 5.71 eq) were dissolved in DMSO (10 mL), the resulting solution was stirred at 120° C. for 12 hours. Water was added to the reaction mixture and the resulting solid was filtered. Step 4 was repeated 21 times to obtain the target compound tert-butyl 3-(5-(4-((5-methyl-1-(tetrahydro-2H-pyran-2-yl)-1H-pyrazol-3-yl)amino)furo[3,2-d]pyrimidin-2-yl)pyridin-2-yl)-3,6-diazabicyclo[3.1.1]heptane-6-carboxylate (22.5 g, 37.82 mmol, 71.02% yield).

MS (m/z): 573.1 [M+1]$^+$ $^1$H NMR (400 MHz, DMSO-d$_6$) δ=10.29 (s, 1H), 9.08 (br s, 1H), 8.43 (br d, J=8.4 Hz, 1H), 8.27 (br s, 1H), 7.04 (s, 1H), 6.74 (br d, J=8.8 Hz, 1H), 6.68 (s, 1H), 5.35 (br d, J=9.2 Hz, 1H), 4.21 (br d, J=5.2 Hz, 2H), 4.05 (br s, 2H), 3.92 (br d, J=10.4 Hz, 1H), 3.66 (br d, J=7.2 Hz, 1H), 3.48 (br d, J=11.2 Hz, 2H), 2.55 (br d, J=7.2 Hz, 1H), 2.38 (s, 3H), 2.33-2.24 (m, 1H), 2.05-1.96 (m, 1H), 1.87 (br d, J=12.0 Hz, 1H), 1.76-1.61 (m, 1H), 1.58-1.43 (m, 3H), 1.26 (s, 9H)

Step 5: Preparation of 2-(6-(3,6-diazabicyclo[3.1.1]heptan-3-yl)pyridin-3-yl)-N-(5-methyl1H-pyrazol-3-yl)furo[3,2-d]pyrimidin-4-amine dihydrochloride After tert-butyl 3-(5-(4-((5-methyl-1-(tetrahydro-2H-pyran-2-yl)-1H-pyrazol-3-yl)amino)furo[3,2-d]pyrimidin-2-yl)pyridin-2-yl)-3,6-diazabicyclo[3.1.1]heptane-6-carboxylate (22 g, 36.98 mmol, 1 eq) was dissolved in 4M HCl/MeOH (250 ml), the resulting solution was stirred at room temperature for 1 hour. After the reaction mixture was concentrated under reduced pressure, acetone (1 L) was added thereto. The resulting sold was filtered, recovered, and then dried to obtain the target compound 2-(6-(3,6-diazabicyclo[3.1.1]heptan-3-yl)pyridin-3-yl)-N-(5-methyl-1H-pyrazol-3-yl)furo[3,2-d]pyrimidin-4-amine dihydrochloride (22.4 g).

MS (m/z): 389.1 [M+1]$^+$ $^1$H NMR (400 MHz, DMSO-d$_6$) δ=11.56 (br s, 1H), 10.61 (br s, 1H), 9.23 (br s, 1H), 9.03 (s, 1H), 8.76 (dd, J=2.0, 9.2 Hz, 1H), 8.50 (d, J=2.0 Hz, 1H), 7.26 (br d, J=9.2 Hz, 1H), 7.20 (d, J=2.0 Hz, 1H), 6.57 (s, 1H), 4.56 (br s, 2H), 4.19 (br s, 4H), 3.01-2.95 (m, 1H), 2.39 (s, 3H), 1.94 (br dd, J=5.6, 10.0 Hz, 1H)

Step 6: Preparation of 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)furo[3,2-d]pyrimidin-4-amine After 2-(6-(3,6-diazabicyclo[3.1.1]heptan-3-yl)pyridin-3-yl)-N-(5-methyl-1H-pyrazol-3-yl)furo[3,2-d]pyrimidin-4-amine dihydrochloride (22.4 g, 48.55 mmol), 6-methoxypyridine-3-carbaldehyde (9.99 g, 72.83 mmol, 1.5 eq), and TEA (39.31 g, 388.43 mmol, 54.06 mL, 8 eq) were dissolved in DMA (250 ml), NaBH(OAc)$_3$ (30.87 g, 145.66 mmol, 3 eq) was added thereto, and the resulting mixture was stirred at 55° C. for 5 hours. Water (1 L) and EtOAc (1.6 L) were added to the reaction mixture and the organic layer was recovered. The organic layer was washed with brine (800 ml), and then dried using Na$_2$SO$_4$. The organic layer was filtered, concentrated by a vacuum concentrator, and then purified using RP-HPLC to obtain the target compound 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)furo[3,2-d]pyrimidin-4-amine (11.7 g, 22.96 mmol, 47.29% yield).

MS (m/z): 510.4 [M+1]$^+$

¹H NMR (400 MHz, DMSO-d₆) δ=12.11 (br s, 1H), 10.14 (br s, 1H), 9.13 (d, J=2.0 Hz, 1H), 8.46 (dd, J=2.0, 8.8 Hz, 1H), 8.26 (s, 1H), 8.07 (d, J=2.0 Hz, 1H), 7.67 (dd, J=2.4, 8.8 Hz, 1H), 7.05 (s, 1H), 6.76 (dd, J=6.0, 8.8 Hz, 2H), 6.61 (br s, 1H), 3.82 (s, 3H), 3.75 (br d, J=12.0 Hz, 2H), 3.66 (br d, J=5.6 Hz, 2H), 3.61-3.42 (m, 4H), 2.54-2.51 (m, 1H), 2.31 (s, 3H), 1.56 (br d, J=8.4 Hz, 1H)

All Example compounds (compounds of Examples 1 to 37) were prepared in a manner similar to Example 1, and the compound names, chemical structural formulae, NMR and LC-MS analysis results of each Example compound were summarized and are shown in the following Table 1.

TABLE 1

| Example compound | Structure | Name of compound | ¹H NMR | LC-MS (m/z) |
|---|---|---|---|---|
| 1 | 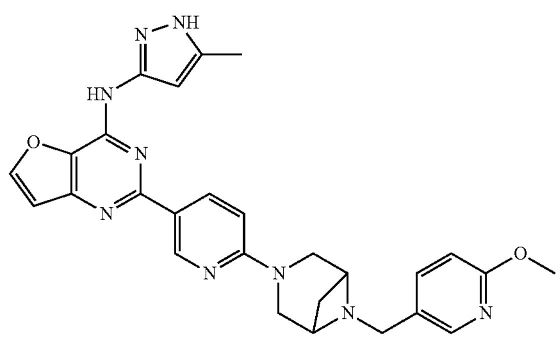 [SMILES: COc1ccc(CN2C3CC2CN(c2ccc(-c4nc(Nc5cc(C)[nH]n5)c5occc5n4)cn2)C3)cn1] | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)furo[3,2-d]pyrimidin-4-amine | ¹H NMR (400 MHz, DMSO-d₆) δ = 12.11 (br s, 1H), 10.14 (br s, 1H), 9.13 (d, J = 2.0 Hz, 1H), 8.46 (dd, J = 2.0, 8.8 Hz, 1H), 8.26 (s, 1H), 8.07 (d, J = 2.0 Hz, 1H), 7.67 (dd, J = 2.4, 8.8 Hz, 1H), 7.05 (s, 1H), 6.76 (dd, J = 6.0, 8.8 Hz, 2H), 6.61 (br s, 1H), 3.82 (s, 3H), 3.75 (br d, J = 12.0 Hz, 2H), 3.66 (br d, J = 5.6 Hz, 2H), 3.61-3.42 (m, 4H), 2.54-2.51 (m, 1H), 2.31 (s, 3H), 1.56 (br d, J = 8.4 Hz, 1H) | 510.4 [M + H]⁺ |
| 2 | 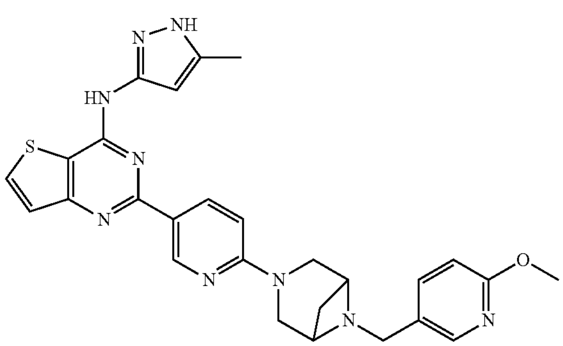 | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)thieno[3,2-d]pyrimidin-4-amine | ¹H NMR (400 MHz, DMSO-d₆) δ = 11.52 (s, 1H), 9.23 (d, J = 2.2 Hz, 1H), 8.71 (dd, J = 9.2, 2.3 Hz, 1H), 8.43 (d, J = 5.5 Hz, 2H), 8.07 (ddd, J = 8.3, 5.6, 2.4 Hz, 1H), 7.76 (d, J = 5.5 Hz, 1H), 7.02 (d, J = 9.3 Hz, 1H), 6.92 (d, J = 7.0 Hz, 1H), 6.47 (s, 1H), 4.62 (dd, J = 23.4, 5.9 Hz, 2H), 4.48-4.42 (m, 2H), 4.26 (s, 2H), 4.15 (s, 2H), 3.89 (s, 3H), 2.35 (s, 3H) | 526.3 [M + H]⁺ |
| 3 | 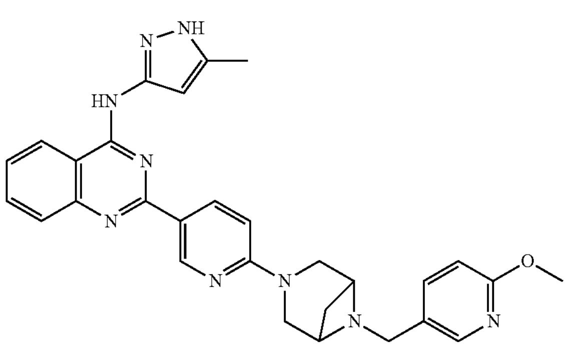 [SMILES: COc1ccc(CN2C3CC2CN(c2ccc(-c4nc(Nc5cc(C)[nH]n5)c5ccccc5n4)cn2)C3)cn1] | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d₆) δ = 12.23 (br s, 1H), 10.29 (br s, 1H), 9.24 (d, J = 2.0 Hz, 1H), 8.67-8.49 (m, 2H), 8.06 (s, 1H), 7.77 (br d, J = 2.0 Hz, 2H), 7.65 (br d, J = 8.4 Hz, 1H), 7.52-7.41 (m, 1H), 6.84-6.68 (m, 3H), 3.81 (s, 3H), 3.75 (br d, J = 11.2 Hz, 2H), 3.64 (br d, J = 5.6 Hz, 2H), 3.60-3.45 (m, 4H), 2.53-2.51 (m, 1H), 2.35 (s, 3H), 1.55 (br d, J = 8.4 Hz, 1H) | 520.3 [M + H]⁺ |

TABLE 1-continued

| Example compound | Name of compound | $^1$H NMR | LC-MS (m/z) |
|---|---|---|---|
| 4 | 2-(6-(6-((6-methoxypyridin-3-yl)methyl)-3,6-diazabicyclo[3.1.1]heptan-3-yl)pyridin-3-yl)-N-(5-(trifluoromethyl)-1H-pyrazol-3-yl)furo[3,2-d]pyrimidin-4-amine | $^1$H NMR (400 MHz, DMSO-d$_6$) δ = 9.11 (d, J = 2.4 Hz, 1H), 8.65 (d, J = 2.2 Hz, 1H), 8.45 (d, J = 9.1 Hz, 1H), 8.07 (s, 1H), 7.95 (s, 2H), 7.68 (d, J = 8.7 Hz, 1H), 7.32 (d, J = 2.1 Hz, 1H), 7.25 (s, 2H), 6.86 (d, J = 9.0 Hz, 1H), 6.77 (d, J = 8.4 Hz, 1H), 6.67 (s, 1H), 3.82 (s, 3H), 3.81-3.79 (m, 2H), 3.78-3.74 (m, 2H), 3.68 (dd, J = 6.0, 1.8 Hz, 2H), 2.69-2.66 (m, 1H), 1.47 (d, J = 6.9 Hz, 1H) | 564.3 [M + H]$^+$ |
| 5 | N-(5-methyl-1H-pyrazol-3-yl)-2-(6-(6-((5-methylthiazol-2-yl)methyl)-3,6-diazabicyclo[3.1.1]heptan-3-yl)pyridin-3-yl)quinazolin-4-amine | $^1$H NMR (400 MHz, DMSO-d$_6$) δ = 10.34 (s, 1H), 9.23 (d, J = 2.2 Hz, 1H), 8.64-8.51 (m, 2H), 7.83-7.72 (m, 2H), 7.47 (ddd, J = 8.2, 6.0, 2.2 Hz, 1H), 7.35 (d, J = 1.2 Hz, 1H), 6.80 (d, J = 9.0 Hz, 1H), 6.73 (s, 1H), 3.81-3.73 (m, 6H), 3.60 (d, J = 11.7 Hz, 2H), 2.56 (dd, J = 11.6, 3.6 Hz, 1H), 2.41 (d, J = 1.0 Hz, 3H), 2.35 (s, 3H), 1.62 (d, J = 8.5 Hz, 1H) | 510.4 [M + H]$^+$ |
| 6 | 2-(6-(3-((6-methoxypyridin-3-yl)methyl)-3,6-diazabicyclo[3.1.1]heptan-6-yl)pyridin-3-yl)-N-(5-methyl-1H-pyrazol-3-yl)quinazolin-4-amine | $^1$H NMR (400 MHz, DMSO-d$_6$) δ = 11.91 (s, 1H), 10.32 (s, 1H), 9.24 (d, J = 2.1 Hz, 1H), 8.61 (d, J = 8.3 Hz, 1H), 8.57 (dd, J = 8.9, 2.2 Hz, 1H), 7.78 (dd, J = 4.6, 1.1 Hz, 2H), 7.60 (d, J = 6.9 Hz, 1H), 7.48 (d, J = 6.2 Hz, 1H), 6.80 (d, J = 9.0 Hz, 1H), 6.73 (s, 1H), 6.37 (s, 1H), 6.20 (dd, J = 6.9, 1.4 Hz, 1H), 4.53 (d, J = 6.1 Hz, 1H), 4.00 (dd, J = 34.3, 12.5 Hz, 2H), 3.78 (d, J = 22.3 Hz, 2H), 3.73 (s, 2H), 3.62 (dd, J = 13.2, 6.6 Hz, 2H), 2.63 (s, 1H), 2.35 (s, 3H), 1.64 (d, J = 6.9 Hz, 1H) | 520.4 [M + H]$^+$ |
| 7 | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)-6,7-dihydro-5H-cyclopenta[d]pyrimidin-4-amine | $^1$H NMR (400 MHz, DMSO-d6) δ 10.90 (s, 1H), 9.19 (dd, J = 22.3, 2.5 Hz, 1H), 8.67 (dd, J = 24.6, 9.5 Hz, 1H), 8.46 (dd, J = 36.6, 2.5 Hz, 1H), 8.14-8.02 (m, 1H), 7.05 (dd, J = 42.7, 9.4 Hz, 1H), 6.91 (dd, J = 8.6, 7.2 Hz, 1H), 6.51 (d, J = 4.7 Hz, 1H), 4.64 (d, J = 6.1 Hz, 1H), 4.56 (d, J = 6.2 Hz, 1H), 4.44 (d, J = 6.4 Hz, 2H), 4.26-4.05 (m, 6H), 3.88 (d, J = 6.8 Hz, 3H), 3.13 (q, J = 7.8 Hz, 2H), 2.88 (s, 2H), 2.33 (d, J = 5.6 Hz, 3H), 2.16 (s, 2H) | 510.3 [M + H]$^+$ |

TABLE 1-continued

| Example compound | Structure | Name of compound | ¹H NMR | LC-MS (m/z) |
|---|---|---|---|---|
| 8 | 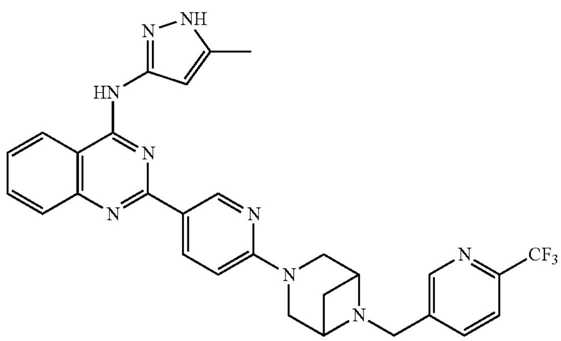 [SMILES: Cc1cc(Nc2nc(-c3ccc(N4CC5CC(C4)N5Cc4ccc(C(F)(F)F)nc4)nc3)nc3ccccc23)n[nH]1] | N-(5-methyl-1H-pyrazol-3-yl)-2-(6-(6-((6-(trifluoromethyl)pyridin-3-yl)methyl)-3,6-diazabicyclo[3.1.1]heptan-3-yl)pyridin-3-yl)quinazolin-4-amine | ¹H NMR (400 MHz, DMSO-d6) δ 12.22 (s, 1H), 10.30 (s, 1H), 9.24 (d, J = 2.3 Hz, 1H), 8.75 (d, J = 2.1 Hz, 1H), 8.62-8.54 (m, 2H), 8.06 (dd, J = 8.0, 2.1 Hz, 1H), 7.84 (d, J = 8.0 Hz, 1H), 7.79-7.74 (m, 2H), 7.47 (ddd, J = 8.3, 6.1, 2.1 Hz, 1H), 6.82 (d, J = 9.0 Hz, 1H), 6.73 (s, 1H), 3.79-3.59 (m, 8H), 2.58 (d, J = 7.0 Hz, 1H), 2.34 (s, 3H), 1.62 (d, J = 8.4 Hz, 1H) | 558.5 [M + H]⁺ |
| 9 | 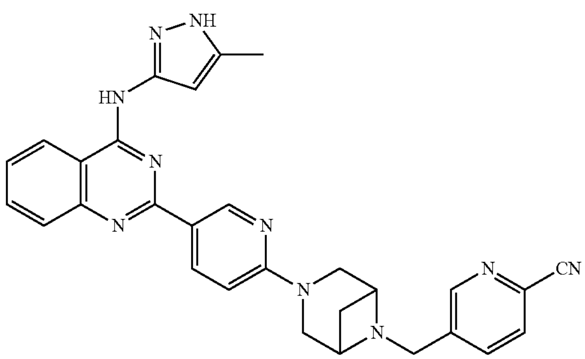 [SMILES: Cc1cc(Nc2nc(-c3ccc(N4CC5CC(C4)N5Cc4ccc(C#N)nc4)nc3)nc3ccccc23)n[nH]1] | 5-((3-(5-(4-((5-methyl-1H-pyrazol-3-yl)amino)quinazolin-2-yl)pyridin-2-yl)-3,6-diazabicyclo[3.1.1]heptan-6-yl)methyl)picolinonitrile | ¹H NMR (400 MHz, DMSO-d6) δ 12.22 (s, 1H), 10.30 (s, 1H), 9.23 (d, J = 2.3 Hz, 1H), 8.74 (dd, J = 2.1, 0.9 Hz, 1H), 8.62-8.54 (m, 2H), 8.05-7.95 (m, 2H), 7.81-7.74 (m, 2H), 7.47 (dd, J = 8.3, 6.2, 2.0 Hz, 1H), 6.81 (d, J = 9.0 Hz, 1H), 6.73 (s, 1H), 3.81-3.56 (m, 8H), 2.58 (d, J = 7.0 Hz, 1H), 2.34 (s, 3H), 1.61 (d, J = 8.4 Hz, 1H) | 515.5 [M + H]⁺ |
| 10 | 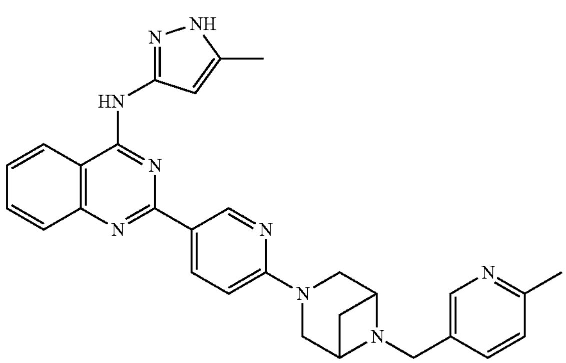 [SMILES: Cc1ccc(CN2C3CC2CN(c2ccc(-c4nc(Nc5cc(C)[nH]n5)c5ccccc5n4)cn2)C3)cn1] | N-(5-methyl-1H-pyrazol-3-yl)-2-(6-(6-((6-methylpyridin-3-yl)methyl)-3,6-diazabicyclo[3.1.1]heptan-3-yl)pyridin-3-yl)quinazolin-4-amine | ¹H NMR (400 MHz, DMSO-d6) δ 12.22 (s, 1H), 10.30 (s, 1H), 9.23 (d, J = 2.3 Hz, 1H), 8.62-8.54 (m, 2H), 8.38 (d, J = 2.3 Hz, 1H), 7.81-7.74 (m, 2H), 7.63 (dd, J = 7.9, 2.3 Hz, 1H), 7.47 (ddd, J = 8.3, 6.1, 2.1 Hz, 1H), 7.18 (d, J = 7.8 Hz, 1H), 6.81 (d, J = 9.0 Hz, 1H), 6.73 (s, 1H), 3.77 (d, J = 12.2 Hz, 2H), 3.69 (d, J = 5.9 Hz, 2H), 3.58 (d, J = 25.7 Hz, 4H), 2.43 (s, 3H), 2.41 (d, J = 3.5 Hz, 1H), 2.35 (s, 3H), 1.59 (d, J = 8.4 Hz, 1H) | 504.5 [M + H]⁺ |
| 11 | 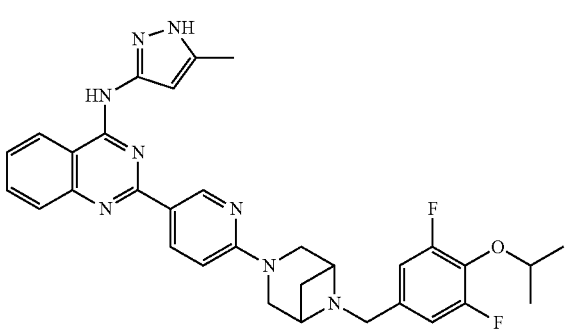 [SMILES: Cc1cc(Nc2nc(-c3ccc(N4CC5CC(C4)N5Cc4cc(F)c(OC(C)C)c(F)c4)nc3)nc3ccccc23)n[nH]1] | 2-(6-(6-(3,5-difluoro-4-isopropoxybenzyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d6) δ 12.19 (s, 1H), 10.30 (s, 1H), 9.23 (d, J = 2.3 Hz, 1H), 8.63-8.53 (m, 2H), 7.81-7.74 (m, 2H), 7.47 (ddd, J = 8.3, 6.1, 2.1 Hz, 1H), 7.15-7.08 (m, 2H), 6.80 (d, J = 9.0 Hz, 1H), 6.73 (s, 1H), 4.32 (hept, J = 6.1 Hz, 1H), 3.72 (d, J = 6.0 Hz, 4H), 3.53 (s, 2H), 3.33 (s, 2H), 2.57 (d, J = 6.9 Hz, 1H), 2.34 (s, 3H), 1.59 (d, J = 8.4 Hz, 1H), 1.26 (d, J = 6.1 Hz, 6H) | 583.5 [M + H]⁺ |

TABLE 1-continued

| Example compound | Structure | Name of compound | ¹H NMR | LC-MS (m/z) |
|---|---|---|---|---|
| 12 | 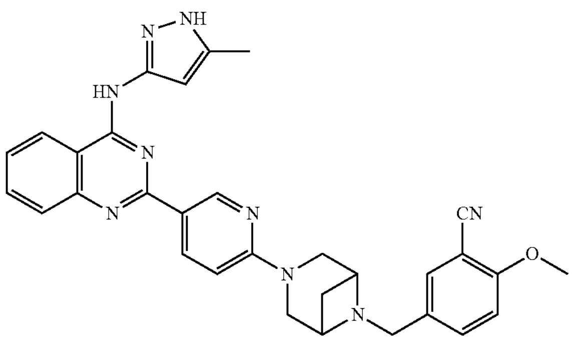 [SMILES: COc1ccc(CN2C3CC2CN(c2ccc(-c4nc(Nc5cc(C)[nH]n5)c5ccccc5n4)cn2)C3)cc1C#N] | 2-methoxy-5-((3-(5-(4-((5-methyl-1H-pyrazol-3-yl)amino)quinazolin-2-yl)pyridin-2-yl)-3,6-diazabicyclo[3.1.1]heptan-6-yl)methyl)benzonitrile | ¹H NMR (400 MHz, DMSO-d6) δ 12.21 (s, 1H), 10.30 (s, 1H), 9.23 (d, J = 2.3 Hz, 1H), 8.64-8.52 (m, 2H), 7.81-7.73 (m, 2H), 7.68-7.61 (m, 2H), 7.47 (ddd, J = 8.3, 6.1, 2.1 Hz, 1H), 7.18 (d, J = 8.6 Hz, 1H), 6.81 (d, J = 8.9 Hz, 1H), 6.73 (s, 1H), 3.89 (s, 3H), 3.75 (d, J = 12.1 Hz, 2H), 3.68 (d, J = 5.9 Hz, 2H), 3.33 (s, 2H), 2.58-2.53 (m, 1H), 2.35 (s, 3H), 1.58 (d, J = 8.4 Hz, 1H) | 544.5 [M + H]⁺ |
| 13 | 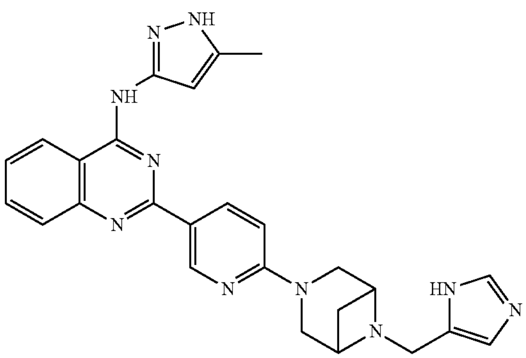 [SMILES: Cc1cc(Nc2nc(-c3ccc(N4CC5CC(C4)N5Cc4cnc[nH]4)nc3)nc3ccccc23)n[nH]1] | 2-(6-(6-((1H-imidazol-5-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, MeOD) δ = 9.19 (d, J = 2.1 Hz, 1H), 8.55 (dd, J = 9.0, 2.2 Hz, 1H), 8.26 (d, J = 8.2 Hz, 1H), 7.84-7.75 (m, 3H), 7.54-7.47 (m, 1H), 7.25 (s, 1H), 6.80 (d, J = 9.0 Hz, 1H), 6.68 (s, 1H), 4.46-4.10 (m, 3H), 4.06-3.95 (m, 5H), 2.39 (s, 3H) | 479.4 [M + H]⁺ |
| 14 | 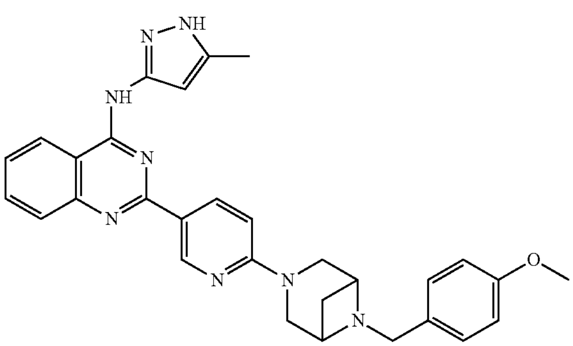 [SMILES: COc1ccc(CN2C3CC2CN(c2ccc(-c4nc(Nc5cc(C)[nH]n5)c5ccccc5n4)cn2)C3)cc1] | 2-(6-(6-(4-methoxybenzyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d₆) δ = 10.54 (s, 1H), 9.25 (d, J = 2.2 Hz, 1H), 8.64 (d, J = 8.2 Hz, 1H), 8.57 (dd, J = 8.9, 2.3 Hz, 1H), 7.81-7.74 (m, 2H), 7.47 (ddd, J = 8.2, 5.8, 2.3 Hz, 1H), 7.24 (d, J = 8.6 Hz, 2H), 6.86 (d, J = 8.7 Hz, 2H), 6.80 (d, J = 9.0 Hz, 1H), 6.74 (s, 1H), 3.76 (d, J = 2.5 Hz, 1H), 3.72 (s, 3H), 3.65 (d, J = 5.9 Hz, 2H), 3.57 (s, 2H), 3.48 (s, 2H), 2.54 (d, J = 2.7 Hz, 1H), 2.34 (s, 3H), 1.83 (s, 2H), 1.57 (d, J = 8.4 Hz, 1H) | 519.4 [M + H]⁺ |
| 15 | 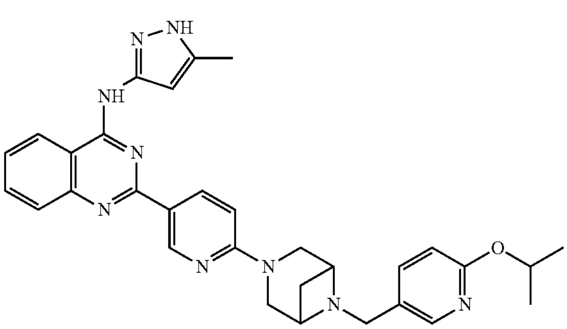 [SMILES: Cc1cc(Nc2nc(-c3ccc(N4CC5CC(C4)N5Cc4ccc(OC(C)C)nc4)nc3)nc3ccccc23)n[nH]1] | 2-(6-(6-((6-isopropoxypyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, MeOD) δ = 9.20 (s, 1H), 8.55 (d, J = 8.4 Hz, 1H), 8.25 (d, J = 7.4 Hz, 1H), 8.09 (s, 1H), 7.83-7.73 (m, 2H), 7.68 (d, J = 7.7 Hz, 1H), 7.49 (t, J = 7.0 Hz, 1H), 6.78 (d, J = 8.9 Hz, 1H), 6.71 (d, J = 8.4 Hz, 2H), 5.20 (dt, J = 12.3, 6.1 Hz, 1H), 3.93 (d, J = 12.8 Hz, 4H), 3.76 (s, 4H), 2.38 (s, 3H), 1.32 (d, J = 6.2 Hz, 6H) | 548.4 [M + H]⁺ |

TABLE 1-continued

| Example compound | Structure | Name of compound | ¹H NMR | LC-MS (m/z) |
|---|---|---|---|---|
| 16 | 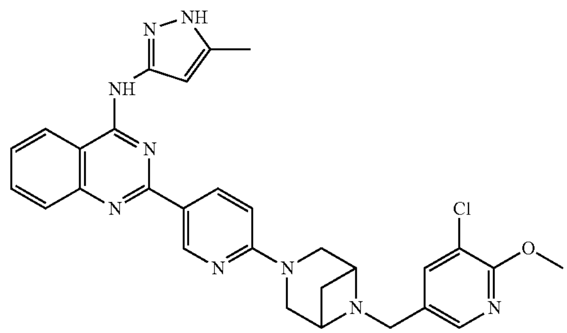 [SMILES: COc1ncc(CN2C3CC2CN(c2ccc(-c4nc(Nc5cc(C)[nH]n5)c5ccccc5n4)cn2)C3)cc1Cl] | 2-(6-(6-((5-chloro-6-methoxypyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d₆) δ = 10.47 (s, 1H), 9.23 (s, 1H), 8.59 (dd, J = 25.6, 8.5 Hz, 2H), 8.08 (s, 1H), 7.86 (s, 1H), 7.77 (t, J = 7.3 Hz, 2H), 7.47 (t, J = 6.6 Hz, 1H), 6.82 (d, J = 8.9 Hz, 1H), 6.72 (s, 1H), 3.92 (s, 3H), 3.77 (d, J = 11.4 Hz, 2H), 3.70 (d, J = 5.3 Hz, 2H), 3.60 (d, J = 16.5 Hz, 2H), 3.53 (s, 2H), 2.57-2.52 (m, 1H), 2.33 (s, 3H), 1.58 (d, J = 8.1 Hz, 1H) | 555.4 [M + H]⁺ |
| 17 | 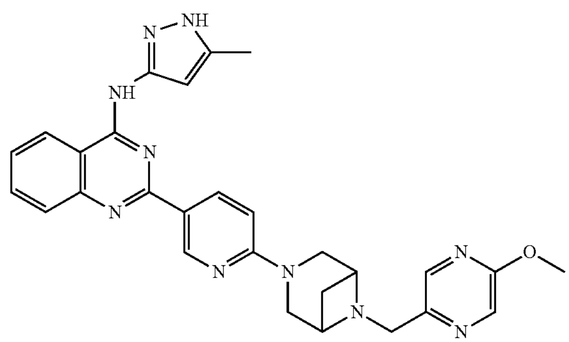 [SMILES: COc1cnc(CN2C3CC2CN(c2ccc(-c4nc(Nc5cc(C)[nH]n5)c5ccccc5n4)cn2)C3)cn1] | 2-(6-(6-((5-methoxypyrazin-2-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, MeOD) δ = 9.18 (d, J = 1.8 Hz, 1H), 8.52 (dd, J = 8.9, 1.8 Hz, 1H), 8.23 (d, J = 8.1 Hz, 1H), 8.13 (d, J = 2.8 Hz, 2H), 7.82-7.73 (m, 2H), 7.48 (t, J = 7.0 Hz, 1H), 6.75 (d, J = 9.0 Hz, 1H), 6.69 (s, 1H), 3.98 (d, J = 12.2 Hz, 2H), 3.94 (s, 3H), 3.90 (d, J = 5.4 Hz, 2H), 3.75 (s, 2H), 3.67 (d, J = 11.9 Hz, 2H), 2.72 (s, 1H), 2.38 (s, 3H), 1.71 (d, J = 9.0 Hz, 1H) | 521.4 [M + H]⁺ |
| 18 | 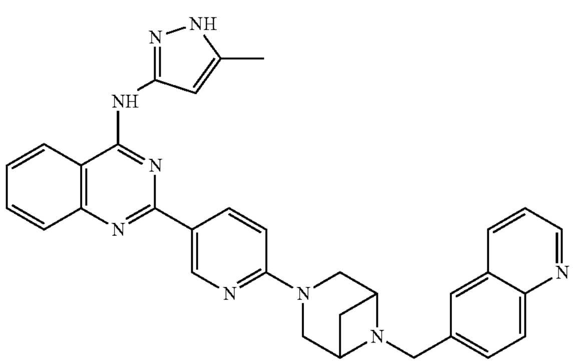 [SMILES: Cc1cc(Nc2nc(-c3ccc(N4CC5CC(C4)N5Cc4ccc5ncccc5c4)nc3)nc3ccccc23)n[nH]1] | N-(5-methyl-1H-pyrazol-3-yl)-2-(6-(6-(quinolin-6-ylmethyl)-3,6-diazabicyclo[3.1.1]heptan-3-yl)pyridin-3-yl)quinazolin-4-amine | ¹H NMR (400 MHz, DMSO-d₆) δ = 11.97 (s, 1H), 10.31 (s, 1H), 9.26 (d, J = 2.1 Hz, 1H), 8.86 (dd, J = 4.1, 1.6 Hz, 1H), 8.64-8.55 (m, 2H), 8.34 (d, J = 7.6 Hz, 1H), 7.96 (d, J = 8.7 Hz, 1H), 7.91 (s, 1H), 7.77 (dd, J = 10.3, 3.7 Hz, 3H), 7.53-7.44 (m, 2H), 6.83 (d, J = 9.0 Hz, 1H), 6.74 (s, 1H), 3.82 (d, J = 11.4 Hz, 2H), 3.76 (d, J = 5.8 Hz, 4H), 3.61 (d, J = 8.8 Hz, 2H), 2.60 (dd, J = 12.9, 6.3 Hz, 1H), 2.35 (s, 3H), 1.62 (d, J = 8.4 Hz, 1H) | 540.4 [M + H]⁺ |
| 19 | 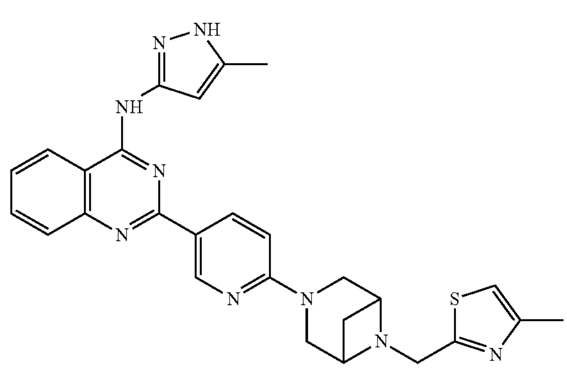 [SMILES: Cc1csc(CN2C3CC2CN(c2ccc(-c4nc(Nc5cc(C)[nH]n5)c5ccccc5n4)cn2)C3)n1] | N-(5-methyl-1H-pyrazol-3-yl)-2-(6-(6-((4-methylthiazol-2-yl)methyl)-3,6-diazabicyclo[3.1.1]heptan-3-yl)pyridin-3-yl)quinazolin-4-amine | ¹H NMR (400 MHz, DMSO-d₆) δ = 10.46 (s, 1H), 9.24 (d, J = 2.2 Hz, 1H), 8.62 (d, J = 8.3 Hz, 1H), 8.57 (dd, J = 8.9, 2.3 Hz, 1H), 7.82-7.74 (m, 2H), 7.47 (ddd, J = 8.2, 6.0, 2.2 Hz, 1H), 7.15 (t, J = 0.9 Hz, 1H), 6.81 (d, J = 9.0 Hz, 1H), 6.73 (s, 1H), 3.83-3.72 (m, 6H), 3.61 (d, J = 11.4 Hz, 2H), 2.59 (dd, J = 13.5, 6.4 Hz, 1H), 2.34 (s, 3H), 2.30 (d, J = 0.7 Hz, 3H), 1.62 (d, J = 8.6 Hz, 1H) | 510.4 [M + H]⁺ |

TABLE 1-continued

| Example compound | Structure | Name of compound | ¹H NMR | LC-MS (m/z) |
|---|---|---|---|---|
| 20 | 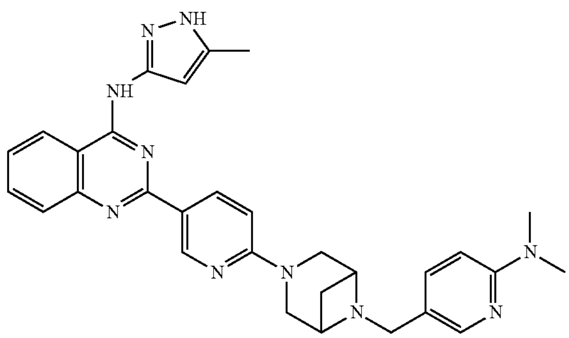 [SMILES: Cc1cc(Nc2nc(-c3ccc(N4CC5CC(C4)N5Cc4ccc(N(C)C)nc4)nc3)nc3ccccc23)n[nH]1] | 2-(6-(6-((6-(dimethylamino)pyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d$_6$) δ = 11.49 (s, 1H), 9.63 (s, 1H), 9.19 (s, 1H), 8.75 (d, J = 7.4 Hz, 1H), 8.55 (d, J = 8.9 Hz, 1H), 8.28 (s, 1H), 7.98 (d, J = 5.4 Hz, 2H), 7.81 (d, J = 9.5 Hz, 1H), 7.68 (t, J = 6.6 Hz, 1H), 6.93 (dd, J = 17.3, 8.9 Hz, 2H), 6.67 (s, 1H), 4.59 (s, 2H), 4.47 (d, J = 5.6 Hz, 2H), 4.17 (d, J = 8.8 Hz, 2H), 3.99 (d, J = 12.8 Hz, 2H), 3.52 (d, J = 5.0 Hz, 1H), 3.12 (s, 6H), 2.36 (s, 3H), 2.07-2.01 (m, 1H) | 533.4 [M + H]⁺ |
| 21 | 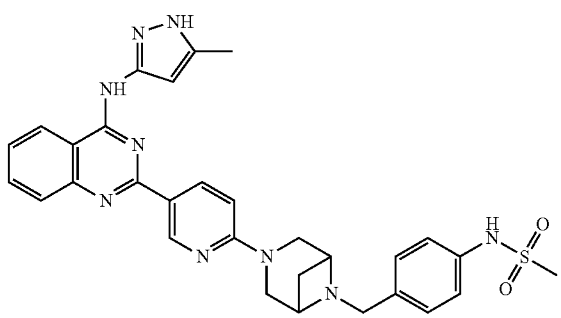 [SMILES: Cc1cc(Nc2nc(-c3ccc(N4CC5CC(C4)N5Cc4ccc(NS(C)(=O)=O)cc4)nc3)nc3ccccc23)n[nH]1] | N-(4-((3-(5-(4-((5-methyl-1H-pyrazol-3-yl)amino)quinazolin-2-yl)pyridin-2-yl)-3,6-diazabicyclo[3.1.1]heptan-6-yl)methyl)phenyl)methanesulfonamide | ¹H NMR (400 MHz, DMSO-d$_6$) δ = 11.25 (s, 1H), 10.03 (s, 1H), 9.60 (s, 1H), 9.20 (d, J = 1.8 Hz, 1H), 8.73 (s, 1H), 8.56 (dd, J = 9.1, 2.0 Hz, 1H), 7.94 (s, 2H), 7.64 (d, J = 6.4 Hz, 1H), 7.54 (d, J = 8.4 Hz, 2H), 7.27 (s, 2H), 6.93 (d, J = 9.1 Hz, 1H), 6.67 (s, 1H), 4.64 (d, J = 5.5 Hz, 2H), 4.46 (d, J = 6.0 Hz, 2H), 4.15 (d, J = 10.1 Hz, 2H), 3.98 (d, J = 12.8 Hz, 2H), 3.05 (s, 3H), 2.35 (s, 3H), 2.04 (d, J = 7.8 Hz, 1H) | 582.4 [M + H]⁺ |
| 22 | 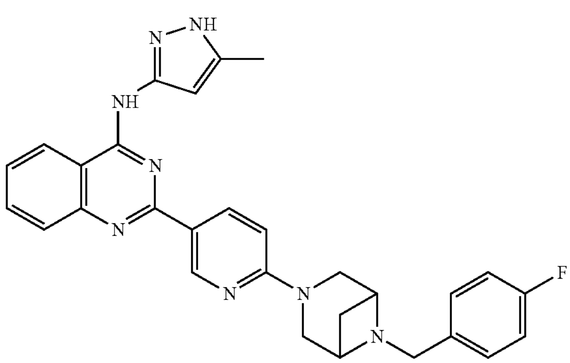 [SMILES: Cc1cc(Nc2nc(-c3ccc(N4CC5CC(C4)N5Cc4ccc(F)cc4)nc3)nc3ccccc23)n[nH]1] | 2-(6-(6-(4-fluorobenzyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d$_6$) δ = 11.90 (s, 1H), 10.31 (s, 1H), 9.25 (d, J = 2.2 Hz, 1H), 8.65-8.52 (m, 2H), 7.78 (d, J = 6.0 Hz, 2H), 7.47 (ddd, J = 8.2, 5.9, 2.3 Hz, 1H), 7.39 (dd, J = 8.3, 5.8 Hz, 2H), 7.13 (t, J = 8.8 Hz, 2H), 6.80 (d, J = 9.0 Hz, 1H), 6.74 (s, 1H), 3.76 (d, J = 13.7 Hz, 4H), 3.60 (s, 4H), 2.58 (s, 1H), 2.35 (s, 3H), 1.61 (d, J = 8.4 Hz, 1H) | 507.5 [M + H]⁺ |
| 23 | 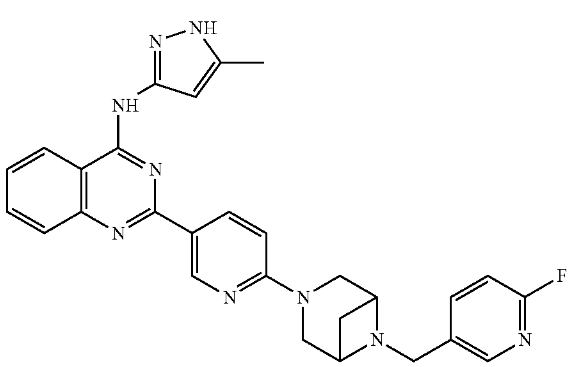 [SMILES: Cc1cc(Nc2nc(-c3ccc(N4CC5CC(C4)N5Cc4ccc(F)nc4)nc3)nc3ccccc23)n[nH]1] | 2-(6-(6-((6-fluoropyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d$_6$) δ = 11.93 (s, 1H), 10.31 (s, 1H), 9.25 (d, J = 2.2 Hz, 1H), 8.63-8.53 (m, 2H), 8.19 (s, 1H), 7.96 (td, J = 8.3, 2.4 Hz, 1H), 7.78 (t, J = 6.1 Hz, 2H), 7.48 (ddd, J = 8.2, 5.8, 2.3 Hz, 1H), 7.12 (dd, J = 8.4, 2.8 Hz, 1H), 6.81 (d, J = 9.0 Hz, 1H), 6.74 (s, 1H), 3.75 (dd, J = 22.7, 8.8 Hz, 4H), 3.61 (s, 4H), 2.56 (d, J = 5.7 Hz, 1H), 2.34 (d, J = 9.2 Hz, 3H), 1.60 (d, J = 8.4 Hz, 1H) | 508.4 [M + H]⁺ |

TABLE 1-continued

| Example compound | Structure | Name of compound | $^1$H NMR | LC-MS (m/z) |
|---|---|---|---|---|
| 24 | 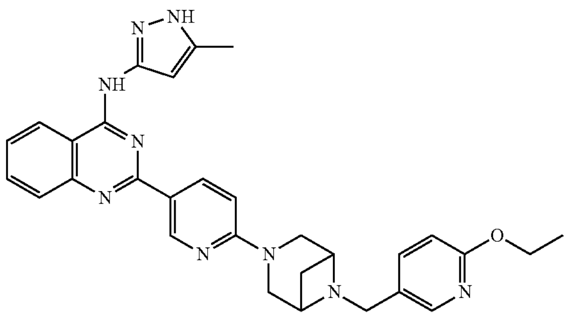 | 2-(6-(6-((6-ethoxypyridin-3-yl)methyl)-3,6-diazabicyclo[3.1.1]heptan-3-yl)pyridin-3-yl)-N-(5-methyl-1H-pyrazol-3-yl)quinazolin-4-amine | $^1$H NMR (400 MHz, DMSO-d$_6$) δ = 12.02 (s, 1H), 10.35 (s, 1H), 9.27 (d, J = 2.1 Hz, 1H), 8.65-8.56 (m, 2H), 8.23 (s, 1H), 7.83-7.76 (m, 3H), 7.49 (ddd, J = 8.2, 6.0, 2.2 Hz, 1H), 6.84 (t, J = 9.7 Hz, 2H), 6.73 (s, 1H), 4.31 (q, J = 7.0 Hz, 2H), 4.25-4.05 (m, 2H), 3.92 (s, 3H), 2.36 (s, 3H), 1.32 (t, J = 7.0 Hz, 3H) | 534.5 [M + H]$^+$ |
| 25 | 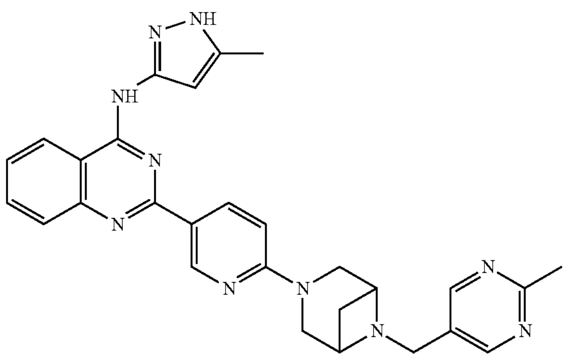 [SMILES: Cc1ncc(CN2C3CC2CN(c2ccc(-c4nc(Nc5cc(C)[nH]n5)c5ccccc5n4)cn2)C3)cn1] | N-(5-methyl-1H-pyrazol-3-yl)-2-(6-(6-((2-methylpyrimidin-5-yl)methyl)-3,6-diazabicyclo[3.1.1]heptan-3-yl)pyridin-3-yl)quinazolin-4-amine | $^1$H NMR (400 MHz, DMSO-d$_6$) δ = 12.10 (s, 1H), 10.66 (s, 1H), 9.25 (s, 1H), 8.87 (d, J = 6.3 Hz, 1H), 8.68-8.56 (m, 2H), 7.84 (q, J = 8.4 Hz, 2H), 7.54 (dd, J = 10.5, 4.1 Hz, 1H), 6.90 (d, J = 9.0 Hz, 1H), 6.71 (s, 1H), 4.74 (s, 1H), 4.55 (s, 2H), 4.02 (dd, J = 37.3, 15.8 Hz, 4H), 2.66 (s, 3H), 2.36 (s, 3H) | 505.5 [M + H]$^+$ |
| 26 | 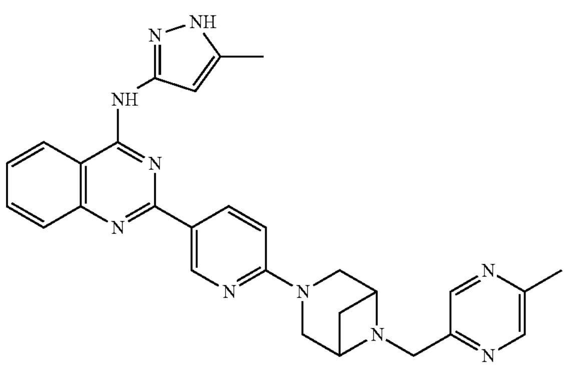 [SMILES: Cc1cnc(CN2C3CC2CN(c2ccc(-c4nc(Nc5cc(C)[nH]n5)c5ccccc5n4)cn2)C3)cn1] | N-(5-methyl-1H-pyrazol-3-yl)-2-(6-(6-((5-methylpyrazin-2-yl)methyl)-3,6-diazabicyclo[3.1.1]heptan-3-yl)pyridin-3-yl)quinazolin-4-amine | $^1$H NMR (400 MHz, DMSO-d$_6$) δ = 11.84 (s, 1H), 10.32 (d, J = 12.0 Hz, 1H), 9.25 (t, J = 4.0 Hz, 1H), 8.63-8.54 (m, 3H), 8.42 (s, 1H), 7.82-7.74 (m, 2H), 7.47 (ddd, J = 8.2, 5.9, 2.2 Hz, 1H), 6.81 (d, J = 9.0 Hz, 1H), 6.74 (s, 1H), 3.86 (d, J = 11.7 Hz, 2H), 3.75 (d, J = 5.7 Hz, 2H), 3.68 (s, 2H), 3.64-3.55 (m, 2H), 2.58-2.52 (m, 1H), 2.47 (s, 3H), 2.35 (s, 3H), 1.61 (d, J = 8.4 Hz, 1H) | 505.5 [M + H]$^+$ |
| 27 | 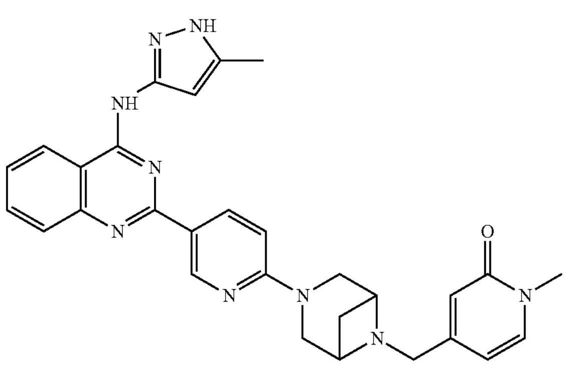 [SMILES: Cc1cc(Nc2nc(-c3ccc(N4CC5CC(C4)N5Cc4ccn(C)c(=O)c4)nc3)nc3ccccc23)n[nH]1] | 1-methyl-4-((3-(5-(4-((5-methyl-1H-pyrazol-3-yl)amino)quinazolin-2-yl)pyridin-2-yl)-3,6-diazabicyclo[3.1.1]heptan-6-yl)methyl)pyridin-2(1H)-one | $^1$H NMR (400 MHz, DMSO-d6) δ 12.21 (s, 1H), 10.31 (s, 1H), 9.14 (dd, J = 2.3, 0.8 Hz, 1H), 8.61 (d, J = 8.3 Hz, 1H), 8.48 (dd, J = 8.7, 2.3 Hz, 1H), 7.86-7.84 (m, 1H), 7.81-7.76 (m, 2H), 7.48 (ddd, J = 8.3, 6.2, 2.0 Hz, 1H), 7.18 (dd, J = 8.5, 2.4 Hz, 1H), 6.72 (s, 1H), 6.56 (ddd, J = 13.8, 8.6, 0.7 Hz, 2H), 4.40 (d, J = 5.8 Hz, 2H), 3.70 (s, 3H), 3.43 (s, 2H), 3.14 (d, J = 10.6 Hz, 2H), 2.73 (d, J = 10.4 Hz, 2H), 2.58-2.53 (m, 1H), 2.34 (s, 3H), 1.84 (d, J = 7.7 Hz, 1H) | 520.5 [M + H]$^+$ |

TABLE 1-continued

| Example compound | Structure | Name of compound | ¹H NMR | LC-MS (m/z) |
|---|---|---|---|---|
| 28 | 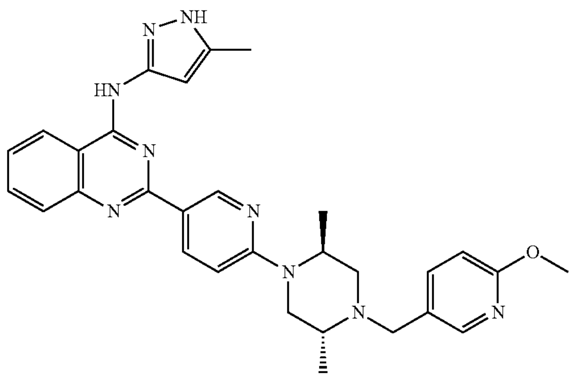 [SMILES: COc1ccc(CN2C[C@H](C)N(c3ccc(-c4nc(Nc5cc(C)[nH]n5)c5ccccc5n4)cn3)C[C@H]2C)cn1] | 2-(6-((2S,5R)-4-((6-methoxypyridin-3-yl)methyl)-2,5-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.27 (s, 1H), 9.13 (d, J = 2.4 Hz, 1H), 8.59 (d, J = 8.3 Hz, 1H), 8.47 (dd, J = 9.0, 2.4 Hz, 1H), 8.11 (d, J = 2.4 Hz, 1H), 7.79-7.70 (m, 3H), 7.46 (ddd, J = 8.3, 6.4, 1.8 Hz, 1H), 6.90-6.74 (m, 3H), 4.58 (s, 1H), 4.17-4.07 (m, 1H), 3.85 (s, 3H), 3.83 (s, 1H), 3.61 (d, J = 13.5 Hz, 1H), 3.45 (d, J = 13.5 Hz, 1H), 3.30 (d, J = 3.7 Hz, 1H), 3.10 (d, J = 6.8 Hz, 1H), 2.77 (dd, J = 11.7, 4.2 Hz, 1H), 2.34 (s, 3H), 1.17 (d, J = 6.5 Hz, 3H), 1.01-0.99 (m, 3H) | 536.5 [M + H]⁺ |
| 29 | 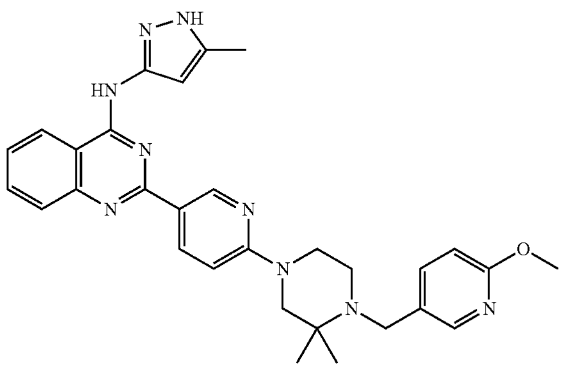 [SMILES: COc1ccc(CN2CCN(c3ccc(-c4nc(Nc5cc(C)[nH]n5)c5ccccc5n4)cn3)CC2(C)C)cn1] | 2-(6-(4-((6-methoxypyridin-3-yl)methyl)-3,3-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.28 (s, 1H), 9.12 (d, J = 2.4 Hz, 1H), 8.59 (d, J = 8.3 Hz, 1H), 8.46 (dd, J = 9.0, 2.4 Hz, 1H), 8.08 (d, J = 2.3 Hz, 1H), 7.81-7.71 (m, 2H), 7.67 (dd, J = 8.5, 2.4 Hz, 1H), 7.46 (ddd, J = 8.2, 6.4, 1.8 Hz, 1H), 6.96 (d, J = 9.1 Hz, 1H), 6.80 (dd, J = 8.5, 0.7 Hz, 1H), 6.71 (s, 1H), 3.84 (s, 3H), 3.58 (d, J = 5.7 Hz, 2H), 3.48 (d, J = 15.3 Hz, 4H), 2.43 (t, J = 5.3 Hz, 2H), 2.33 (s, 3H), 1.15 (s, 6H) | 536.5 [M + H]⁺ |
| 30 | 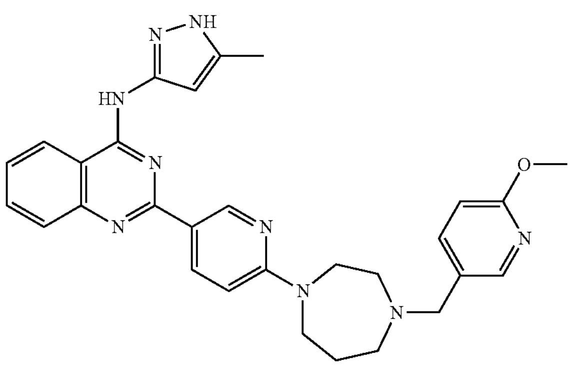 [SMILES: COc1ccc(CN2CCCN(c3ccc(-c4nc(Nc5cc(C)[nH]n5)c5ccccc5n4)cn3)CC2)cn1] | 2-(6-(4-((6-methoxypyridin-3-yl)methyl)-1,4-diazepan-1-yl)pyridin-3-yl)-N-(5-methyl-1H-pyrazol-3-yl)quinazolin-4-amine | ¹H NMR (400 MHz, DMSO-d6) δ 12.20 (s, 1H), 10.26 (s, 1H), 9.16-9.10 (m, 1H), 8.58 (d, J = 8.3 Hz, 1H), 8.47 (dd, J = 9.0, 2.4 Hz, 1H), 8.07-8.00 (m, 1H), 7.80-7.70 (m, 2H), 7.62 (dd, J = 8.5, 2.4 Hz, 1H), 7.45 (ddd, J = 8.2, 6.5, 1.7 Hz, 1H), 6.78-6.74 (m, 2H), 6.71 (s, 1H), 3.82 (s, 3H), 3.80 (d, J = 5.7 Hz, 2H), 3.72 (t, J = 6.2 Hz, 2H), 3.56 (s, 2H), 2.71 (t, J = 5.0 Hz, 2H), 2.57-2.53 (m, 2H), 2.34 (s, 3H), 1.91-1.85 (m, 2H) | 522.4 [M + H]⁺ |
| 31 | 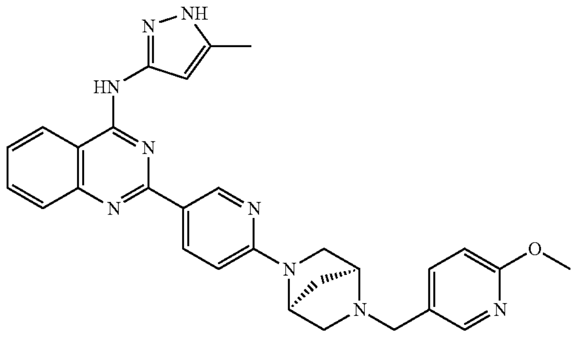 [SMILES: COc1ccc(CN2C[C@@H]3C[C@H]2CN3c2ccc(-c3nc(Nc4cc(C)[nH]n4)c4ccccc4n3)cn2)cn1] | 2-(6-((1S,4S)-5-((6-methoxypyridin-3-yl)methyl)-2,5-diazabicyclo[2.2.1]heptan-2-yl)pyridin-3-yl)-N-(5-methyl-1H-pyrazol-3-yl)quinazolin-4-amine | ¹H NMR (400 MHz, DMSO-d6) δ 12.21 (s, 1H), 10.26 (s, 1H), 9.14-9.10 (m, 1H), 8.58 (d, J = 8.3 Hz, 1H), 8.46 (dd, J = 8.9, 2.3 Hz, 1H), 8.09-8.04 (m, 1H), 7.80-7.71 (m, 2H), 7.66 (dd, J = 8.5, 2.4 Hz, 1H), 7.45 (ddd, J = 8.3, 6.4, 1.8 Hz, 1H), 6.75 (dd, J = 8.5, 0.7 Hz, 1H), 6.71 (s, 1H), 6.63 (d, J = 8.9 Hz, 1H), 4.78 (s, 1H), 3.82 (s, 3H), 3.64 (s, 2H), 3.57 (d, J = 10.6 Hz, 2H), 3.40 (dd, J = 9.9, 2.2 Hz, 1H), 2.87 (d, J = 9.5, 2.1 Hz, 1H), 2.52 (d, J = 3.5 Hz, 1H), 2.34 (s, 3H), 1.94 (d, J = 9.4 Hz, 1H), 1.80 (d, J = 9.3 Hz, 1H) | 520.5 [M + H]⁺ |

TABLE 1-continued

| Example compound | Structure | Name of compound | ¹H NMR | LC-MS (m/z) |
|---|---|---|---|---|
| 32 | 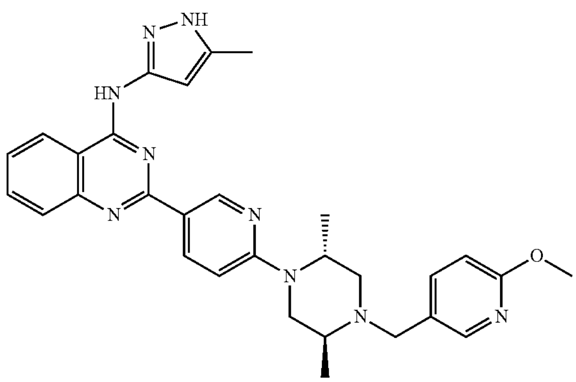 | 2-(6-((2R,5S)-4-((6-methoxypyridin-3-yl)methyl)-2,5-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.27 (s, 1H), 9.13 (d, J = 2.4 Hz, 1H), 8.59 (d, J = 8.2 Hz, 1H), 8.47 (dd, J = 9.0, 2.4 Hz, 1H), 8.11 (d, J = 2.3 Hz, 1H), 7.79-7.70 (m, 3H), 7.46 (ddd, J = 8.3, 6.4, 1.8 Hz, 1H), 6.90-6.71 (m, 3H), 4.58 (s, 1H), 4.16-4.09 (m, 1H), 3.85 (s, 3H), 3.61 (d, J = 13.5 Hz, 1H), 3.45 (d, J = 13.5 Hz, 1H), 3.30 (d, J = 3.7 Hz, 1H), 3.12-3.05 (m, 1H), 2.77 (dd, J = 11.7, 4.2 Hz, 1H), 2.34 (s, 3H), 2.30 (dd, J = 11.8, 1.9 Hz, 1H), 1.17 (d, J = 6.6 Hz, 3H), 1.00 (d, J = 6.5 Hz, 3H) | 536.5 [M + H]⁺ |
| 33 | 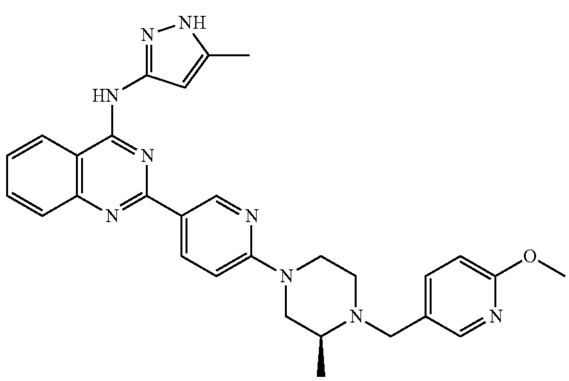 [SMILES: COc1ccc(CN2CCN(c3ccc(-c4nc(Nc5cc(C)[nH]n5)c5ccccc5n4)cn3)C[C@@H]2C)cn1] | (S)-2-(6-(4-((6-methoxypyridin-3-yl)methyl)-3-methylpiperazin-1-yl)pyridin-3-yl)-N-(5-methyl-1H-pyrazol-3-yl)quinazolin-4-amine | ¹H NMR (400 MHz, DMSO-d6) δ 12.20 (s, 1H), 10.29 (s, 1H), 9.14 (d, J = 2.4 Hz, 1H), 8.59 (d, J = 8.3 Hz, 1H), 8.48 (dd, J = 9.0, 2.4 Hz, 1H), 8.08 (d, J = 2.4 Hz, 1H), 7.81-7.72 (m, 2H), 7.66 (dd, J = 8.5, 2.4 Hz, 1H), 7.46 (ddd, J = 8.3, 6.3, 1.9 Hz, 1H), 6.94 (d, J = 9.1 Hz, 1H), 6.80 (dd, J = 8.4, 0.7 Hz, 1H), 6.70 (s, 1H), 4.12-4.05 (m, 1H), 4.04-3.96 (m, 1H), 3.92 (d, J = 13.5 Hz, 1H), 3.84 (s, 3H), 3.20 (d, J = 13.4 Hz, 1H), 3.18-3.11 (m, 1H), 2.97 (dd, J = 12.8, 8.8 Hz, 1H), 2.70 (dt, J = 11.7, 3.6 Hz, 1H), 2.48 (dd, J = 6.0, 3.1 Hz, 1H), 2.33 (s, 3H), 2.16 (ddd, J = 11.3, 9.8, 3.3 Hz, 1H), 1.18 (d, J = 6.1 Hz, 3H) | 522.5 [M + H]⁺ |
| 34 | 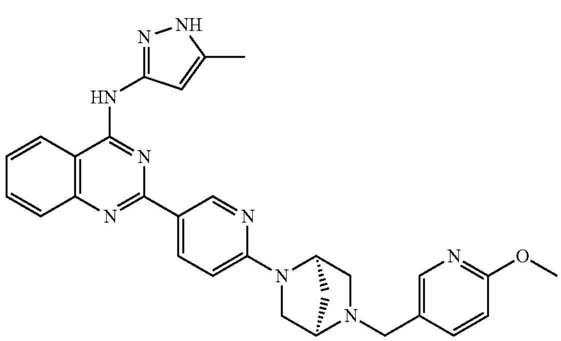 [SMILES: COc1ccc(CN2C[C@H]3C[C@@H]2CN3c2ccc(-c3nc(Nc4cc(C)[nH]n4)c4ccccc4n3)cn2)cn1] | 2-(6-((1R,4R)-5-((6-methoxypyridin-3-yl)methyl)-2,5-diazabicyclo[2.2.1]heptan-2-yl)pyridin-3-yl)-N-(5-methyl-1H-pyrazol-3-yl)quinazolin-4-amine | ¹H NMR (400 MHz, DMSO-d6) δ 12.18 (s, 1H), 10.27 (s, 1H), 9.15-9.10 (m, 1H), 8.58 (d, J = 8.3 Hz, 1H), 8.46 (dd, J = 8.9, 2.3 Hz, 1H), 8.09-8.03 (m, 1H), 7.81-7.71 (m, 2H), 7.66 (dd, J = 8.5, 2.4 Hz, 1H), 7.45 (ddd, J = 8.3, 6.4, 1.8 Hz, 1H), 6.78-6.59 (m, 3H), 4.78 (s, 1H), 3.82 (s, 3H), 3.64 (s, 2H), 3.57 (d, J = 10.3 Hz, 2H), 3.40 (dd, J = 9.9, 2.2 Hz, 1H), 2.87 (dd, J = 9.4, 2.1 Hz, 1H), 2.52 (d, J = 3.2 Hz, 1H), 2.34 (s, 3H), 1.94 (d, J = 9.3 Hz, 1H), 1.80 (d, J = 9.3 Hz, 1H) | 520.4 [M + H]⁺ |
| 35 | 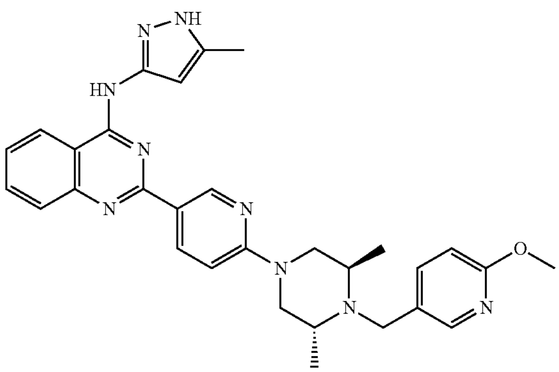 [SMILES: COc1ccc(CN2[C@H](C)CN(c3ccc(-c4nc(Nc5cc(C)[nH]n5)c5ccccc5n4)cn3)C[C@H]2C)cn1] | 2-(6-((3R,5S)-4-((6-methoxypyridin-3-yl)methyl)-3,5-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.29 (s, 1H), 9.13 (d, J = 2.4 Hz, 1H), 8.59 (d, J = 8.3 Hz, 1H), 8.48 (dd, J = 9.0, 2.4 Hz, 1H), 8.15 (d, J = 2.4 Hz, 1H), 7.80-7.73 (m, 2H), 7.69 (dd, J = 8.5, 2.5 Hz, 1H), 7.46 (ddd, J = 8.2, 6.4, 1.9 Hz, 1H), 6.97 (d, J = 9.1 Hz, 1H), 6.77 (dd, J = 8.5, 0.6 Hz, 1H), 6.70 (s, 1H), 4.26 (d, J = 11.1 Hz, 2H), 3.82 (s, 3H), 3.76 (s, 2H), 2.75 (dd, J = 12.9, 10.2 Hz, 2H), 2.63-2.55 (m, 2H), 2.34 (s, 3H), 1.09 (d, J = 6.0 Hz, 6H) | 536.5 [M + H]⁺ |

TABLE 1-continued

| Example compound | Structure | Name of compound | ¹H NMR | LC-MS (m/z) |
|---|---|---|---|---|
| 36 | 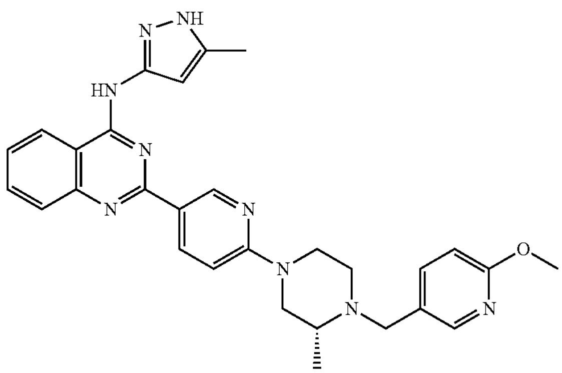 [SMILES: COc1ccc(CN2CCN(c3ccc(-c4nc(Nc5cc(C)[nH]n5)c5ccccc5n4)cn3)C[C@H]2C)cn1] | (R)-2-(6-(4-((6-methoxypyridin-3-yl)methyl)-3-methylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.29 (s, 1H), 9.14 (d, J = 2.4 Hz, 1H), 8.59 (d, J = 8.3 Hz, 1H), 8.48 (dd, J = 9.0, 2.4 Hz, 1H), 8.08 (d, J = 2.4 Hz, 1H), 7.81-7.73 (m, 2H), 7.66 (dd, J = 8.5, 2.4 Hz, 1H), 7.46 (ddd, J = 8.3, 6.3, 1.9 Hz, 1H), 6.94 (d, J = 9.0 Hz, 1H), 6.80 (dd, J = 8.4, 0.7 Hz, 1H), 6.71 (s, 1H), 4.08 (dt, J = 12.3, 3.0 Hz, 1H), 4.00 (d, J = 12.7 Hz, 1H), 3.92 (d, J = 13.5 Hz, 1H), 3.84 (s, 3H), 3.20 (d, J = 13.4 Hz, 1H), 3.15 (ddd, J = 12.8, 8.2, 3.4 Hz, 1H), 2.97 (dd, J = 12.8, 8.8 Hz, 1H), 2.74-2.66 (m, 1H), 2.50-2.46 (m, 1H), 2.33 (s, 3H), 2.16 (ddd, J = 13.0, 10.4, 3.2 Hz, 1H), 1.18 (d, J = 6.1 Hz, 3H) | 522.5 [M + H]⁺ |
| 37 | 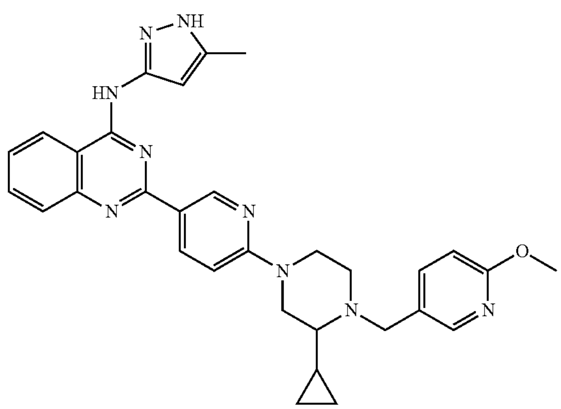 | 2-(6-(4-((6-methoxypyridin-3-yl)methyl)-4,7-diazaspiro[2.5]octan-7-yl)pyridin-3-yl)-N-(5-methyl-1H-pyrazol-3-yl)quinazolin-4-amine | ¹H NMR (400 MHz, DMSO-d6) δ 12.21 (s, 1H), 10.29 (s, 1H), 9.15 (d, J = 2.4 Hz, 1H), 8.59 (d, J = 8.3 Hz, 1H), 8.49 (dd, J = 9.0, 2.4 Hz, 1H), 8.10-8.05 (m, 1H), 7.81-7.73 (m, 2H), 7.62 (dd, J = 8.5, 2.4 Hz, 1H), 7.46 (ddd, J = 8.3, 6.3, 1.9 Hz, 1H), 6.93 (d, J = 9.1 Hz, 1H), 6.78 (ddd, J = 8.4, 2.4, 0.7 Hz, 1H), 6.71 (d, J = 8.1 Hz, 1H), 3.83 (q, J = 5.8, 5.3 Hz, 6H), 3.70-3.65 (m, 2H), 3.57 (s, 2H), 2.84-2.78 (m, 2H), 2.33 (s, 3H), 0.64 (dt, J = 11.8, 1.9 Hz, 3H) | 534.5 [M + H]⁺ |

<Experimental Example 1> Evaluation of RET Enzyme Inhibitory Ability

The following experiment was performed in order to evaluate the RET enzyme inhibitory activity of the example compound according to the present invention.

The Example compound was reacted with a purified human RET (658-end, SIGNALCHEM) enzyme to evaluate the enzyme inhibitory ability by the following method. As a reaction buffer, a composition of 40 mM Tris-HCl pH 7.4, 20 mM MgCl$_2$, 0.5 mg/mL BSA, and 50 μM DTT was used, and all experimental materials were reacted on the reaction buffer. After the human RET (658-end, 0.8 ng) enzyme was reacted with purified ATP (10 μM) and a specific substrate solution at 25° C. for 1 hour during the experiment, the enzyme activity was confirmed using in vitro ADP-Glo™ kinase assay (Promega). Luminescence was measured by reacting the enzyme activity reaction solution, the ADP-Glo reaction solution, and the enzyme activity detection solution at a ratio of 2:2:1. The degree of inhibition of enzyme activity according to the treatment concentration of each compound was calculated based on the fluorescence of the enzyme activity of a solvent control group in which a compound was not treated, and in this case, the concentration of each compound which suppresses the inhibition of enzyme activity by 50% was determined as an IC$_{50}$ (nM) value. The IC$_{50}$ (nM) of each compound was determined by 3 datasets and obtained using Prism (version 7.01, GraphPad) software. The results are shown in the following Table 2.

<Experimental Example 2> Evaluation of Inhibitory Activity Against Proliferation of Medullary Thyroid Cancer and Lung Cancer Cells, which Express RET Fusion Genes In order to evaluate the inhibitory activity of the compound according to the present invention against the proliferation of medullary thyroid cancer cells and lung cancer cell proliferation, which express RET fusion genes, the following experiment was performed.

Among lung cancer cell lines, which express RET fusion genes, LC-2/ad cells were cultured after adding 10% FBS (HyClone) to RPMI:F12 (1:1) (Invitrogen), and F-12 (Invitrogen) supplemented with 10% FBS was used for TT cells. RPMI-1640 supplemented with 10% FBS and 5 ng/ml IL-3 (R&D Systems) was used for Ba/F3 cells. Transduced Ba/F3 cells were cultured by adding 1 ug/ml puromycin (Invitrogen) to the same medium. 24 hours before cells were treated with the compound, 3000 to 5000 cells were aliquoted into each well of a white clear bottom 96 well plate (Corning). The compound was diluted in DMSO (3-fold dilution, a total of 12 concentrations) and the compound was injected by 0.5 μl such that the final concentration was 0.3 nM to 50 μM. For the measurement of living cells, 72 hours after the compound treatment, the cells were stored at room temperature for 10 minutes using a CellTiter-Glo luminescent cell-viability agent (Promega), and then the luminescence intensity was measured using a reader (SynergyNeo, Biotek). Each experiment was repeated in triplicate. The result value was calculated by the cell growth ratio (%) compared to the control. A graph was drawn using the GraphPad Prism version 5.0 program, and a $GI_{50}$ (nM) value was calculated. The results are shown in the following Table 2.

TABLE 2

| Example Compound | Enzyme assay ($IC_{50}$, nM) | | | Cell assay ($GI_{50}$, nM) | | | | | |
|---|---|---|---|---|---|---|---|---|---|
| | RET (WT) | RET (V804M) | CCDC6-RET | LC-2/ad | Ba/F3 (naive) | Ba/F3 CCDC6-RET (WT) | Ba/F3 KIF5B-RET (WT) | Ba/F3 KIF5B-RET (V804M) | TT |
| 1 | 18 | 2.2 | 1.8 | 14 | 4896 | 59 | 19 | 19 | 88 |
| 2 | 12 | | | | 4380 | 49 | 11 | 14 | 48 |
| 3 | 7 | 0.7 | 0.9 | 60 | 2301 | 51 | 13 | 3 | 30 |
| 4 | >15000 | | | | >15000 | | | >15000 | >15000 |
| 5 | 18 | | | | 1056 | 41 | 7 | 4 | |
| 6 | 27 | | | | 9223 | 166 | 67 | 70 | |
| 7 | 10 | | | | 6068 | 45 | 15 | 7 | 41 |
| 8 | 32 | | | | 1979 | 51 | 12 | 23 | |
| 9 | 30 | | | | 822 | 62 | 23 | 23 | |
| 10 | 10 | | | | 920 | 39 | 9 | 10 | |
| 11 | | | | | | | | 119 | |
| 12 | 38 | | | | 2541 | 52 | 15 | 49 | |
| 13 | | | | | | | | 2449 | |
| 14 | 10 | | | | 2695 | 33 | 11 | 22 | |
| 15 | 40 | | | | 3097 | 75 | 24 | 30 | |
| 16 | 60 | | | | 4014 | 127 | 42 | 39 | |
| 17 | 11 | | | | 867 | 46 | 10 | 7 | |
| 18 | 34 | | | | 4603 | 67 | 28 | 25 | |
| 19 | 40 | | | | 1233 | 120 | 29 | 28 | |
| 20 | 14 | | | | 2784 | 44 | 11 | 6 | |
| 21 | | | | | | | | 117 | |
| 22 | 20 | | | | 1218 | 55 | 20 | 6 | |
| 23 | 15 | | | | 1301 | 57 | 14 | 19 | |
| 24 | 14 | | | | 4321 | 53 | 12 | 10 | |
| 25 | 7 | | | | 1651 | 50 | 14 | 21 | |
| 26 | 7 | | | | 973 | 37 | 10 | 10 | |
| 27 | | | | | | | | 159 | |
| 28 | | | | | | | | 321 | |
| 29 | 123 | | | | 6316 | 454 | 164 | 89 | |
| 30 | 34 | | | | 1127 | 99 | 44 | 25 | |
| 31 | 25 | | | | 1685 | 66 | 18 | 12 | |
| 32 | | | | | | | | 239 | |
| 33 | | | | | | | | 121 | |
| 34 | 16 | | | | 2591 | 65 | 19 | 20 | |
| 35 | | | | | | | | 328 | |
| 36 | 59 | | | | 4803 | 259 | 63 | 32 | |
| 37 | 219 | | | | 4648 | 305 | 107 | 50 | |

In the enzyme assay column, RET (WT) is a non-mutated form, RET (V804M) is a mutated form in which the V amino acid at position 804 of the RET is substituted with M, and CCDC6-RET is a form in which the RET (WT) gene and CCDC6 gene are fused.

In the cell assay column, LC-2/ad (with CCDC6-RET gene) is a lung cancer cell line, a TT cell line (without RET (WT) gene) is a thyroid cancer cell line, Ba/F3 CCDC6-RET (WT), Ba/F3 KIF5B-RET (WT), and Ba/F3 KIF5B-RET (V804M) are cells in which disease-related traits (CCDC6-RET, KIF5B-RET, and KIF5B-RET (V804M)) are introduced into Ba/F3 cells, and Ba/F3 (naive) is a cell which is not transduced.

As shown in Table 2, as a result of measuring the cell growth inhibitory activity of each Example compound against LC-2/ad, Ba/F3 naive, Ba/F3 CCDC6-RET, Ba/F3 KIF5B-RET, Ba/F3 KIF5B-RET (V804M), and TT cells, it can be confirmed that the Example compound of the present invention excellently inhibits the proliferation of a Ba/F3 cell line and medullary thyroid cancer or lung cancer cell lines, which express RET fusion genes.

Therefore, as confirmed in the experiments, the compound according to the present invention can suppress the proliferation of cancer cells, and thus, can be usefully used as a pharmaceutical composition for the prevention and treatment of a cancer disease, for example, medullary thyroid cancer or lung cancer.

<Experimental Example 3> Evaluation of Inhibitory Activity of Compound According to Present Invention Against Various Kinases The following experiment was performed in order to evaluate the inhibitory activity of the compound according to the present invention against more enzymes. Specifically, for Examples 1 and 3 selected among the Example compounds of the present invention, the enzyme (kinase) selectivity was set to be measured by commissioning DiscoverX, and an experiment was conducted using a ScanMAX™ Kinase analysis panel. In this case, the concentration of the drug treated with the enzyme was set to 1 μM in DMSO, the adjusted percentage (% control) was determined in the same manner as in the following Equation 1, and the results are shown in the following Table 3.

(Example compound−Positive control)/(Negative control−Positive control)×100 [Equation 1]

Here, the positive control refers to a compound showing an adjusted percentage of 0%, and the negative control shows an adjusted percentage of 100% with DMSO. In addition, the enzyme selectivity of the present invention was determined to be active against the corresponding enzyme when the adjusted percentage was <35% (that is, less than 35%).

TABLE 3

| Kinase | Example 1 | Example 3 |
|---|---|---|
| ABL1(H396P)-nonphosphorylated | 10 | 2.5 |
| ABL1(H396P)-phosphorylated | 28 | 21 |
| ABL1(M351T)-phosphorylated | 16 | 15 |
| ABL1(Q252H)-phosphorylated | 15 | 17 |
| ABL1(T315I)-nonphosphorylated | 20 | 2.9 |
| ABL1(T315I)-phosphorylated | 19 | 3.2 |
| ABL1(Y253F)-phosphorylated | 20 | 21 |
| ABL1-phosphorylated | 30 | 15 |
| AMPK-alpha1 | 26 | 33 |
| AURKA | 4.1 | 2.2 |
| AURKC | 15 | 21 |
| AXL | 1.2 | 0 |
| BLK | 1.4 | 0.05 |
| BTK | 17 | 16 |
| CSNK2A1 | 2.4 | 1.5 |
| CSNK2A2 | 0 | 0.3 |
| DAPK3 | 19 | 34 |
| DDR1 | 25 | 12 |
| DDR2 | 16 | 30 |
| DLK | 29 | 19 |
| EGFR(L747-E749del, A750P) | 16 | 17 |
| EGFR(L858R, T790M) | 6.9 | 6.6 |
| EGFR(T790M) | 8.1 | 16 |
| EPHB6 | 2.6 | 4.8 |
| FGFR1 | 11 | 4.3 |
| FGR | 12 | 8.4 |
| FLT3 | 1.2 | 0.55 |
| FLT3(D835H) | 6.7 | 2.7 |
| FLT3(D835V) | 1.3 | 0 |
| FLT3(D835Y) | 1.5 | 0.55 |
| FLT3(ITD) | 4.9 | 1.2 |
| FLT3(ITD, D835V) | 0 | 0 |
| FLT3(ITD, F691L) | 1.4 | 8.8 |
| FLT3(K663Q) | 2.2 | 0.1 |
| FLT3(N841I) | 0 | 0 |
| FLT3(R834Q) | 23 | 9.1 |
| FLT3-autoinhibited | 9.8 | 11 |
| FRK | 18 | 34 |
| GCN2(Kin.Dom.2, S808G) | 8 | 0.2 |
| HCK | 4.1 | 3.2 |
| ICK | 33 | 28 |
| ITK | 2 | 1.6 |
| JAK1(JH1domain-catalytic) | 15 | 9.7 |
| JAK1(JH2domain-pseudokinase) | 21 | 2.9 |
| JAK2(JH1domain-catalytic) | 0.1 | 0 |
| JAK3(JH1domain-catalytic) | 0.55 | 1.9 |
| KIT(A829P) | 2.8 | 11 |
| KIT(D816V) | 32 | 6.5 |
| KIT(V559D) | 34 | 4.2 |
| LCK | 2.5 | 1.8 |
| MAP3K2 | 27 | 7.4 |
| MEK2 | 24 | 17 |
| MEK3 | 27 | 4.9 |
| MEK5 | 9.9 | 2.2 |
| MERTK | 34 | 6.2 |
| MST1 | 25 | 30 |
| PDGFRB | 15 | 2.7 |
| PLK4 | 1.3 | 1.2 |
| RET | 0 | 0 |
| RET(M918T) | 0.9 | 0.25 |
| RET(V804L) | 1.1 | 0.4 |

TABLE 3-continued

| Kinase | Example 1 | Example 3 |
|---|---|---|
| RET(V804M) | 0 | 0 |
| RIOK3 | 13 | 30 |
| SNARK | 22 | 17 |
| SRC | 0.7 | 0 |
| SYK | 3.1 | 2.2 |
| TRKA | 0 | 0 |
| TRKB | 1.6 | 2.1 |
| TRKC | 0.45 | 1 |
| TYK2(JH1domain-catalytic) | 0.2 | 5.3 |
| YES | 11 | 3.8 |
| YSK4 | 6.2 | 5 |

As can be confirmed in Table 3, it can be seen that the compound according to the present invention has a value less than an adjusted percentage of 35% against ABL1 (H396P)-nonphosphorylated, ABL1(H396P)-phosphorylated, ABL1(M351T)-phosphorylated, ABL1(Q252H)-phosphorylated, ABL1(T315I)-nonphosphorylated, ABL1 (T315I)-phosphorylated, ABL1(Y253F)-phosphorylated, ABL1-phosphorylated, AMPK-alpha1, AURKA, AURKC, AXL, BLK, BTK, CSNK2A1, CSNK2A2, DAPK3, DDR1, DDR2, DLK, EGFR(L747-E749del, A750P), EGFR (L858R,T790M), EGFR(T790M), EPHB6, FGFR1, FGR, FLT3, FLT3(D835H), FLT3(D835V), FLT3(D835Y), FLT3 (ITD), FLT3(ITD,D835V), FLT3(ITD,F691L), FLT3 (K663Q), FLT3(N841I), FLT3(R834Q), FLT3-autoinhibited, FRK, GCN2(Kin.Dom.2,S808G), HCK, ICK, ITK, JAK1(JH1domain-catalytic), JAK1(JH2domain-pseudokinase), JAK2(JH1domain-catalytic), JAK3 (JH1domain-catalytic), KIT(A829P), KIT(D816V), KIT(V559D), LCK, MAP3K2, MEK2, MEK3, MEK5, MERTK, MST1, PDGFRB, PLK4, RET, RET(M918T), RET(V804L), RET (V804M), RIOK3, SNARK, SRC, SYK, TRKA, TRKB, TRKC, TYK2(JH1domain-catalytic), YES, or YSK4 kinase. This suggests that the compound according to the present invention exhibits a suppressive activity against the above-listed enzymes, and has a useful effect when used in diseases associated with the above-listed enzymes. Therefore, the derivative compound according to the present invention can be usefully used as a composition for treating or preventing a disease associated with the above-listed enzymes.

The invention claimed is:

1. A compound of the following Chemical Formula 1, a stereoisomer thereof, a solvate thereof, a hydrate thereof, or a pharmaceutically acceptable salt thereof:

[Chemical Formula 1]

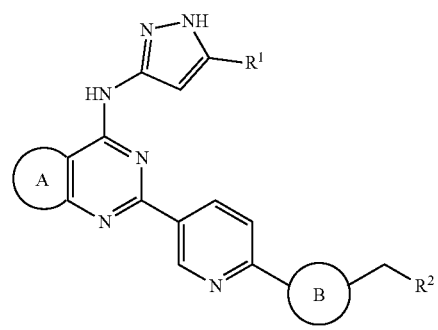

wherein

is furan, thiophene, benzene, or cyclopentene, $R^1$ is a straight or branched $C_1$-$C_3$ alkyl, wherein $R^1$ is unsubstituted or substituted with at least one halogen, Ring B is diazabicycloheptane, piperazine, diazepane, or diazaspirooctane, wherein Ring B is unsubstituted or substituted with at least one straight or branched $C_1$-$C_6$ alkyl, $R^2$ is pyridinyl, thiazolyl, phenyl, imidazolyl, pyrazinyl, quinolinyl, pyrimidinyl, or pyridonyl, wherein $R^2$ is unsubstituted or substituted with at least one $R^3$, and $R^3$ is at least one substituent selected from the group consisting of a straight or branched $C_1$-$C_6$ alkyl, a straight or branched $C_1$-$C_6$ haloalkyl, a straight or branched $C_1$-$C_6$ alkoxy, a halogen, a $C_1$-$C_3$ alkanesulfonamido, an amino substituted with at least one straight or branched $C_1$-$C_3$ alkyl, and nitrile.

2. The compound, the stereoisomer thereof, the solvate thereof, the hydrate thereof, or the pharmaceutically acceptable salt thereof of claim 1, wherein Ring B is 3,6-diazabicyclo[3.1.1]heptane, 2,5-diazabicyclo[2.2.1]heptane, piperazine, diazepane or 4,7-diazaspiro[2,5]octane.

3. The compound, the stereoisomer thereof, the solvate thereof, the hydrate thereof, or the pharmaceutically acceptable salt thereof of claim 1, wherein when $R^2$ is pyridinyl, thiazolyl, phenyl, pyrazinyl, pyrimidinyl, or pyridonyl, $R^2$ is substituted with at least one $R^3$, or when $R^2$ is imidazolyl or quinoline, $R^2$ is not substituted, and $R^3$ is at least one substituent selected from the group consisting of a straight or branched $C_1$-$C_3$ alkyl, a straight or branched $C_1$-$C_3$ haloalkyl, a straight or branched $C_1$-$C_3$ alkoxy, a halogen, a $C_1$-$C_3$ alkanesulfonamido, an amino substituted with at least one straight or branched $C_1$-$C_3$ alkyl, and nitrile.

4. The compound, the stereoisomer thereof, the solvate thereof, the hydrate thereof, or the pharmaceutically acceptable salt thereof of claim 1, wherein the compound of Chemical Formula 1 is any one selected from the following compounds:

<1> 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)furo[3,2-d]pyrimidin-4-amine; <2> 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl) thieno[3,2-d]pyrimidin-4-amine; <3> 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)quinazolin-4-amine; <4> 2-(6-(6-((6-methoxypyridin-3-yl)methyl)-3,6-diazabicyclo[3.1.1]heptan-3-yl)pyridin-3-yl)-N-(5-(trifluoromethyl)-1H-pyrazol-3-yl)furo[3,2-d]pyrimidin-4-amine; <5> N-(5-methyl-1H-pyrazol-3-yl)-2-(6-(6-((5-methylthiazol-2-yl)methyl)-3,6-diazabicyclo[3.1.1]heptan-3-yl)pyridin-3-yl)quinazolin-4-amine; <6> 2-(6-(3-((6-methoxypyridin-3-yl)methyl)-3,6-diazabicyclo[3.1.1]heptan-6-yl)pyridin-3-yl)-N-(5-methyl-1H-pyrazol-3-yl)quinazolin-4-amine; <7> 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)-6,7-dihydro-5H-cyclopenta[d]pyrimidin-4-amine; <8> N-(5-methyl-1H-pyrazol-3-yl)-2-(6-(6-((6-(trifluoromethyl)pyridin-3-yl)methyl)-3,6-diazabicyclo[3.1.1]heptan-3-yl)pyridin-3-yl)quinazolin-4-amine; <9> 5-((3-(5-(4-((5-methyl-1H-pyrazol-3-yl)amino) quinazolin-2-yl)pyridin-2-yl)-3,6-diazabicyclo[3.1.1]heptan-6-yl)methyl)picolinonitrile; <10> N-(5-methyl-1H-pyrazol-3-yl)-2-(6-(6-((6-methylpyridin-3-yl)methyl)-3,6-diazabicyclo[3.1.1]heptan-3-yl)pyridin-3-yl)quinazolin-4-amine; <11> 2-(6-(6-(3,5-difluoro-4-isopropoxybenzyl)-3,6-diazabicyclo[3.1.1]heptan-3-yl)pyridin-3-yl)-N-(5-methyl-1H-pyrazol-3-yl)quinazolin-4-amine; <12> 2-methoxy-5-((3-(5-(4-((5-methyl-1H-pyrazol-3-yl)amino) quinazolin-2-yl)pyridin-2-yl)-3,6-diazabicyclo[3.1.1]heptan-6-yl)methyl)benzonitrile; <13> 2-(6-(6-((1H-imidazol-5-yl)methyl)-3,6-diazabicyclo[3.1.1]heptan-3-yl)pyridin-3-yl)-N-(5-methyl-1H-pyrazol-3-yl)quinazolin-4-amine; <14> 2-(6-(6-(4-methoxybenzyl)-3,6-diazabicyclo[3.1.1]heptan-3-yl)pyridin-3-yl)-N-(5-methyl-1H-pyrazol-3-yl)quinazolin-4-amine; <15> 2-(6-(6-((6-isopropoxypyridin-3-yl)methyl)-3,6-diazabicyclo[3.1.1]heptan-3-yl)pyridin-3-yl)-N-(5-methyl-1H-pyrazol-3-yl)quinazolin-4-amine; <16> 2-(6-(6-((5-chloro-6-methoxypyridin-3-yl)methyl)-3,6-diazabicyclo[3.1.1]heptan-3-yl)pyridin-3-yl)-N-(5-methyl-1H-pyrazol-3-yl)quinazolin-4-amine; <17> 2-(6-(6-((5-methoxypyrazin-2-yl)methyl)-3,6-diazabicyclo[3.1.1]heptan-3-yl)pyridin-3-yl)-N-(5-methyl-1H-pyrazol-3-yl)quinazolin-4-amine; <18> N-(5-methyl-1H-pyrazol-3-yl)-2-(6-(6-(quinolin-6-ylmethyl)-3,6-diazabicyclo[3.1.1]heptan-3-yl)pyridin-3-yl)quinazolin-4-amine; <19> N-(5-methyl-1H-pyrazol-3-yl)-2-(6-(6-((4-methylthiazol-2-yl)methyl)-3,6-diazabicyclo[3.1.1]heptan-3-yl)pyridin-3-yl)quinazolin-4-amine; <20> 2-(6-(6-((6-(dimethylamino)pyridin-3-yl)methyl)-3,6-diazabicyclo[3.1.1]heptan-3-yl)pyridin-3-yl)-N-(5-methyl-1H-pyrazol-3-yl)quinazolin-4-amine; <21> N-(4-((3-(5-(4-((5-methyl-1H-pyrazol-3-yl)amino)quinazolin-2-yl)pyridin-2-yl)-3,6-diazabicyclo[3.1.1]heptan-6-yl)methyl)phenyl)methanesulfonamide; <22> 2-(6-(6-(4-fluorobenzyl)-3,6-diazabicyclo[3.1.1]heptan-3-yl)pyridin-3-yl)-N-(5-methyl-1H-pyrazol-3-yl)quinazolin-4-amine; <23> 2-(6-(6-((6-fluoropyridin-3-yl)methyl)-3,6-diazabicyclo[3.1.1]heptan-3-yl)pyridin-3-yl)-N-(5-methyl-1H-pyrazol-3-yl)quinazolin-4-amine; <24> 2-(6-(6-((6-ethoxypyridin-3-yl)methyl)-3,6-diazabicyclo[3.1.1]heptan-3-yl)pyridin-3-yl)-N-(5-methyl-1H-pyrazol-3-yl)quinazolin-4-amine; <25> N-(5-methyl-1H-pyrazol-3-yl)-2-(6-(6-((2-methylpyrimidin-5-yl)methyl)-3,6-diazabicyclo[3.1.1]heptan-3-yl)pyridin-3-yl)quinazolin-4-amine; <26> N-(5-methyl-1H-pyrazol-3-yl)-2-(6-(6-((5-methylpyrazin-2-yl)methyl)-3,6-diazabicyclo[3.1.1]heptan-3-yl)pyridin-3-yl)quinazolin-4-amine; <27> 1-methyl-4-((3-(5-(4-((5-methyl-1H-pyrazol-3-yl)amino)quinazolin-2-yl)pyridin-2-yl)-3,6-diazabicyclo[3.1.1]heptan-6-yl)methyl)pyridin-2 (1H)-one; <28> 2-(6-((2S,5R)-4-((6-methoxypyridin-3-yl)methyl)-2,5-dimethylpiperazin-1-yl)pyridin-3-yl)-N-(5-methyl-1H-pyrazol-3-yl)quinazolin-4-amine; <29> 2-(6-(4-((6-methoxypyridin-3-yl)methyl)-3,3-dimethylpiperazin-1-yl)pyridin-3-yl)-N-(5-methyl-1H-pyrazol-3-yl)quinazolin-4-amine; <30> 2-(6-(4-((6-methoxypyridin-3-yl)methyl)-1,4-diazepan-1-yl)pyridin-3-yl)-N-(5-methyl-1H-pyrazol-3-yl)

quinazolin-4-amine; <31> 2-(6-((1S,4S)-5-((6-methoxypyridin-3-yl)methyl)-2,5-diazabicyclo[2.2.1]heptan-2-yl)pyridin-3-yl)-N-(5-methyl-1H-pyrazol-3-yl)quinazolin-4-amine; <32> 2-(6-((2R,5S)-4-((6-methoxypyridin-3-yl)methyl)-2,5-dimethylpiperazin-1-yl)pyridin-3-yl)-N-(5-methyl-1H-pyrazol-3-yl)quinazolin-4-amine; <33> (S)-2-(6-(4-((6-methoxypyridin-3-yl)methyl)-3-methylpiperazin-1-yl)pyridin-3-yl)-N-(5-methyl-1H-pyrazol-3-yl)quinazolin-4-amine; <34> 2-(6-((1R,4R)-5-((6-methoxypyridin-3-yl)methyl)-2,5-diazabicyclo[2.2.1]heptan-2-yl)pyridin-3-yl)-N-(5-methyl-1H-pyrazol-3-yl)quinazolin-4-amine; <35> 2-(6-((3R,5S)-4-((6-methoxypyridin-3-yl)methyl)-3,5-dimethylpiperazin-1-yl)pyridin-3-yl)-N-(5-methyl-1H-pyrazol-3-yl)quinazolin-4-amine; <36> (R)-2-(6-(4-((6-methoxypyridin-3-yl)methyl)-3-methylpiperazin-1-yl)pyridin-3-yl)-N-(5-methyl-1H-pyrazol-3-yl)quinazolin-4-amine; and <37> 2-(6-(4-((6-methoxypyridin-3-yl)methyl)-4,7-diazaspiro[2.5]octan-7-yl)pyridin-3-yl)-N-(5-methyl-1H-pyrazol-3-yl)quinazolin-4-amine.

5. A pharmaceutical composition containing the compound of Chemical Formula 1, the stereoisomer thereof, the solvate thereof, the hydrate thereof, or the pharmaceutically acceptable salt thereof of claim 1 as an active ingredient and an excipient.

6. A method for treatment of cancer, comprising, administering the compound of Chemical Formula 1, a stereoisomer thereof, a solvate thereof, a hydrate thereof, or a pharmaceutically acceptable salt thereof defined in claim 1 as an active ingredient to a subject in need thereof wherein the cancer expresses a RET fusion gene.

7. The method of claim 6, wherein the cancer is one or more selected from the group consisting of pseudomyxoma, intrahepatic cholangiocarcinoma, hepatoblastoma, liver cancer, thyroid cancer, medullary thyroid carcinoma, colon cancer, testicular cancer, myelodysplastic syndrome, glioblastoma, oral cancer, lip cancer, mycosis fungoides, acute myelogenous leukemia, acute lymphoblastic leukemia, basal cell carcinoma, ovarian epithelial cancer, ovarian germ cell cancer, male breast cancer, brain cancer, pituitary adenoma, multiple myeloma, gallbladder cancer, bile duct cancer, colorectal cancer, chronic myelogenous leukemia, chronic lymphocytic leukemia, retinoblastoma, choroidal melanoma, ampulla of Vater cancer, bladder cancer, peritoneal cancer, parathyroid cancer, adrenal gland cancer, paranasal sinus cancer, non-small-cell lung cancer, tongue cancer, astrocytoma, small cell lung cancer, pediatric brain cancer, pediatric lymphoma, pediatric leukemia, small intestine cancer, meningioma, esophageal cancer, neuroglioma, renal pelvic cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urothelial cancer, cancer of unknown primary site, gastric lymphoma, gastric cancer, gastric carcinoid tumors, gastrointestinal stromal cancer, Wilm's cancer, breast cancer, sarcoma, penile cancer, pharynx cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoid tumors, vaginal cancer, spinal cord cancer, acoustic neurinoma, pancreatic cancer, salivary gland cancer, Kaposi's sarcoma, Paget's disease, tonsil cancer, squamous cell cancer, lung adenocarcinoma, lung cancer, lung squamous cell cancer, skin cancer, anal cancer, rhabdomyosarcoma, laryngeal cancer, pleural cancer, blood cancer, and thymus cancer.

8. A method for treatment of cancer, comprising administering the compound of Chemical Formula 1, a stereoisomer thereof, a solvate thereof, a hydrate thereof, or a pharmaceutically acceptable salt thereof defined in claim 1 as an active ingredient to a subject in need thereof, wherein the cancer expresses a RET fusion gene and the cancer is medullary thyroid cancer or lung cancer.

* * * * *

UNITED STATES PATENT AND TRADEMARK OFFICE
CERTIFICATE OF CORRECTION

PATENT NO. : 12,281,121 B2
APPLICATION NO. : 17/612757
DATED : April 22, 2025
INVENTOR(S) : Jo et al.

It is certified that error appears in the above-identified patent and that said Letters Patent is hereby corrected as shown below:

In the Specification

Column 7, Line 41: Please correct "$C_1$" to read --Cl--

Column 7, Line 57: Please correct "cyclo propylethyl" to read --cyclopropylethyl--

Column 7, Lines 58-59: Please correct "cycloheptylmethyl" to read --cyclopentylmethyl--

Column 8, Lines 20-21: Please correct "(1 S,4S)-2-azabicyclo[2.2.2]octane" to read --(1S,4S)-2-azabicyclo[2.2.2]octane--

Column 19, Lines 61-64: Please correct "tert-butyl 3-(5-(44(5-methyl-1-(tetrahydro-2*H*-pyran-2-yl)-1*H*-pyrazol-3-yl)amino)furo[3,2-*d*]pyrimidin-2-yl)pyridine-2-yl)-3,6-diazabicyclo[3.1.1]heptane-6-carboxylate" to read --tert-butyl 3-(5-(4-((5-methyl-1-(tetrahydro-2*H*-pyran-2-yl)-1*H*-pyrazol-3-yl)amino)furo[3,2-*d*]pyrimidin-2-yl)pyridine-2-yl)-3,6-diazabicyclo[3.1.1]heptane-6-carboxylate--

Columns 21-40, Table 1: Please correct delete Table 1 and replace with the following:
--Table 1

Signed and Sealed this
Ninth Day of September, 2025

Coke Morgan Stewart
*Acting Director of the United States Patent and Trademark Office*

| Example compound | Structure | Name of compound | ¹H NMR | LC-MS (m/z) |
|---|---|---|---|---|
| 1 | 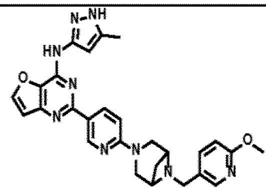 | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)furo[3,2-d]pyrimidin-4-amine | ¹H NMR (400 MHz, DMSO-$d_6$) δ = 12.11 (br s, 1H), 10.14 (br s, 1H), 9.13 (d, $J$ = 2.0 Hz, 1H), 8.46 (dd, $J$ = 2.0, 8.8 Hz, 1H), 8.26 (s, 1H), 8.07 (d, $J$ = 2.0 Hz, 1H), 7.67 (dd, $J$ = 2.4, 8.8 Hz, 1H), 7.05 (s, 1H), 6.76 (dd, $J$ = 6.0, 8.8 Hz, 2H), 6.61 (br s, 1H), 3.82 (s, 3H), 3.75 (br d, $J$ = 12.0 Hz, 2H), 3.66 (br d, $J$ = 5.6 Hz, 2H), 3.61 - 3.42 (m, 4H), 2.54 - 2.51 (m, 1H), 2.31 (s, 3H), 1.56 (br d, $J$ = 8.4 Hz, 1H) | 510.4 [M+H]⁺ |
| 2 | 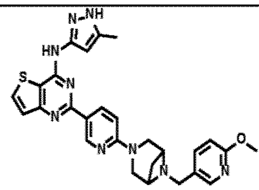 | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)thieno[3,2-d]pyrimidin-4-amine | ¹H NMR (400 MHz, DMSO-$d_6$) δ = 11.52 (s, 1H), 9.23 (d, $J$ = 2.2 Hz, 1H), 8.71 (dd, $J$ = 9.2, 2.3 Hz, 1H), 8.43 (d, $J$ = 5.5 Hz, 2H), 8.07 (ddd, $J$ = 8.3, 5.6, 2.4 Hz, 1H), 7.76 (d, $J$ = 5.5 Hz, 1H), 7.02 (d, $J$ = 9.3 Hz, 1H), 6.92 (d, $J$ = 7.0 Hz, 1H), 6.47 (s, 1H), 4.62 (dd, $J$ = 23.4, 5.9 Hz, 2H), 4.48 - 4.42 (m, 2H), 4.26 (s, 2H), 4.15 (s, 2H), 3.89 (s, 3H), 2.35 (s, 3H) | 526.3 [M+H]⁺ |
| 3 | 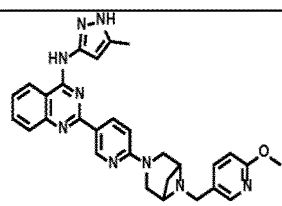 | 2-(6-(6-((6-methoxypyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-$d_6$) δ = 12.23 (br s, 1H), 10.29 (br s, 1H), 9.24 (d, $J$ = 2.0 Hz, 1H), 8.67 - 8.49 (m, 2H), 8.06 (s, 1H), 7.77 (br d, $J$ = 2.0 Hz, 2H), 7.65 (br d, $J$ = 8.4 Hz, 1H), 7.52 - 7.41 (m, 1H), 6.84 - 6.68 (m, 3H), 3.81 (s, 3H), 3.75 (br d, $J$ = 11.2 Hz, 2H), 3.64 (br d, $J$ = 5.6 Hz, 2H), 3.60 - 3.45 (m, 4H), 2.53 - 2.51 (m, 1H), 2.35 (s, 3H), 1.55 (br d, $J$ = 8.4 Hz, 1H) | 520.3 [M+H]⁺ |
| 4 | 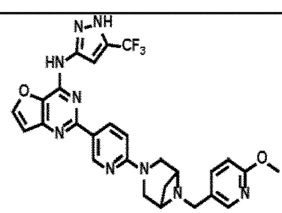 | 2-(6-(6-((6-methoxypyridin-3-yl)methyl)-3,6-diazabicyclo[3.1.1]heptan-3-yl)pyridin-3-yl)-N- | ¹H NMR (400 MHz, DMSO-$d_6$) δ = 9.11 (d, $J$ = 2.4 Hz, 1H), 8.65 (d, $J$ = 2.2 Hz, 1H), 8.45 (d, $J$ = 9.1 Hz, 1H), 8.07 (s, 1H), 7.95 (s, 2H), 7.68 (d, $J$ = 8.7 Hz, 1H), 7.32 (d, $J$ = 2.1 Hz, 1H), 7.25 (s, 2H), 6.86 (d, $J$ = 9.0 Hz, 1H), 6.77 (d, $J$ = 8.4 Hz, 1H), 6.67 (s, 1H), 3.82 (s, 3H), 3.81 - 3. | 564.3 [M+H]⁺ |

| | | | | |
|---|---|---|---|---|
| | | (5-(trifluoromethyl)-1*H*-pyrazol-3-yl)furo[3,2-d]pyrimidin-4-amine | 79 (m, 2H), 3.78 – 3.74 (m, 2H), 3.68 (dd, $J$ = 6.0, 1.8 Hz, 2H), 2.69 – 2.66 (m, 1H), 1.47 (d, $J$ = 6.9 Hz, 1H) | |
| 5 | | *N*-(5-methyl-1*H*-pyrazol-3-yl)-2-(6-(6-((5-methylthiazol-2-yl)methyl)-3,6-diazabicyclo[3.1.1]heptan-3-yl)pyridin-3-yl)quinazolin-4-amine | $^1$H NMR (400 MHz, DMSO-d$_6$) δ = 10.34 (s, 1H), 9.23 (d, $J$ = 2.2 Hz, 1H), 8.64 – 8.51 (m, 2H), 7.83 – 7.72 (m, 2H), 7.47 (ddd, $J$ = 8.2, 6.0, 2.2 Hz, 1H), 7.35 (d, $J$ = 1.2 Hz, 1H), 6.80 (d, $J$ = 9.0 Hz, 1H), 6.73 (s, 1H), 3.81 – 3.73 (m, 6H), 3.60 (d, $J$ = 11.7 Hz, 2H), 2.56 (dd, $J$ = 11.6, 3.6 Hz, 1H), 2.41 (d, $J$ = 1.0 Hz, 3H), 2.35 (s, 3H), 1.62 (d, $J$ = 8.5 Hz, 1H) | 510.4 [M+H]$^+$ |
| 6 | | 2-(6-(3-((6-methoxypyridin-3-yl)methyl)-3,6-diazabicyclo[3.1.1]heptan-6-yl)pyridin-3-yl)-*N*-(5-methyl-1*H*-pyrazol-3-yl)quinazolin-4-amine | $^1$H NMR (400 MHz, DMSO-d$_6$) δ = 11.91 (s, 1H), 10.32 (s, 1H), 9.24 (d, $J$ = 2.1 Hz, 1H), 8.61 (d, $J$ = 8.3 Hz, 1H), 8.57 (dd, $J$ = 8.9, 2.2 Hz, 1H), 7.78 (dd, $J$ = 4.6, 1.1 Hz, 2H), 7.60 (d, $J$ = 6.9 Hz, 1H), 7.48 (d, $J$ = 6.2 Hz, 1H), 6.80 (d, $J$ = 9.0 Hz, 1H), 6.73 (s, 1H), 6.37 (s, 1H), 6.20 (dd, $J$ = 6.9, 1.4 Hz, 1H), 4.53 (d, $J$ = 6.1 Hz, 1H), 4.00 (dd, $J$ = 34.3, 12.5 Hz, 2H), 3.78 (d, $J$ = 22.3 Hz, 2H), 3.73 (s, 2H), 3.62 (dd, $J$ = 13.2, 6.6 Hz, 2H), 2.63 (s, 1H), 2.35 (s, 3H), 1.64 (d, $J$ = 6.9 Hz, 1H) | 520.4 [M+H]$^+$ |
| 7 | | 2-(6-(6-((6-methoxypyridin-3-yl)methyl)-3,6-diazabicyclo[3.1.1]heptan-3-yl)pyridin-3-yl)-*N*-(5-methyl-1*H*-pyrazol-3-yl)-6,7-dihydro-5*H*-cyclopenta[*d*]pyrimidin-4-amine | $^1$H NMR (400 MHz, DMSO-d6) δ 10.90 (s, 1H), 9.19 (dd, $J$ = 22.3, 2.5 Hz, 1H), 8.67 (dd, $J$ = 24.6, 9.5 Hz, 1H), 8.46 (dd, $J$ = 36.6, 2.5 Hz, 1H), 8.14 – 8.02 (m, 1H), 7.05 (dd, $J$ = 42.7, 9.4 Hz, 1H), 6.91 (dd, $J$ = 8.6, 7.2 Hz, 1H), 6.51 (d, $J$ = 4.7 Hz, 1H), 4.64 (d, $J$ = 6.1 Hz, 1H), 4.56 (d, $J$ = 6.2 Hz, 1H), 4.44 (d, $J$ = 6.4 Hz, 2H), 4.26 – 4.05 (m, 6H), 3.88 (d, $J$ = 6.8 Hz, 3H), 3.13 (q, $J$ = 7.8 Hz, 2H), 2.88 (s, 2H), 2.33 (d, $J$ = 5.6 Hz, 3H), 2.16 (s, 2H) | 510.3 [M+H]$^+$ |
| 8 | | *N*-(5-methyl-1*H*-pyrazol-3-yl)-2-(6-(6-((6-(trifluoromethyl)pyridin-3-yl)methyl)-3,6-diazabicyclo[3.1.1]heptan-3- | $^1$H NMR (400 MHz, DMSO-d6) δ 12.22 (s, 1H), 10.30 (s, 1H), 9.24 (d, $J$ = 2.3 Hz, 1H), 8.75 (d, $J$ = 2.1 Hz, 1H), 8.62 – 8.54 (m, 2H), 8.06 (dd, $J$ = 8.0, 2.1 Hz, 1H), 7.84 (d, $J$ = 8.0 Hz, 1H), 7.79 – 7.74 (m, 2H), 7.47 (ddd, $J$ = 8.3, 6.1, 2.1 Hz, 1H), 6.82 (d, $J$ = 9.0 Hz, 1H), 6.73 (s, 1H), 3.79 – 3.59 | 558.5 [M+H]$^+$ |

| | | | | |
|---|---|---|---|---|
| | | yl)pyridin-3-yl)quinazolin-4-amine | (m, 8H), 2.58 (d, J = 7.0 Hz, 1H), 2.34 (s, 3H), 1.62 (d, J = 8.4 Hz, 1H) | |
| 9 | 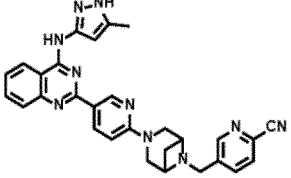 | 5-((3-(5-(4-((5-methyl-1H-pyrazol-3-yl)amino)quinazolin-2-yl)pyridin-2-yl)-3,6-diazabicyclo[3.1.1]heptan-6-yl)methyl)picolinonitrile | ¹H NMR (400 MHz, DMSO-d6) δ 12.22 (s, 1H), 10.30 (s, 1H), 9.23 (d, J = 2.3 Hz, 1H), 8.74 (dd, J = 2.1, 0.9 Hz, 1H), 8.62 - 8.54 (m, 2H), 8.05 - 7.95 (m, 2H), 7.81 - 7.74 (m, 2H), 7.47 (ddd, J = 8.3, 6.2, 2.0 Hz, 1H), 6.81 (d, J = 9.0 Hz, 1H), 6.73 (s, 1H), 3.81 - 3.56 (m, 8H), 2.58 (d, J = 7.0 Hz, 1H), 2.34 (s, 3H), 1.61 (d, J = 8.4 Hz, 1H) | 515.5 [M+H]+ |
| 10 | 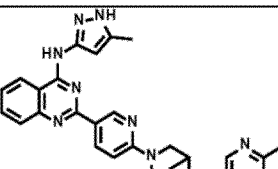 | N-(5-methyl-1H-pyrazol-3-yl)-2-(6-(6-((6-methylpyridin-3-yl)methyl)-3,6-diazabicyclo[3.1.1]heptan-3-yl)pyridin-3-yl)quinazolin-4-amine | ¹H NMR (400 MHz, DMSO-d6) δ 12.22 (s, 1H), 10.30 (s, 1H), 9.23 (d, J = 2.3 Hz, 1H), 8.62 - 8.54 (m, 2H), 8.38 (d, J = 2.3 Hz, 1H), 7.81 - 7.74 (m, 2H), 7.63 (dd, J = 7.9, 2.3 Hz, 1H), 7.47 (ddd, J = 8.3, 6.1, 2.1 Hz, 1H), 7.18 (d, J = 7.8 Hz, 1H), 6.81 (d, J = 9.0 Hz, 1H), 6.73 (s, 1H), 3.77 (d, J = 12.2 Hz, 2H), 3.69 (d, J = 5.9 Hz, 2H), 3.58 (d, J = 25.7 Hz, 4H), 2.43 (s, 3H), 2.41 (d, J = 3.5 Hz, 1H), 2.35 (s, 3H), 1.59 (d, J = 8.4 Hz, 1H) | 504.5 [M+H]+ |
| 11 | 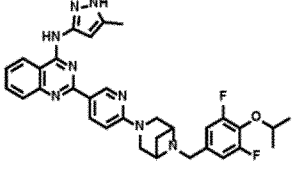 | 2-(6-(6-(3,5-difluoro-4-isopropoxybenzyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d6) δ 12.19 (s, 1H), 10.30 (s, 1H), 9.23 (d, J = 2.3 Hz, 1H), 8.63 - 8.53 (m, 2H), 7.81 - 7.74 (m, 2H), 7.47 (ddd, J = 8.3, 6.1, 2.1 Hz, 1H), 7.15 - 7.08 (m, 2H), 6.80 (d, J = 9.0 Hz, 1H), 6.73 (s, 1H), 4.32 (hept, J = 6.1 Hz, 1H), 3.72 (d, J = 6.0 Hz, 4H), 3.53 (s, 2H), 3.33 (s, 2H), 2.57 (d, J = 6.9 Hz, 1H), 2.34 (s, 3H), 1.59 (d, J = 8.4 Hz, 1H), 1.26 (d, J = 6.1 Hz, 6H) | 583.5 [M+H]+ |
| 12 | 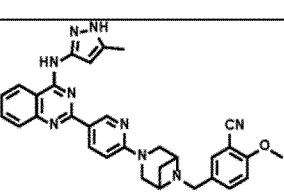 | 2-methoxy-5-((3-(5-(4-((5-methyl-1H-pyrazol-3-yl)amino)quinazolin-2-yl)pyridin-2-yl)-3,6-diazabicyclo[3.1.1]heptan-6-yl)methyl)benzonitrile | ¹H NMR (400 MHz, DMSO-d6) δ 12.21 (s, 1H), 10.30 (s, 1H), 9.23 (d, J = 2.3 Hz, 1H), 8.64 - 8.52 (m, 2H), 7.81 - 7.73 (m, 2H), 7.68 - 7.61 (m, 2H), 7.47 (ddd, J = 8.3, 6.1, 2.1 Hz, 1H), 7.18 (d, J = 8.6 Hz, 1H), 6.81 (d, J = 8.9 Hz, 1H), 6.73 (s, 1H), 3.89 (s, 3H), 3.75 (d, J = 12.1 Hz, 2H), 3.68 (d, J = 5.9 Hz, 2H), 3.33 (s, 2H), 2.58 - 2.53 (m, 1H), 2.35 (s, 3H), 1.58 (d, J = 8.4 Hz, 1H) | 544.5 [M+H]+ |

| 13 | 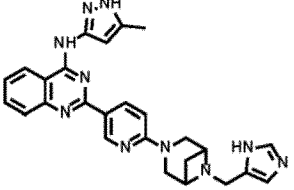 | 2-(6-(6-((1H-imidazol-5-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, MeOD) δ = 9.19 (d, J = 2.1 Hz, 1H), 8.55 (dd, J = 9.0, 2.2 Hz, 1H), 8.26 (d, J = 8.2 Hz, 1H), 7.84 - 7.75 (m, 3H), 7.54 - 7.47 (m, 1H), 7.25 (s, 1H), 6.80 (d, J = 9.0 Hz, 1H), 6.68 (s, 1H), 4.46 - 4.10 (m, 3H), 4.06 - 3.95 (m, 5H), 2.39 (s, 3H) | 479.4 [M+H]⁺ |
| 14 | 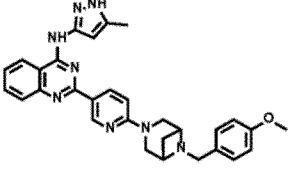 | 2-(6-(6-(4-methoxybenzyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d₆) δ = 10.54 (s, 1H), 9.25 (d, J = 2.2 Hz, 1H), 8.64 (d, J = 8.2 Hz, 1H), 8.57 (dd, J = 8.9, 2.3 Hz, 1H), 7.81 - 7.74 (m, 2H), 7.47 (ddd, J = 8.2, 5.8, 2.3 Hz, 1H), 7.24 (d, J = 8.6 Hz, 2H), 6.86 (d, J = 8.7 Hz, 2H), 6.80 (d, J = 9.0 Hz, 1H), 6.74 (s, 1H), 3.76 (d, J = 2.5 Hz, 1H), 3.72 (s, 3H), 3.65 (d, J = 5.9 Hz, 2H), 3.57 (s, 2H), 3.48 (s, 2H), 2.54 (d, J = 2.7 Hz, 1H), 2.34 (s, 3H), 1.83 (s, 2H), 1.57 (d, J = 8.4 Hz, 1H) | 519.4 [M+H]⁺ |
| 15 | 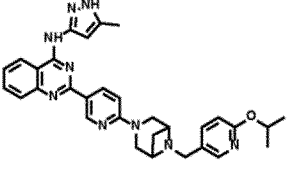 | 2-(6-(6-((6-isopropoxypyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, MeOD) δ = 9.20 (s, 1H), 8.55 (d, J = 8.4 Hz, 1H), 8.25 (d, J = 7.4 Hz, 1H), 8.09 (s, 1H), 7.83 - 7.73 (m, 2H), 7.68 (d, J = 7.7 Hz, 1H), 7.49 (t, J = 7.0 Hz, 1H), 6.78 (d, J = 8.9 Hz, 1H), 6.71 (d, J = 8.4 Hz, 2H), 5.20 (dt, J = 12.3, 6.1 Hz, 1H), 3.93 (d, J = 12.8 Hz, 4H), 3.76 (s, 4H), 2.38 (s, 3H), 1.32 (d, J = 6.2 Hz, 6H) | 548.4 [M+H]⁺ |
| 16 | 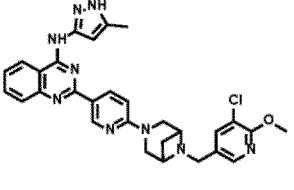 | 2-(6-(6-((5-chloro-6-methoxypyridin-3-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, DMSO-d₆) δ = 10.47 (s, 1H), 9.23 (s, 1H), 8.59 (dd, J = 25.6, 8.5 Hz, 2H), 8.08 (s, 1H), 7.86 (s, 1H), 7.77 (t, J = 7.3 Hz, 2H), 7.47 (t, J = 6.6 Hz, 1H), 6.82 (d, J = 8.9 Hz, 1H), 6.72 (s, 1H), 3.92 (s, 3H), 3.77 (d, J = 11.4 Hz, 2H), 3.70 (d, J = 5.3 Hz, 2H), 3.60 (d, J = 16.5 Hz, 2H), 3.53 (s, 2H), 2.57 - 2.52 (m, 1H), 2.33 (s, 3H), 1.58 (d, J = 8.1 Hz, 1H) | 555.4 [M+H]⁺ |
| 17 | 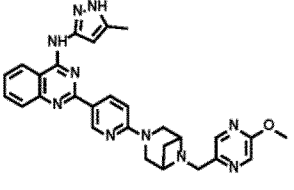 | 2-(6-(6-((5-methoxypyrazin-2-yl)methyl)-3,6-diazabicyclo[3.1.1]heptan-3-yl)pyridin-3-yl)-N-(5-methyl-1H-pyrazol-3-yl)quinazolin-4-amine | ¹H NMR (400 MHz, MeOD) δ = 9.18 (d, J = 1.8 Hz, 1H), 8.52 (dd, J = 8.9, 1.8 Hz, 1H), 8.23 (d, J = 8.1 Hz, 1H), 8.13 (d, J = 2.8 Hz, 2H), 7.82 - 7.73 (m, 2H), 7.48 (t, J = 7.0 Hz, 1H), 6.75 (d, J = 9.0 Hz, 1H), 6.69 (s, 1H), 3.98 (d, J = 12.2 Hz, 2H), 3.94 (s, 3H), 3.90 (d, J = 5.4 Hz, 2H) | 521.4 [M+H]⁺ |

| | | | | |
|---|---|---|---|---|
| | | pyrazol-3-yl)quinazolin-4-amine | , 3.75 (s, 2H), 3.67 (d, J = 11.9 Hz, 2H), 2.72 (s, 1H), 2.38 (s, 3H), 1.71 (d, J = 9.0 Hz, 1H) | |
| 18 | | N-(5-methyl-1H-pyrazol-3-yl)-2-(6-(6-(quinolin-6-ylmethyl)-3,6-diazabicyclo[3.1.1]heptan-3-yl)pyridin-3-yl)quinazolin-4-amine | $^1$H NMR (400 MHz, DMSO-d$_6$) δ = 11.97 (s, 1H), 10.31 (s, 1H), 9.26 (d, J = 2.1 Hz, 1H), 8.86 (dd, J = 4.1, 1.6 Hz, 1H), 8.64 – 8.55 (m, 2H), 8.34 (d, J = 7.6 Hz, 1H), 7.96 (d, J = 8.7 Hz, 1H), 7.91 (s, 1H), 7.77 (dd, J = 10.3, 3.7 Hz, 3H), 7.53 – 7.44 (m, 2H), 6.83 (d, J = 9.0 Hz, 1H), 6.74 (s, 1H), 3.82 (d, J = 11.4 Hz, 2H), 3.76 (d, J = 5.8 Hz, 4H), 3.61 (d, J = 8.8 Hz, 2H), 2.60 (dd, J = 12.9, 6.3 Hz, 1H), 2.35 (s, 3H), 1.62 (d, J = 8.4 Hz, 1H) | 540.4 [M+H]$^+$ |
| 19 | | N-(5-methyl-1H-pyrazol-3-yl)-2-(6-(6-((4-methylthiazol-2-yl)methyl)-3,6-diazabicyclo[3.1.1]heptan-3-yl)pyridin-3-yl)quinazolin-4-amine | $^1$H NMR (400 MHz, DMSO-d$_6$) δ = 10.46 (s, 1H), 9.24 (d, J = 2.2 Hz, 1H), 8.62 (d, J = 8.3 Hz, 1H), 8.57 (dd, J = 8.9, 2.3 Hz, 1H), 7.82 – 7.74 (m, 2H), 7.47 (ddd, J = 8.2, 6.0, 2.2 Hz, 1H), 7.15 (d, J = 0.9 Hz, 1H), 6.81 (d, J = 9.0 Hz, 1H), 6.73 (s, 1H), 3.83 – 3.72 (m, 6H), 3.61 (d, J = 11.4 Hz, 2H), 2.59 (dd, J = 13.5, 6.4 Hz, 1H), 2.34 (s, 3H), 2.30 (d, J = 0.7 Hz, 3H), 1.62 (d, J = 8.6 Hz, 1H) | 510.4 [M+H]$^+$ |
| 20 | | 2-(6-(6-((6-(dimethylamino)pyridin-3-yl)methyl)-3,6-diazabicyclo[3.1.1]heptan-3-yl)pyridin-3-yl)-N-(5-methyl-1H-pyrazol-3-yl)quinazolin-4-amine | $^1$H NMR (400 MHz, DMSO-d$_6$) δ = 11.49 (s, 1H), 9.63 (s, 1H), 9.19 (s, 1H), 8.75 (d, J = 7.4 Hz, 1H), 8.55 (d, J = 8.9 Hz, 1H), 8.28 (s, 1H), 7.98 (d, J = 5.4 Hz, 2H), 7.81 (d, J = 9.5 Hz, 1H), 7.68 (t, J = 6.6 Hz, 1H), 6.93 (dd, J = 17.3, 8.9 Hz, 2H), 6.67 (s, 1H), 4.59 (s, 2H), 4.47 (d, J = 5.6 Hz, 2H), 4.17 (d, J = 8.8 Hz, 2H), 3.99 (d, J = 12.8 Hz, 2H), 3.52 (d, J = 5.0 Hz, 1H), 3.12 (s, 6H), 2.36 (s, 3H), 2.07 – 2.01 (m, 1H) | 533.4 [M+H]$^+$ |
| 21 | | N-(4-((3-(5-(4-((5-methyl-1H-pyrazol-3-yl)amino)quinazolin-2-yl)pyridin-2-yl)-3,6-diazabicyclo[3.1.1]heptan-6-yl)methyl)phenyl)methanesulfonamide | $^1$H NMR (400 MHz, DMSO-d$_6$) δ = 11.25 (s, 1H), 10.03 (s, 1H), 9.60 (s, 1H), 9.20 (d, J = 1.8 Hz, 1H), 8.73 (s, 1H), 8.56 (dd, J = 9.1, 2.0 Hz, 1H), 7.94 (s, 2H), 7.64 (d, J = 6.4 Hz, 1H), 7.54 (d, J = 8.4 Hz, 2H), 7.27 (s, 2H), 6.93 (d, J = 9.1 Hz, 1H), 6.67 (s, 1H), 4.64 (d, J = 5.5 Hz, 2H), 4.46 (d, J = 6.0 Hz, 2H), 4.15 (d, J = 10.1 Hz, 2H), 3.98 (d, J = 12.8 Hz, 2H), 3.05 (s, 3H), 2.35 (s, 3H), 2.04 (d, J = 7.8 Hz, 1H) | 582.4 [M+H]$^+$ |

| 22 | 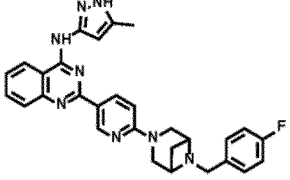 | 2-(6-(6-(4-fluorobenzyl)-3,6-diazabicyclo[3.1.1]heptan-3-yl)pyridin-3-yl)-N-(5-methyl-1H-pyrazol-3-yl)quinazolin-4-amine | $^1$H NMR (400 MHz, DMSO-d$_6$) δ = 11.90 (s, 1H), 10.31 (s, 1H), 9.25 (d, J = 2.2 Hz, 1H), 8.65 - 8.52 (m, 2H), 7.78 (d, J = 6.0 Hz, 2H), 7.47 (ddd, J = 8.2, 5.9, 2.3 Hz, 1H), 7.39 (dd, J = 8.3, 5.8 Hz, 2H), 7.13 (t, J = 8.8 Hz, 2H), 6.80 (d, J = 9.0 Hz, 1H), 6.74 (s, 1H), 3.76 (d, J = 13.7 Hz, 4H), 3.60 (s, 4H), 2.58 (s, 1H), 2.35 (s, 3H), 1.61 (d, J = 8.4 Hz, 1H) | 507.5 [M+H]$^+$ |
| 23 | 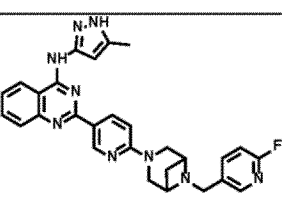 | 2-(6-(6-((6-fluoropyridin-3-yl)methyl)-3,6-diazabicyclo[3.1.1]heptan-3-yl)pyridin-3-yl)-N-(5-methyl-1H-pyrazol-3-yl)quinazolin-4-amine | $^1$H NMR (400 MHz, DMSO-d$_6$) δ = 11.93 (s, 1H), 10.31 (s, 1H), 9.25 (d, J = 2.2 Hz, 1H), 8.63 - 8.53 (m, 2H), 8.19 (s, 1H), 7.96 (td, J = 8.3, 2.4 Hz, 1H), 7.78 (t, J = 6.1 Hz, 2H), 7.48 (ddd, J = 8.2, 5.8, 2.3 Hz, 1H), 7.12 (dd, J = 8.4, 2.8 Hz, 1H), 6.81 (d, J = 9.0 Hz, 1H), 6.74 (s, 1H), 3.75 (dd, J = 22.7, 8.8 Hz, 4H), 3.61 (s, 4H), 2.56 (d, J = 5.7 Hz, 1H), 2.34 (d, J = 9.2 Hz, 3H), 1.60 (d, J = 8.4 Hz, 1H) | 508.4 [M+H]$^+$ |
| 24 | 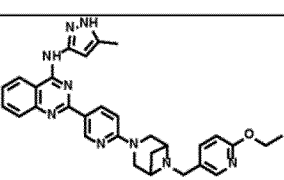 | 2-(6-(6-((6-ethoxypyridin-3-yl)methyl)-3,6-diazabicyclo[3.1.1]heptan-3-yl)pyridin-3-yl)-N-(5-methyl-1H-pyrazol-3-yl)quinazolin-4-amine | $^1$H NMR (400 MHz, DMSO-d$_6$) δ = 12.02 (s, 1H), 10.35 (s, 1H), 9.27 (d, J = 2.1 Hz, 1H), 8.65 - 8.56 (m, 2H), 8.23 (s, 1H), 7.83 - 7.76 (m, 3H), 7.49 (ddd, J = 8.2, 6.0, 2.2 Hz, 1H), 6.84 (t, J = 9.7 Hz, 2H), 6.73 (s, 1H), 4.31 (q, J = 7.0 Hz, 2H), 4.25 - 4.05 (m, 2H), 3.92 (s, 3H), 2.36 (s, 3H), 1.32 (t, J = 7.0 Hz, 3H) | 534.5 [M+H]$^+$ |
| 25 | 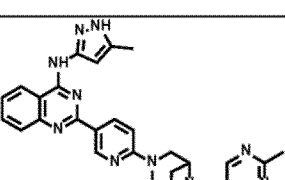 | N-(5-methyl-1H-pyrazol-3-yl)-2-(6-(6-((2-methylpyrimidin-5-yl)methyl)-3,6-diazabicyclo[3.1.1]heptan-3-yl)pyridin-3-yl)quinazolin-4-amine | $^1$H NMR (400 MHz, DMSO-d$_6$) δ = 12.10 (s, 1H), 10.66 (s, 1H), 9.25 (s, 1H), 8.87 (d, J = 6.3 Hz, 1H), 8.68 - 8.56 (m, 2H), 7.84 (q, J = 8.4 Hz, 2H), 7.54 (dd, J = 10.5, 4.1 Hz, 1H), 6.90 (d, J = 9.0 Hz, 1H), 6.71 (s, 1H), 4.74 (s, 1H), 4.55 (s, 2H), 4.02 (dd, J = 37.3, 15.8 Hz, 4H), 2.66 (s, 3H), 2.36 (s, 3H) | 505.5 [M+H]$^+$ |
| 26 | 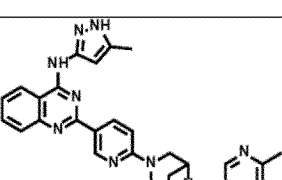 | N-(5-methyl-1H-pyrazol-3-yl)-2-(6-(6-((5-methylpyrazin-2-yl)methyl)-3,6-diazabicyclo[3.1.1]heptan-3-yl)pyridin-3- | $^1$H NMR (400 MHz, DMSO-d$_6$) δ = 11.84 (s, 1H), 10.32 (d, J = 12.0 Hz, 1H), 9.25 (t, J = 4.0 Hz, 1H), 8.63 - 8.54 (m, 3H), 8.42 (s, 1H), 7.82 - 7.74 (m, 2H), 7.47 (ddd, J = 8.2, 5.9, 2.2 Hz, 1H), 6.81 (d, J = 9.0 Hz, 1H), 6.74 (s, 1H), 3.86 (d, J = 11.7 Hz, 2H), 3.75 (d, J = 5.7 Hz, 2H), 3.68 (s, 2H), 3.64 - 3.55 (m, 2H), 2.58 - 2.52 (m, | 505.5 [M+H]$^+$ |

| # | Structure | Name | ¹H NMR | MS |
|---|---|---|---|---|
| | | yl)quinazolin-4-amine | 1H), 2.47 (s, 3H), 2.35 (s, 3H), 1.61 (d, J = 8.4 Hz, 1H) | |
| 27 | 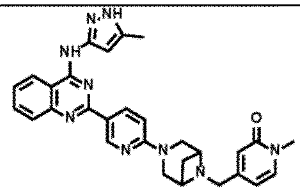 | 1-methyl-4-((3-(5-(4-((5-methyl-1H-pyrazol-3-yl)amino)quinazolin-2-yl)pyridin-2-yl)-3,6-diazabicyclo[3.1.1]heptan-6-yl)methyl)pyridin-2(1H)-one | ¹H NMR (400 MHz, DMSO-d6) δ 12.21 (s, 1H), 10.31 (s, 1H), 9.14 (dd, J = 2.3, 0.8 Hz, 1H), 8.61 (d, J = 8.3 Hz, 1H), 8.48 (dd, J = 8.7, 2.3 Hz, 1H), 7.86 – 7.84 (m, 1H), 7.81 – 7.76 (m, 2H), 7.48 (ddd, J = 8.3, 6.2, 2.0 Hz, 1H), 7.18 (dd, J = 8.5, 2.4 Hz, 1H), 6.72 (s, 1H), 6.56 (ddd, J = 13.8, 8.6, 0.7 Hz, 2H), 4.40 (d, J = 5.8 Hz, 2H), 3.70 (s, 3H), 3.43 (s, 2H), 3.14 (d, J = 10.6 Hz, 2H), 2.73 (d, J = 10.4 Hz, 2H), 2.58 – 2.53 (m, 1H), 2.34 (s, 3H), 1.84 (d, J = 7.7 Hz, 1H) | 520.5 [M+H]+ |
| 28 | 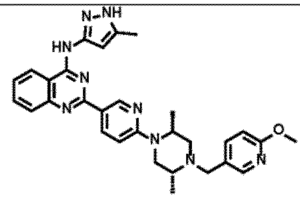 | 2-(6-((2S,5R)-4-((6-methoxypyridin-3-yl)methyl)-2,5-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.27 (s, 1H), 9.13 (d, J = 2.4 Hz, 1H), 8.59 (d, J = 8.3 Hz, 1H), 8.47 (dd, J = 9.0, 2.4 Hz, 1H), 8.11 (d, J = 2.4 Hz, 1H), 7.79 – 7.70 (m, 3H), 7.46 (ddd, J = 8.3, 6.4, 1.8 Hz, 1H), 6.90 – 6.74 (m, 3H), 4.58 (s, 1H), 4.17 – 4.07 (m, 1H), 3.85 (s, 3H), 3.83 (s, 1H), 3.61 (d, J = 13.5 Hz, 1H), 3.45 (d, J = 13.5 Hz, 1H), 3.30 (d, J = 3.7 Hz, 1H), 3.10 (d, J = 6.8 Hz, 1H), 2.77 (dd, J = 11.7, 4.2 Hz, 1H), 2.34 (s, 3H), 1.17 (d, J = 6.5 Hz, 3H), 1.01 – 0.99 (m, 3H) | 536.5 [M+H]+ |
| 29 | 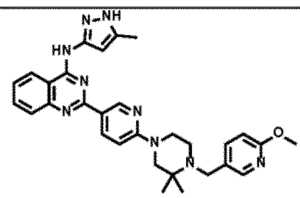 | 2-(6-(4-((6-methoxypyridin-3-yl)methyl)-3,3-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.28 (s, 1H), 9.12 (d, J = 2.4 Hz, 1H), 8.59 (d, J = 8.3 Hz, 1H), 8.46 (dd, J = 9.0, 2.4 Hz, 1H), 8.08 (d, J = 2.3 Hz, 1H), 7.81 – 7.71 (m, 2H), 7.67 (dd, J = 8.5, 2.4 Hz, 1H), 7.46 (ddd, J = 8.2, 6.4, 1.8 Hz, 1H), 6.96 (d, J = 9.1 Hz, 1H), 6.80 (dd, J = 8.5, 0.7 Hz, 1H), 6.71 (s, 1H), 3.84 (s, 3H), 3.58 (d, J = 5.7 Hz, 2H), 3.48 (d, J = 15.3 Hz, 4H), 2.43 (t, J = 5.3 Hz, 2H), 2.33 (s, 3H), 1.15 (s, 6H) | 536.5 [M+H]+ |
| 30 | 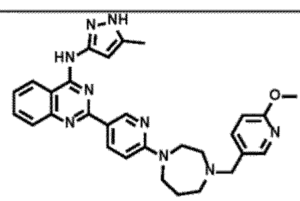 | 2-(6-(4-((6-methoxypyridin-3-yl)methyl)-1,4-diazepan-1-yl)pyridin-3-yl)-N-(5-methyl-1H-pyrazol-3- | ¹H NMR (400 MHz, DMSO-d6) δ 12.20 (s, 1H), 10.26 (s, 1H), 9.16 – 9.10 (m, 1H), 8.58 (d, J = 8.3 Hz, 1H), 8.47 (dd, J = 9.0, 2.4 Hz, 1H), 8.07 – 8.00 (m, 1H), 7.80 – 7.70 (m, 2H), 7.62 (dd, J = 8.5, 2.4 Hz, 1H), 7.45 (ddd, J = 8.2, 6.5, 1.7 Hz, 1H), 6.78 – 6.74 (m, 2H), 6.71 (s, 1H), 3.82 (s, 3H), 3.80 (d, J = 5.7 Hz, 2H), 3.72 (t, J = | 522.4 [M+H]+ |

| | | yl)quinazolin-4-amine | 6.2 Hz, 2H), 3.56 (s, 2H), 2.71 (t, *J* = 5.0 Hz, 2H), 2.57 - 2.53 (m, 2H), 2.34 (s, 3H), 1.91 - 1.85 (m, 2H) | |
|---|---|---|---|---|
| 31 | | 2-(6-(((1*S*,4*S*)-5-((6-methoxypyridin-3-yl)methyl)-2,5-diazabicyclo[2.2.1]heptan-2-yl)pyridin-3-yl)-*N*-(5-methyl-1*H*-pyrazol-3-yl)quinazolin-4-amine | ¹H NMR (400 MHz, DMSO-d6) δ 12.21 (s, 1H), 10.26 (s, 1H), 9.14 - 9.10 (m, 1H), 8.58 (d, *J* = 8.3 Hz, 1H), 8.46 (dd, *J* = 8.9, 2.3 Hz, 1H), 8.09 - 8.04 (m, 1H), 7.80 - 7.71 (m, 2H), 7.66 (dd, *J* = 8.5, 2.4 Hz, 1H), 7.45 (ddd, *J* = 8.3, 6.4, 1.8 Hz, 1H), 6.75 (dd, *J* = 8.5, 0.7 Hz, 1H), 6.71 (s, 1H), 6.63 (d, *J* = 8.9 Hz, 1H), 4.78 (s, 1H), 3.82 (s, 3H), 3.64 (s, 2H), 3.57 (d, *J* = 10.6 Hz, 2H), 3.40 (dd, *J* = 9.9, 2.2 Hz, 1H), 2.87 (dd, *J* = 9.5, 2.1 Hz, 1H), 2.52 (d, *J* = 3.5 Hz, 1H), 2.34 (s, 3H), 1.94 (d, *J* = 9.4 Hz, 1H), 1.80 (d, *J* = 9.3 Hz, 1H) | 520.5 [M+H]+ |
| 32 | | 2-(6-((2*R*,5*S*)-4-((6-methoxypyridin-3-yl)methyl)-2,5-dimethylpiperazin-1-yl)pyridin-3-yl)-*N*-(5-methyl-1*H*-pyrazol-3-yl)quinazolin-4-amine | ¹H NMR (400 MHz, DMSO-d6) δ 12.21 (s, 1H), 10.27 (s, 1H), 9.13 (d, *J* = 2.4 Hz, 1H), 8.59 (d, *J* = 8.2 Hz, 1H), 8.47 (dd, *J* = 9.0, 2.4 Hz, 1H), 8.11 (d, *J* = 2.3 Hz, 1H), 7.79 - 7.70 (m, 3H), 7.46 (ddd, *J* = 8.3, 6.4, 1.8 Hz, 1H), 6.90 - 6.71 (m, 3H), 4.58 (s, 1H), 4.16 - 4.09 (m, 1H), 3.85 (s, 3H), 3.61 (d, *J* = 13.5 Hz, 1H), 3.45 (d, *J* = 13.5 Hz, 1H), 3.30 (d, *J* = 3.7 Hz, 1H), 3.12 - 3.05 (m, 1H), 2.77 (dd, *J* = 11.7, 4.2 Hz, 1H), 2.34 (s, 3H), 2.30 (dd, *J* = 11.8, 1.9 Hz, 1H), 1.17 (d, *J* = 6.6 Hz, 3H), 1.00 (d, *J* = 6.5 Hz, 3H) | 536.5 [M+H]+ |
| 33 | | (*S*)-2-(6-(4-((6-methoxypyridin-3-yl)methyl)-3-methylpiperazin-1-yl)pyridin-3-yl)-*N*-(5-methyl-1*H*-pyrazol-3-yl)quinazolin-4-amine | ¹H NMR (400 MHz, DMSO-d6) δ 12.20 (s, 1H), 10.29 (s, 1H), 9.14 (d, *J* = 2.4 Hz, 1H), 8.59 (d, *J* = 8.3 Hz, 1H), 8.48 (dd, *J* = 9.0, 2.4 Hz, 1H), 8.08 (d, *J* = 2.4 Hz, 1H), 7.81 - 7.72 (m, 2H), 7.66 (dd, *J* = 8.5, 2.4 Hz, 1H), 7.46 (ddd, *J* = 8.3, 6.3, 1.9 Hz, 1H), 6.94 (d, *J* = 9.1 Hz, 1H), 6.80 (dd, *J* = 8.4, 0.7 Hz, 1H), 6.70 (s, 1H), 4.12 - 4.05 (m, 1H), 4.04 - 3.96 (m, 1H), 3.92 (d, *J* = 13.5 Hz, 1H), 3.84 (s, 3H), 3.20 (d, *J* = 13.4 Hz, 1H), 3.18 - 3.11 (m, 1H), 2.97 (dd, *J* = 12.8, 8.8 Hz, 1H), 2.70 (dt, *J* = 11.7, 3.6 Hz, 1H), 2.48 (dd, *J* = 6.0, 3.1 Hz, 1H), 2.33 (s, 3H), 2.16 (ddd, *J* = 11.3, 9.8, 3.3 Hz, 1H), 1.18 (d, *J* = 6.1 Hz, 3H) | 522.5 [M+H]+ |

| # | Structure | Name | NMR | MS |
|---|---|---|---|---|
| 34 | 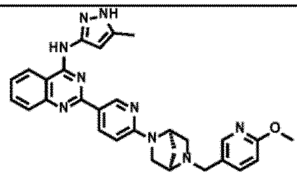 | 2-(6-((1R,4R)-5-((6-methoxypyridin-3-yl)methyl)-2,5-diazabicyclo[2.2.1]heptan-2-yl)pyridin-3-yl)-N-(5-methyl-1H-pyrazol-3-yl)quinazolin-4-amine | ¹H NMR (400 MHz, DMSO-d6) δ 12.18 (s, 1H), 10.27 (s, 1H), 9.15 - 9.10 (m, 1H), 8.58 (d, J = 8.3 Hz, 1H), 8.46 (dd, J = 8.9, 2.3 Hz, 1H), 8.09 - 8.03 (m, 1H), 7.81 - 7.71 (m, 2H), 7.66 (dd, J = 8.5, 2.4 Hz, 1H), 7.45 (ddd, J = 8.3, 6.4, 1.8 Hz, 1H), 6.78 - 6.59 (m, 3H), 4.78 (s, 1H), 3.82 (s, 3H), 3.64 (s, 2H), 3.57 (d, J = 10.3 Hz, 2H), 3.40 (dd, J = 9.9, 2.2 Hz, 1H), 2.87 (dd, J = 9.4, 2.1 Hz, 1H), 2.52 (d, J = 3.2 Hz, 1H), 2.34 (s, 3H), 1.94 (d, J = 9.3 Hz, 1H), 1.80 (d, J = 9.3 Hz, 1H) | 520.4 [M+H]+ |
| 35 | 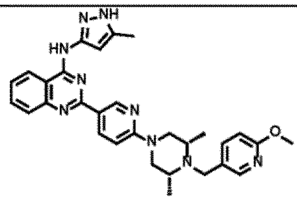 | 2-(6-((3R,5S)-4-((6-methoxypyridin-3-yl)methyl)-3,5-dimethylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.29 (s, 1H), 9.13 (d, J = 2.4 Hz, 1H), 8.59 (d, J = 8.3 Hz, 1H), 8.48 (dd, J = 9.0, 2.4 Hz, 1H), 8.15 (d, J = 2.4 Hz, 1H), 7.80 - 7.73 (m, 2H), 7.69 (dd, J = 8.5, 2.5 Hz, 1H), 7.46 (ddd, J = 8.2, 6.4, 1.9 Hz, 1H), 6.97 (d, J = 9.1 Hz, 1H), 6.77 (dd, J = 8.5, 0.6 Hz, 1H), 6.70 (s, 1H), 4.26 (d, J = 11.1 Hz, 2H), 3.82 (s, 3H), 3.76 (s, 2H), 2.75 (dd, J = 12.9, 10.2 Hz, 2H), 2.63 - 2.55 (m, 2H), 2.34 (s, 3H), 1.09 (d, J = 6.0 Hz, 6H) | 536.5 [M+H]+ |
| 36 | 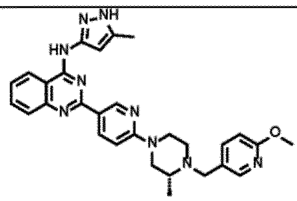 | (R)-2-(6-(4-((6-methoxypyridin-3-yl)methyl)-3-methylpiperazin-1-yl)pyridin-3-yl)-N-(5-methyl-1H-pyrazol-3-yl)quinazolin-4-amine | ¹H NMR (400 MHz, DMSO-d6) δ 12.21 (s, 1H), 10.29 (s, 1H), 9.14 (d, J = 2.4 Hz, 1H), 8.59 (d, J = 8.3 Hz, 1H), 8.48 (dd, J = 9.0, 2.4 Hz, 1H), 8.08 (d, J = 2.4 Hz, 1H), 7.81 - 7.73 (m, 2H), 7.66 (dd, J = 8.5, 2.4 Hz, 1H), 7.46 (ddd, J = 8.3, 6.3, 1.9 Hz, 1H), 6.94 (d, J = 9.0 Hz, 1H), 6.80 (dd, J = 8.4, 0.7 Hz, 1H), 6.71 (s, 1H), 4.08 (dt, J = 12.3, 3.0 Hz, 1H), 4.00 (d, J = 12.7 Hz, 1H), 3.92 (d, J = 13.5 Hz, 1H), 3.84 (s, 3H), 3.20 (d, J = 13.4 Hz, 1H), 3.15 (ddd, J = 12.8, 8.2, 3.4 Hz, 1H), 2.97 (dd, J = 12.8, 8.8 Hz, 1H), 2.74 - 2.66 (m, 1H), 2.50 - 2.46 (m, 1H), 2.33 (s, 3H), 2.16 (ddd, J = 13.0, 10.4, 3.2 Hz, 1H), 1.18 (d, J = 6.1 Hz, 3H) | 522.5 [M+H]+ |

| 37 | [structure] | 2-(6-(4-((6-methoxypyridin-3-yl)methyl)-4,7-diazaspiro[2.5]octan-7-yl)pyridin-3-yl)-N-(5-methyl-1H-pyrazol-3-yl)quinazolin-4-amine | $^1$H NMR (400 MHz, DMSO-d6) δ 12.21 (s, 1H), 10.29 (s, 1H), 9.15 (d, J = 2.4 Hz, 1H), 8.59 (d, J = 8.3 Hz, 1H), 8.49 (dd, J = 9.0, 2.4 Hz, 1H), 8.10 - 8.05 (m, 1H), 7.81 - 7.73 (m, 2H), 7.62 (dd, J = 8.5, 2.4 Hz, 1H), 7.46 (ddd, J = 8.3, 6.3, 1.9 Hz, 1H), 6.93 (d, J = 9.1 Hz, 1H), 6.78 (ddd, J = 8.4, 2.4, 0.7 Hz, 1H), 6.71 (d, J = 8.1 Hz, 1H), 3.83 (q, J = 5.8, 5.3 Hz, 6H), 3.70 - 3.65 (m, 2H), 3.57 (s, 2H), 2.84 - 2.78 (m, 2H), 2.33 (s, 3H), 0.64 (dt, J = 11.8, 1.9 Hz, 3H) | 534.5 [M+H]+ |

In the Claims

Column 47, Line 28, Claim 6: Please correct "comprising," to read --comprising--